(12) United States Patent
Scheller et al.

(10) Patent No.: US 9,237,966 B2
(45) Date of Patent: *Jan. 19, 2016

(54) STEERABLE LASER PROBE

(71) Applicant: Katalyst Surgical, LLC, Chesterfield, MO (US)

(72) Inventors: Gregg D Scheller, Wildwood, MO (US); Craig Moore, O'Fallon, MO (US); Matthew N Zeid, Ballwin, MO (US)

(73) Assignee: Katalyst Surgical, LLC, Chesterfield, MO (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/695,592

(22) Filed: Apr. 24, 2015

(65) Prior Publication Data

US 2015/0223986 A1    Aug. 13, 2015

Related U.S. Application Data

(63) Continuation of application No. 13/586,821, filed on Aug. 15, 2012, now Pat. No. 9,089,399.

(51) Int. Cl.
*A61B 18/18*    (2006.01)
*A61F 9/008*    (2006.01)
(Continued)

(52) U.S. Cl.
CPC .............. *A61F 9/00821* (2013.01); *A61B 18/22* (2013.01); *A61F 9/00823* (2013.01); *A61B 2017/00331* (2013.01); *A61B 2017/00336* (2013.01); *A61B 2017/00867* (2013.01); *A61B 2018/0091* (2013.01);
(Continued)

(58) Field of Classification Search
CPC ........... A61B 18/22; A61B 2018/0091; A61B 2018/2238; A61B 2018/2288; A61B 2018/22; A61B 2017/0023; A61B 2017/00318; A61B 2017/00331; A61B 2017/00867; A61B 2017/2909; A61B 2017/2918; A61F 9/008; A61F 9/0082; A61F 2009/00863
USPC ........................ 606/1, 4, 6, 13–16; 607/88–92
See application file for complete search history.

(56) References Cited

U.S. PATENT DOCUMENTS 5,190,050 A    3/1993    Nitzsche
5,355,871 A    10/1994    Hurley et al.
(Continued)

FOREIGN PATENT DOCUMENTS

EP            0900547 B1    3/1999
WO    WO 2006/091597 A1    8/2006

OTHER PUBLICATIONS

H. Fischer, B. Vogel, W. Pfleging, H. Besser, Flexible distal tip made of nitinol (NiTi) for a steerable endoscopic camera system, Materials Science and Engineering A273-275 (1999) 780-783.

*Primary Examiner* — Ahmed Farah
(74) *Attorney, Agent, or Firm* — Kevin P. Rollins

(57) ABSTRACT

A steerable laser probe may include a handle having a handle distal end and a handle proximal end, a housing sleeve disposed in an inner bore of the handle configured to project a distance from the handle distal end, an optic fiber disposed in the housing sleeve, a shape memory sleeve disposed over a distal end of the optic fiber, and a light source configured to connect to a proximal end of the optic fiber. The shape memory sleeve may be configured to curve the distal end of the optic fiber at an angle, e.g., 90 degrees, when the shape memory sleeve is not contained within the housing sleeve.

20 Claims, 38 Drawing Sheets

(51) Int. Cl.
  *A61B 18/22*  (2006.01)
  *A61B 17/00*  (2006.01)
  *A61B 18/00*  (2006.01)

(52) U.S. Cl.
  CPC  *A61B 2018/00589* (2013.01); *A61B 2018/225* (2013.01); *A61B 2018/2238* (2013.01); *A61F 2009/00863* (2013.01); *A61F 2009/00874* (2013.01)

(56)  References Cited

U.S. PATENT DOCUMENTS

| | | | |
|---|---|---|---|
| 5,381,782 A | 1/1995 | DeLaRama et al. | |
| 5,439,000 A | 8/1995 | Gunderson et al. | |
| 5,454,794 A | 10/1995 | Narciso et al. | |
| 5,520,222 A | 5/1996 | Chikama | |
| 5,855,577 A * | 1/1999 | Murphy-Chutorian et al. | 606/7 |
| 6,123,699 A | 9/2000 | Webster, Jr. | |
| 6,126,654 A | 10/2000 | Giba et al. | |
| 6,198,974 B1 | 3/2001 | Webster, Jr. | |
| 6,488,695 B1 | 12/2002 | Hickingbotham | |
| 6,505,530 B2 | 1/2003 | Adler et al. | |
| 6,530,913 B1 | 3/2003 | Giba et al. | |
| 6,551,302 B1 | 4/2003 | Rosinko et al. | |
| 6,572,608 B1 | 6/2003 | Lee et al. | |
| 6,620,153 B2 | 9/2003 | Mueller et al. | |
| 6,730,076 B2 | 5/2004 | Hickingbotham | |
| 6,863,668 B2 | 3/2005 | Gillespie et al. | |
| 6,984,230 B2 | 1/2006 | Scheller et al. | |
| 7,004,957 B1 | 2/2006 | Dampney et al. | |
| 7,303,533 B2 | 12/2007 | Johansen et al. | |
| 7,402,158 B2 | 7/2008 | Scheller et al. | |
| 7,632,242 B2 | 12/2009 | Griffin et al. | |
| 7,766,904 B2 | 8/2010 | Mc Gowan, Sr. et al. | |
| 8,038,692 B2 | 10/2011 | Valencia et al. | |
| 8,075,553 B2 | 12/2011 | Scheller et al. | |
| 8,197,468 B2 | 6/2012 | Scheller et al. | |
| 8,317,778 B2 * | 11/2012 | Spaide | 606/4 |
| 8,579,887 B2 * | 11/2013 | Hanlon et al. | 606/1 |
| 8,840,605 B2 * | 9/2014 | Scheller et al. | 606/15 |
| 9,089,399 B2 * | 7/2015 | Scheller | A61F 9/00823 |
| 2003/0171762 A1 | 9/2003 | Forchette et al. | |
| 2004/0181138 A1 | 9/2004 | Hindricks et al. | |
| 2004/0249367 A1 | 12/2004 | Saadat et al. | |
| 2005/0054900 A1 | 3/2005 | Mawn et al. | |
| 2005/0157985 A1 | 7/2005 | McGowan, Sr. et al. | |
| 2005/0272975 A1 | 12/2005 | McWeeney et al. | |
| 2005/0277874 A1 | 12/2005 | Selkee | |
| 2007/0185514 A1 | 8/2007 | Kirchhevel | |
| 2009/0018393 A1 | 1/2009 | Dick et al. | |
| 2009/0187170 A1 | 7/2009 | Auld et al. | |
| 2009/0312750 A1 | 12/2009 | Spaide | |
| 2010/0004642 A1 | 1/2010 | Lumpkin | |
| 2010/0268234 A1 | 10/2010 | Aho et al. | |
| 2011/0028947 A1 | 2/2011 | Scheller et al. | |
| 2012/0116361 A1 | 5/2012 | Hanlon et al. | |
| 2013/0035551 A1 | 2/2013 | Yu et al. | |
| 2013/0060240 A1 | 3/2013 | Scheller et al. | |
| 2013/0071507 A1 | 3/2013 | Scheller et al. | |
| 2013/0096541 A1 | 4/2013 | Scheller et al. | |
| 2013/0116671 A1 | 5/2013 | Scheller et al. | |
| 2013/0150838 A1 | 6/2013 | Scheller et al. | |
| 2013/0165910 A1 | 6/2013 | Scheller et al. | |
| 2013/0261610 A1 | 10/2013 | LaConte et al. | |

* cited by examiner

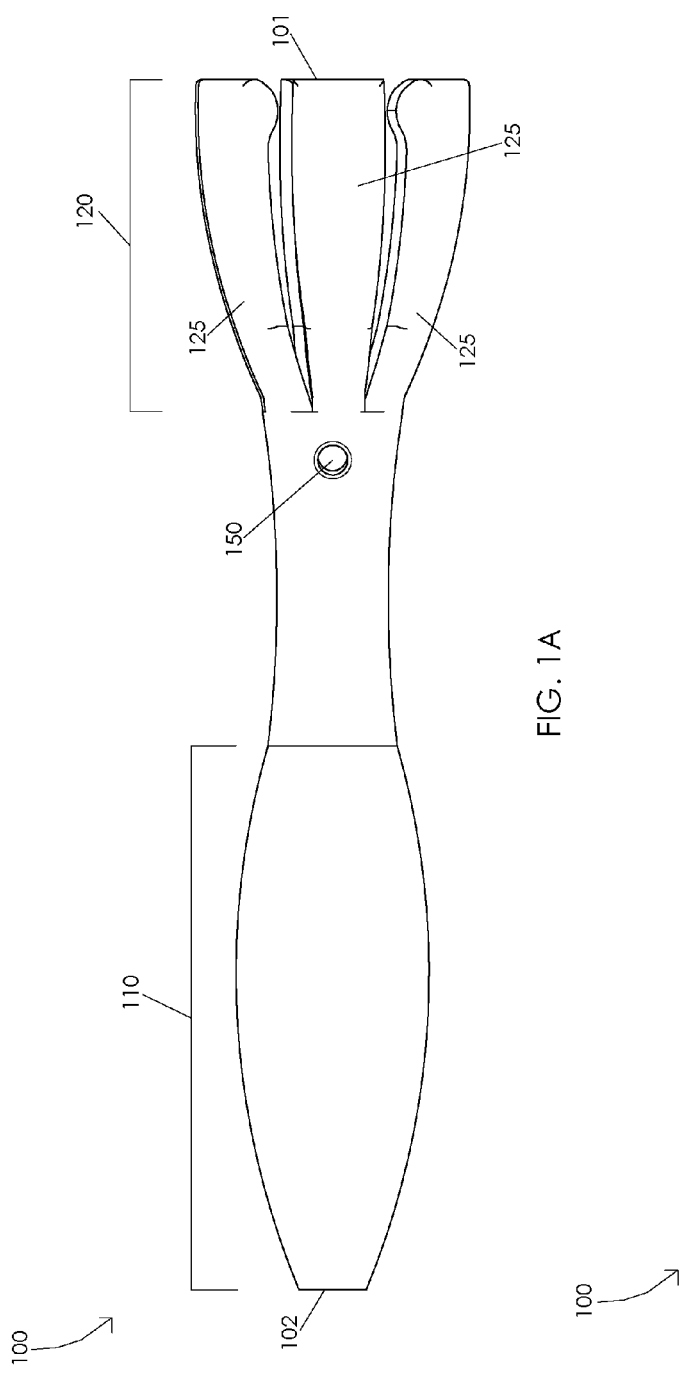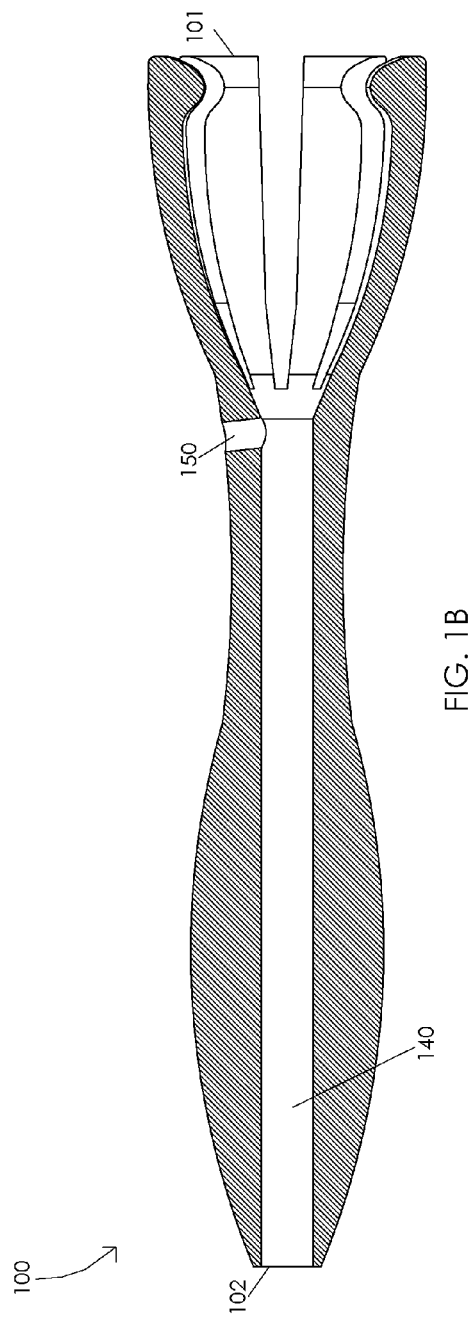
FIG. 1A
FIG. 1B

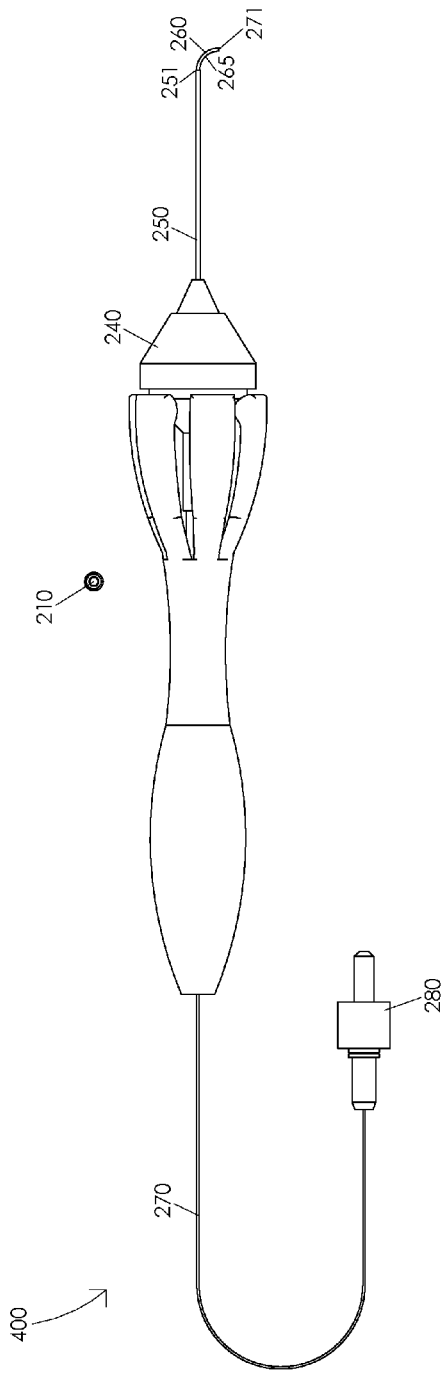
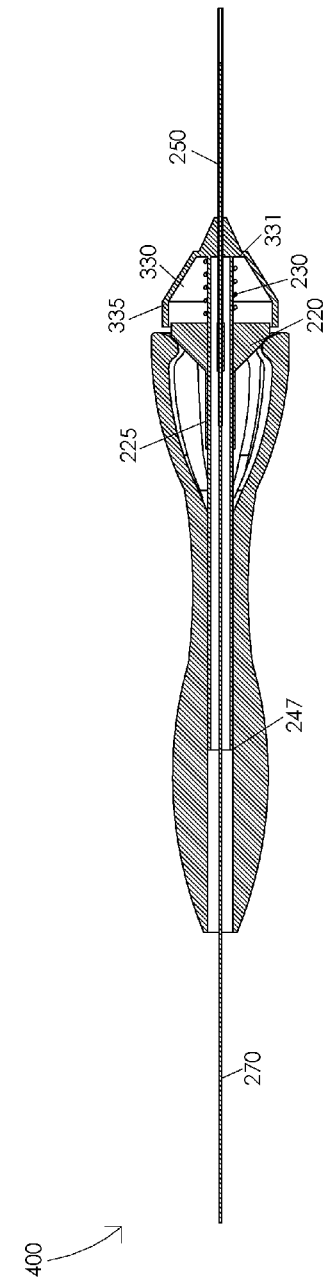
FIG. 4A
FIG. 4B

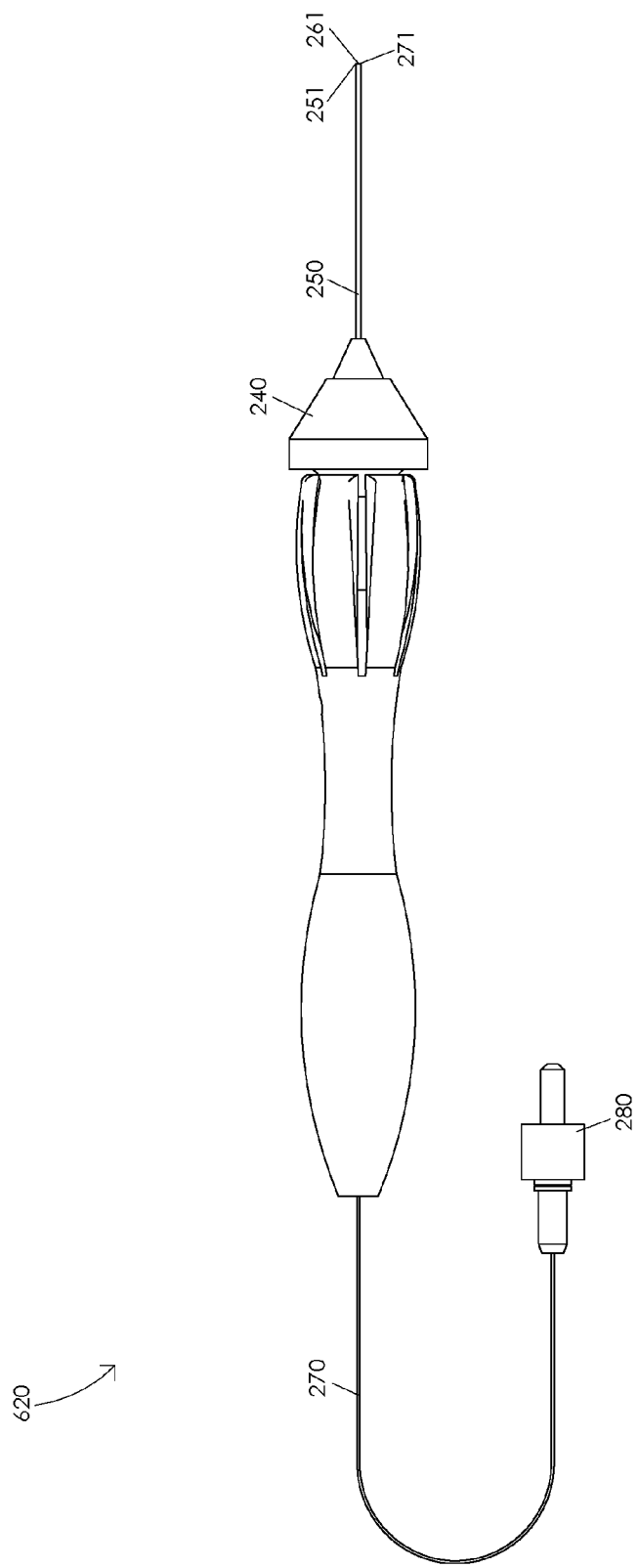

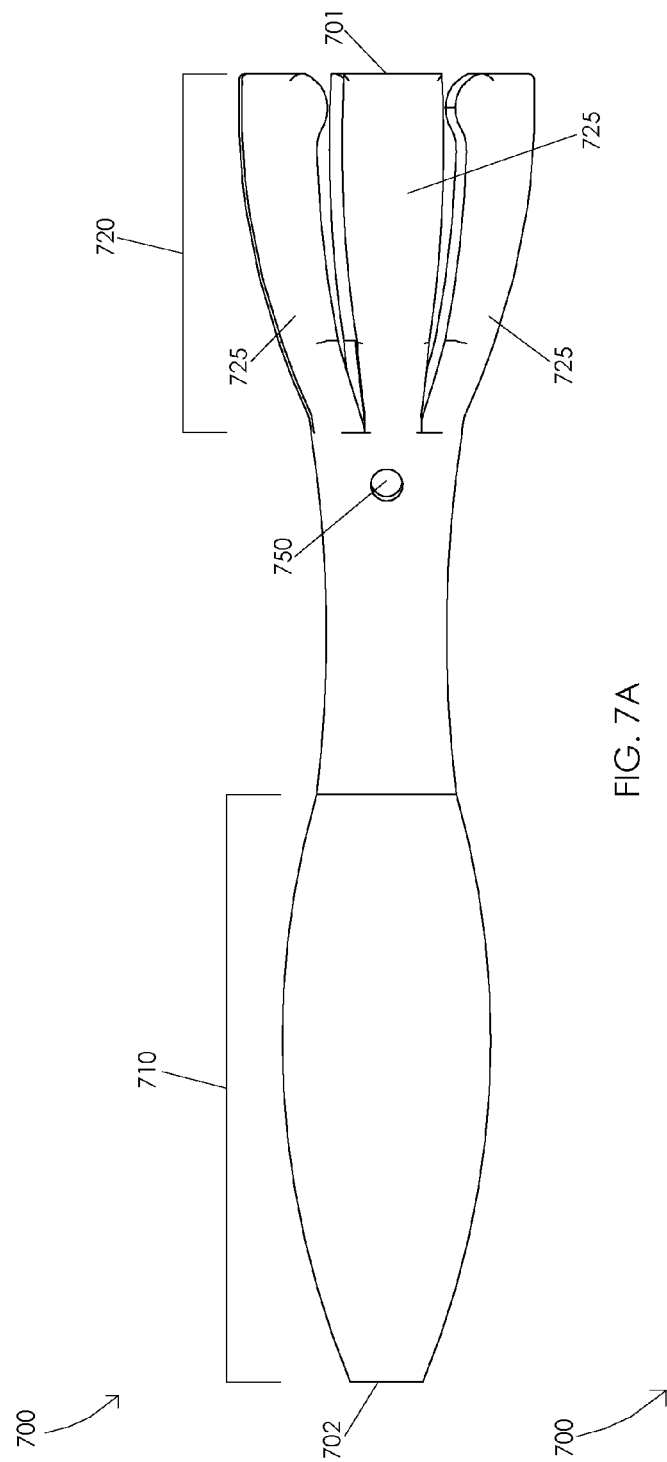
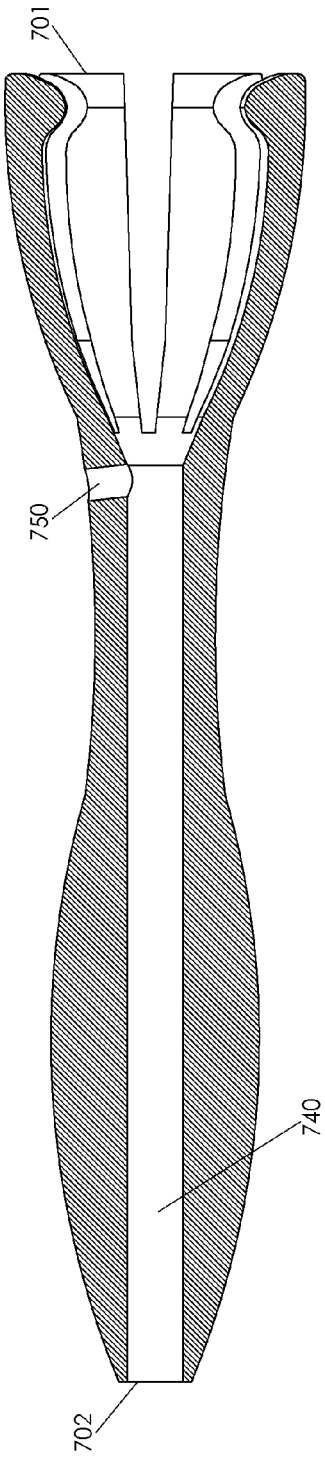
FIG. 7A
FIG. 7B

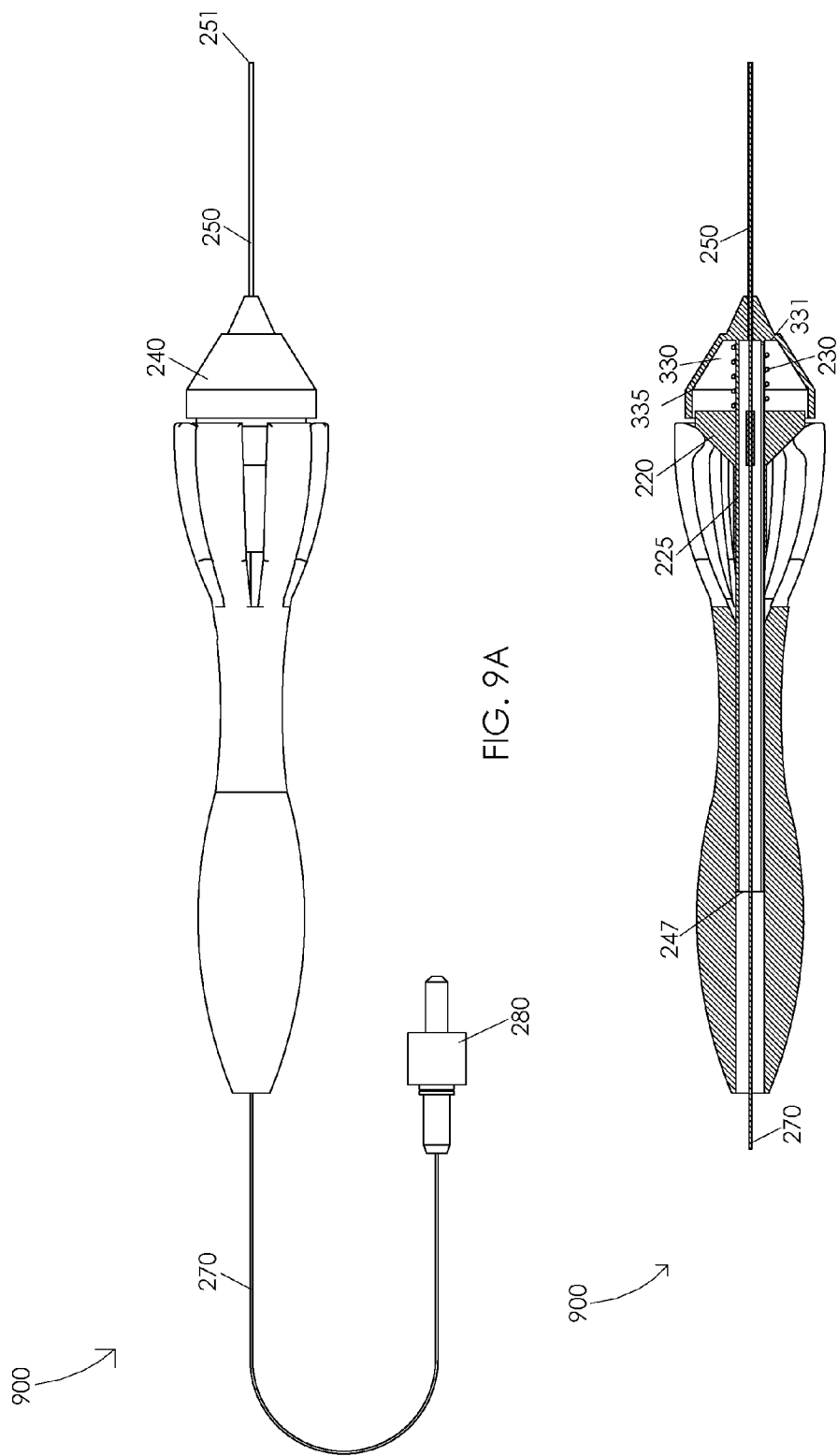

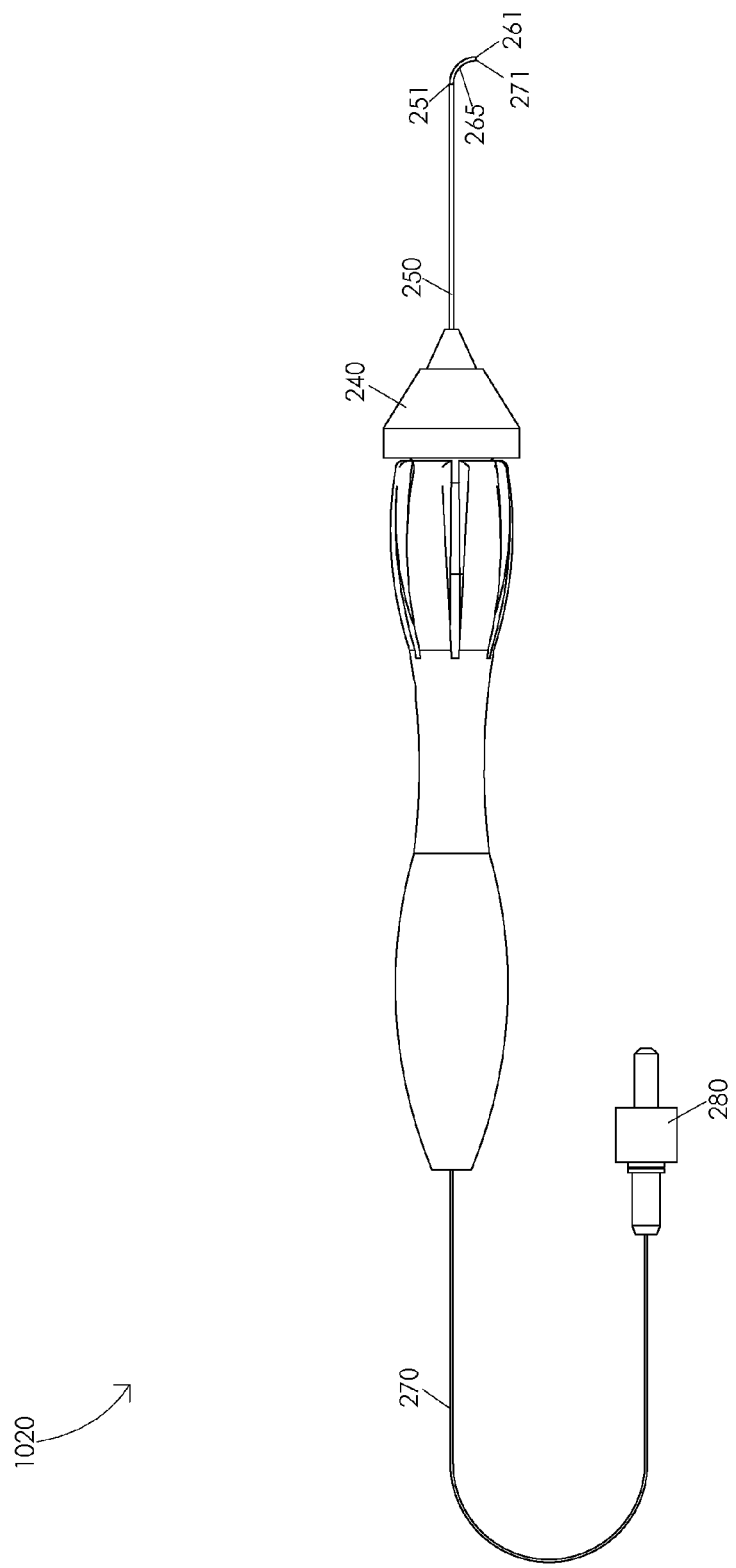

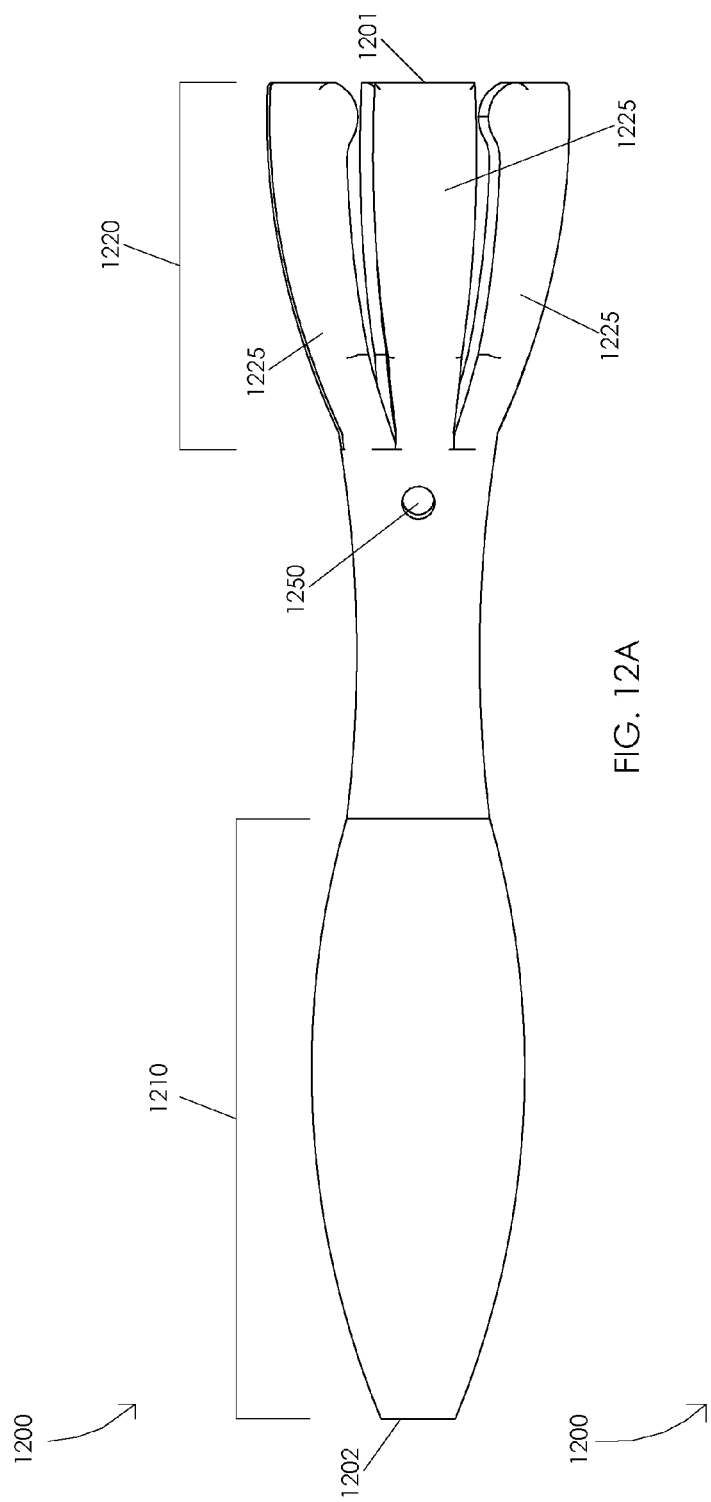
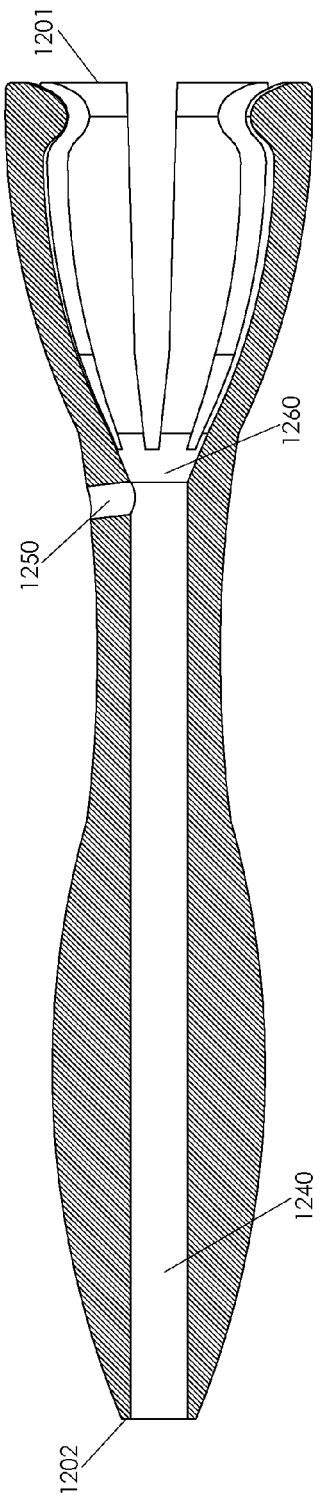
FIG. 12A
FIG. 12B

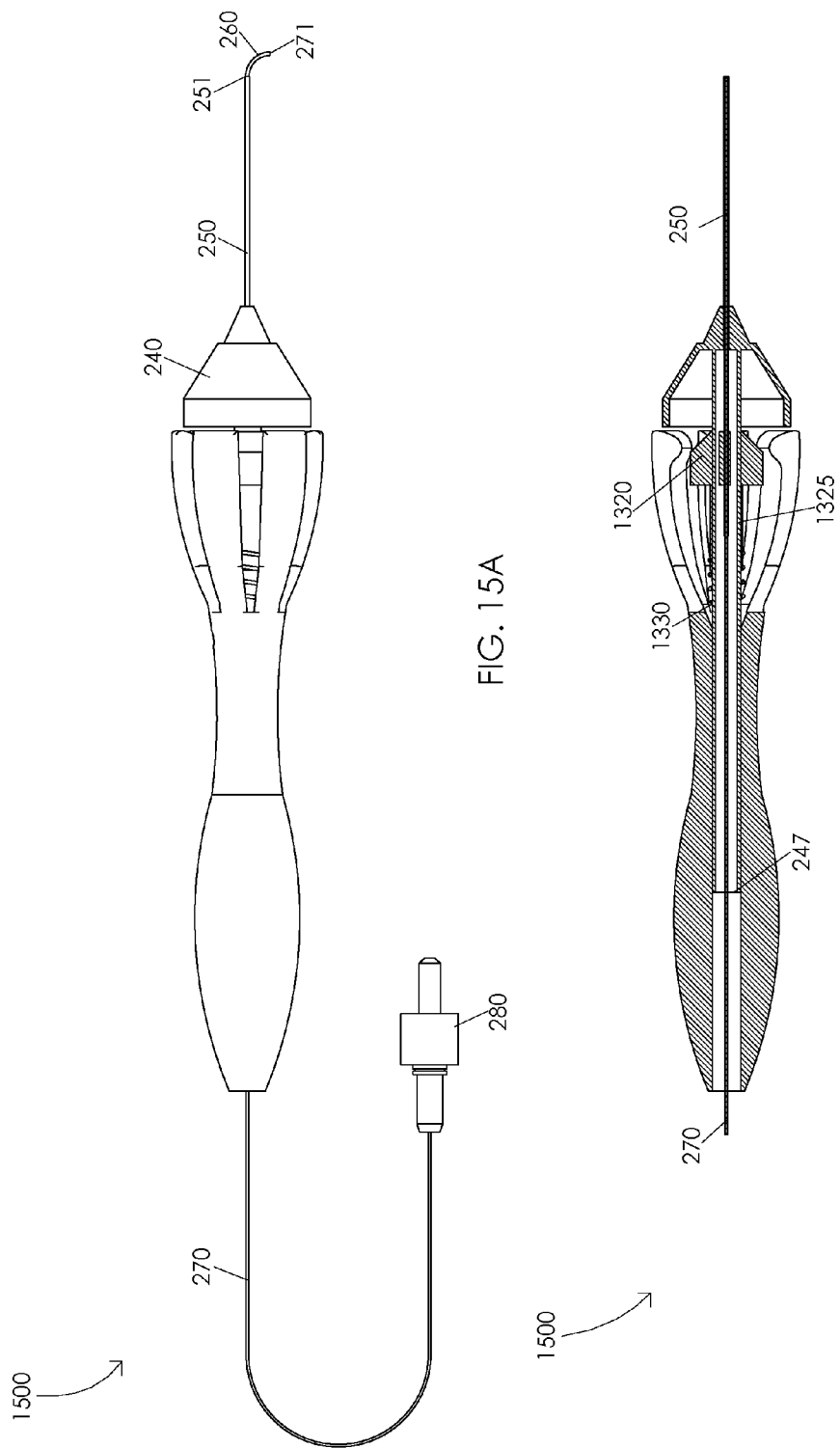

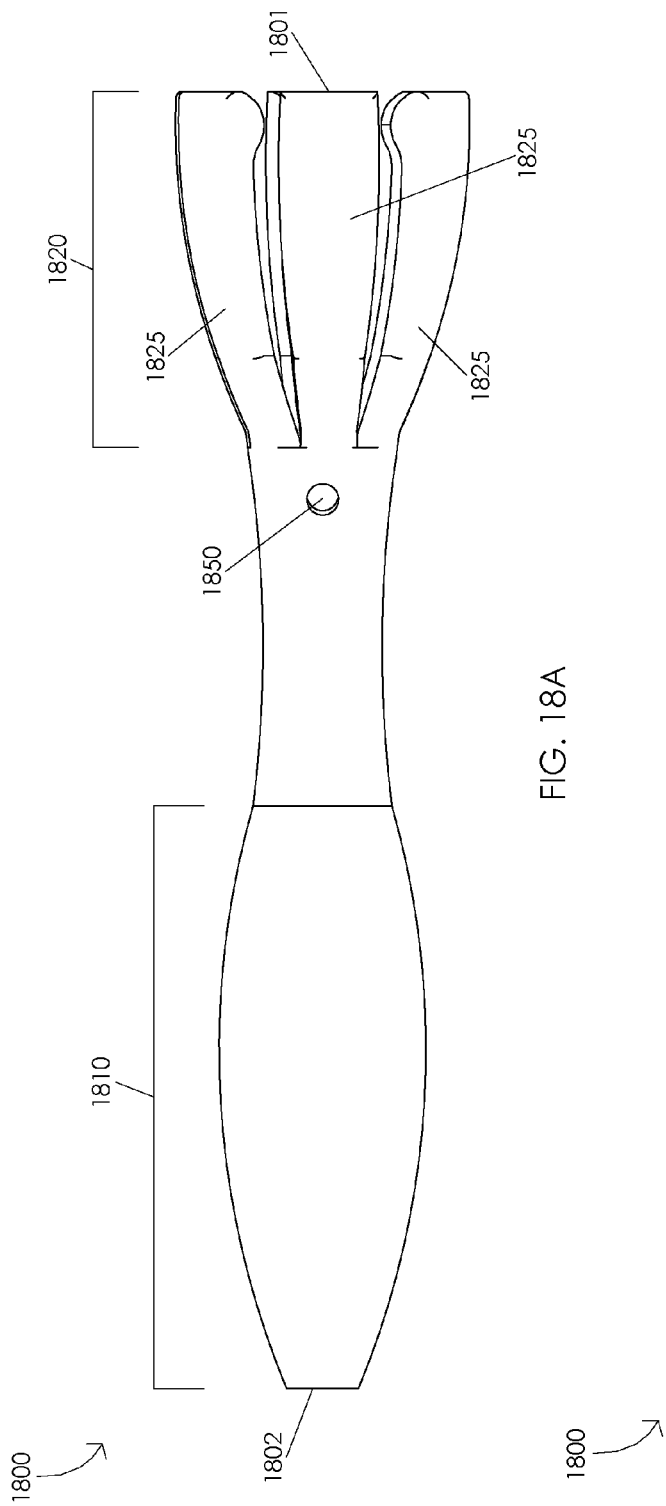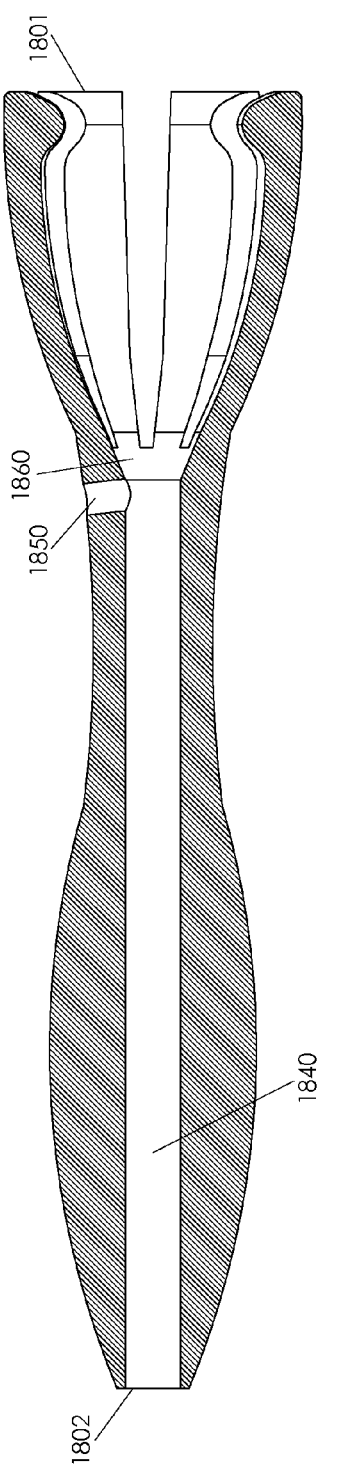
FIG. 18A
FIG. 18B

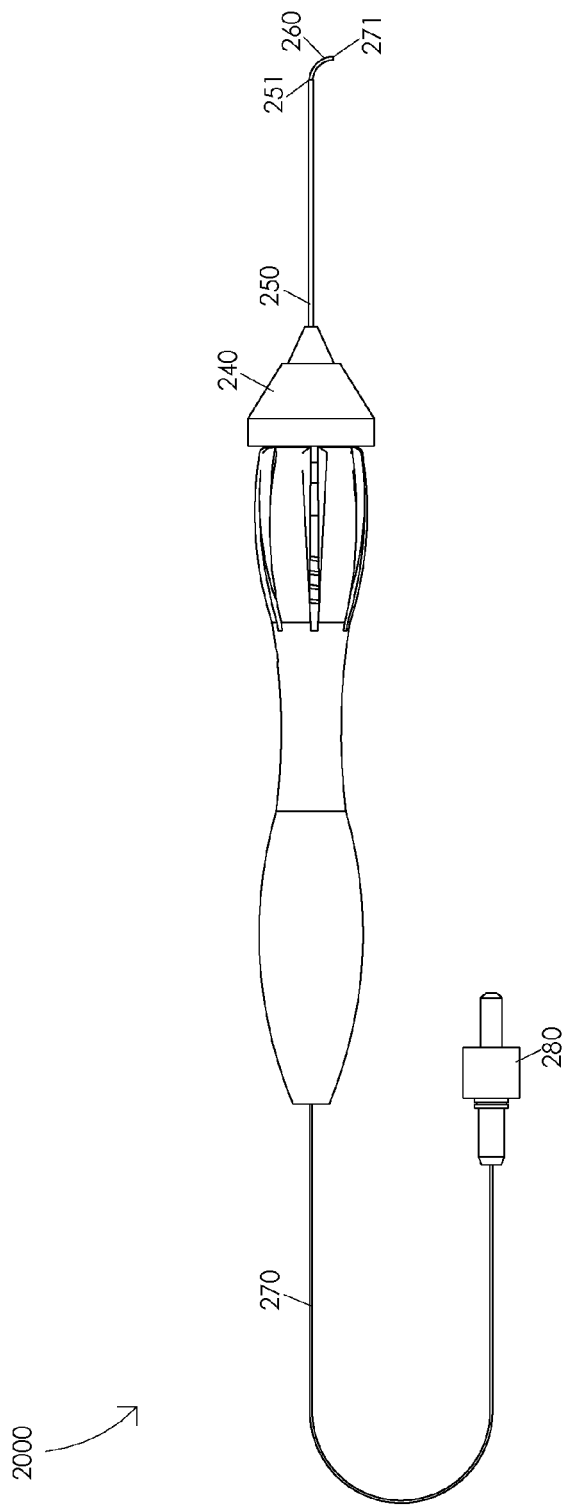
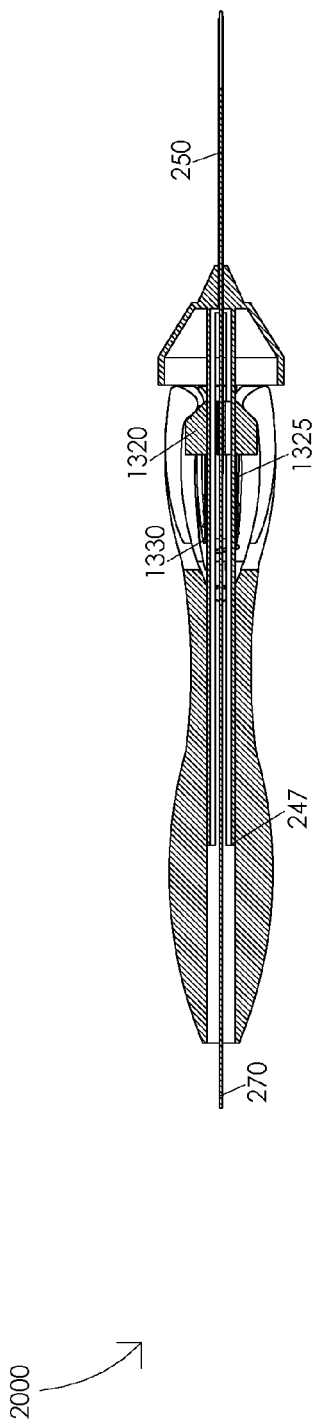
FIG. 20A
FIG. 20B

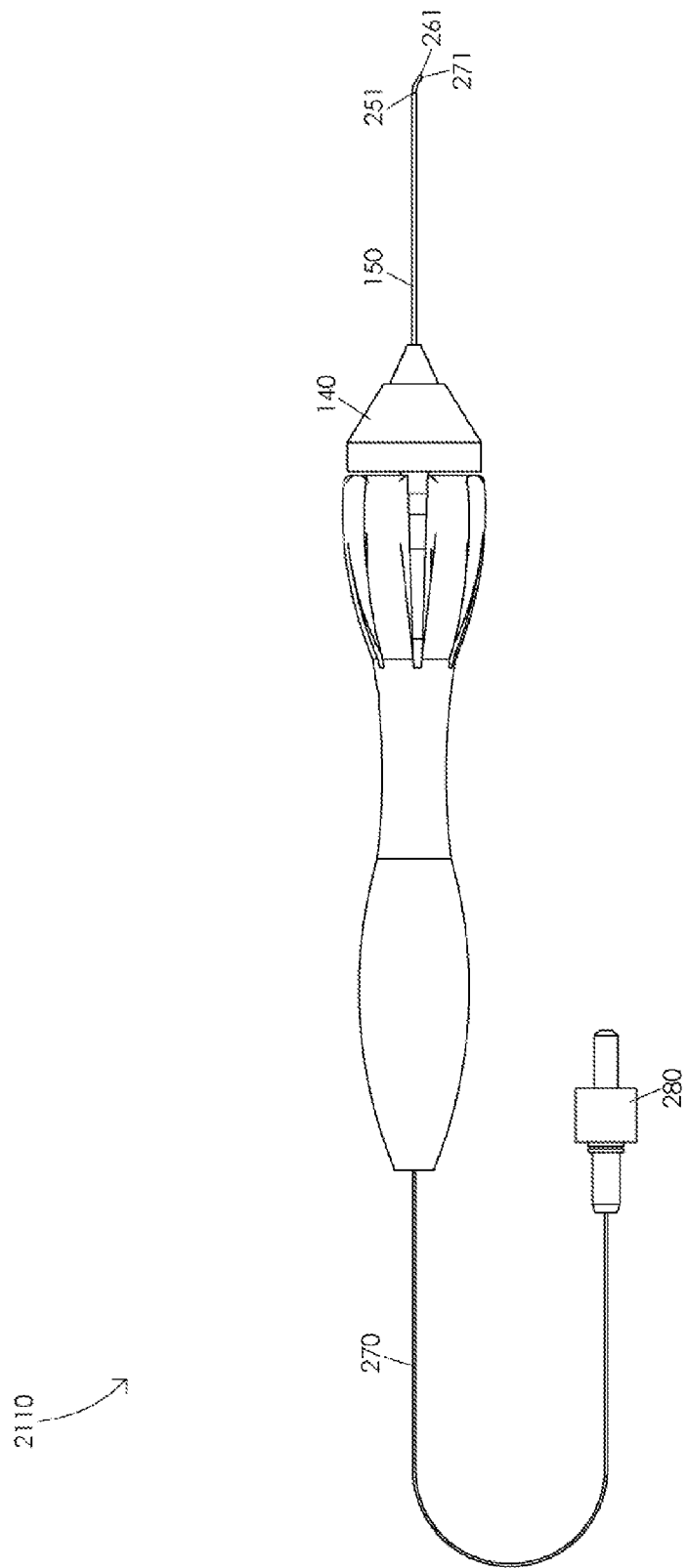

STEERABLE LASER PROBE

CROSS-REFERENCE TO RELATED APPLICATIONS

This Application is a continuation of prior application Ser. No. 13/586,821, filed Aug. 15, 2012.

FIELD OF THE INVENTION

The present disclosure relates to a surgical instrument, and, more particularly, to a steerable laser probe.

BACKGROUND OF THE INVENTION

A wide variety of ophthalmic procedures require a laser energy source. For example, ophthalmic surgeons may use laser photocoagulation to treat proliferative retinopathy. Proliferative retinopathy is a condition characterized by the development of abnormal blood vessels in the retina that grow into the vitreous humor. Ophthalmic surgeons may treat this condition by energizing a laser to cauterize portions of the retina to prevent the abnormal blood vessels from growing and hemorrhaging.

In order to increase the chances of a successful laser photocoagulation procedure, it is important that a surgeon is able aim the laser at a plurality of targets within the eye, e.g., by guiding or moving the laser from a first target to a second target within the eye. It is also important that the surgeon is able to easily control a movement of the laser. For example, the surgeon must be able to easily direct a laser beam by steering the beam to a first position aimed at a first target, guide the laser beam from the first position to a second position aimed at a second target, and hold the laser beam in the second position. Accordingly, there is a need for a surgical laser probe that can be easily guided to a plurality of targets within the eye.

BRIEF SUMMARY OF THE INVENTION

The present disclosure provides a steerable laser probe. In one or more embodiments, a steerable laser probe may comprise a handle having a handle distal end and a handle proximal end, a housing sleeve, an optic fiber disposed in the housing sleeve, a shape memory sleeve disposed over a distal end of the optic fiber, and a light source interface configured to interface with a proximal end of the optic fiber. Illustratively, the shape memory sleeve may be configured to hold the distal end of the optic fiber at a pre-bent angle, e.g., 90 degrees, when the shape memory sleeve is not contained within the housing sleeve.

In one or more embodiments, a compression of an actuation structure of the handle actuates the housing sleeve relative to the shape memory sleeve and the optic fiber wherein the housing sleeve is gradually extended over the shape memory sleeve and the optic fiber. Illustratively, the shape memory sleeve and the optic fiber are gradually straightened as the housing sleeve is gradually extended over the shape memory sleeve and the optic fiber. In one or more embodiments, a decompression of the actuation structure actuates the housing sleeve relative to the shape memory sleeve and the optic fiber wherein the housing sleeve is gradually retracted and the shape memory sleeve and the optic fiber are gradually exposed by the housing sleeve. Illustratively, the shape memory sleeve gradually curves the optic fiber as the shape memory sleeve and the optic fiber are gradually exposed by the housing sleeve.

In one or more embodiments, a compression of an actuation structure of the handle actuates the optic fiber and the shape memory sleeve relative to the housing sleeve wherein the optic fiber and the shape memory sleeve are gradually extended from the housing sleeve. Illustratively, the shape memory sleeve and the optic fiber are gradually curved as the shape memory sleeve and the optic fiber are gradually extended from the shape memory sleeve. In one or more embodiments, a decompression of the actuation structure actuates the optic fiber and the shape memory sleeve relative to the housing sleeve wherein the optic fiber and the shape memory sleeve are gradually retracted into the housing sleeve. Illustratively, the housing sleeve gradually straightens the shape memory sleeve and the optic fiber as the shape memory sleeve and the optic fiber are gradually retracted into the housing sleeve.

In one or more embodiments, a compression of an actuation structure of the handle actuates the optic fiber and the shape memory sleeve relative to the housing sleeve wherein the optic fiber and the shape memory sleeve are gradually retracted into the housing sleeve. Illustratively, the shape memory sleeve and the optic fiber are gradually straightened as the shape memory sleeve and the optic fiber are gradually retracted into the housing sleeve. In one or more embodiments, a decompression of the actuation structure actuates the optic fiber and the shape memory sleeve relative to the housing sleeve wherein the optic fiber and the shape memory sleeve are gradually extended from the housing sleeve. Illustratively, the shape memory sleeve and the optic fiber are gradually curved as the shape memory sleeve and the optic fiber are gradually extended from the housing sleeve.

In one or more embodiments, a compression of an actuation structure of the handle actuates the housing sleeve relative to the optic fiber and the shape memory sleeve wherein the housing sleeve is gradually retracted to expose the optic fiber and the shape memory sleeve. Illustratively, the shape memory sleeve and the optic fiber are gradually curved as the shape memory sleeve and the optic fiber are gradually exposed by the housing sleeve. In one or more embodiments, a decompression of the actuation structure actuates the housing sleeve relative to the optic fiber and the shape memory sleeve wherein the housing sleeve is gradually extended over the shape memory sleeve and the optic fiber. Illustratively, the shape memory sleeve and the optic fiber are gradually straightened as the housing sleeve is gradually extended over the shape memory sleeve and the optic fiber.

BRIEF DESCRIPTION OF THE DRAWINGS

The above and further advantages of the present invention may be better understood by referring to the following description in conjunction with the accompanying drawings in which like reference numerals indicate identical or functionally similar elements:

FIGS. 1A and 1B are schematic diagrams illustrating a handle;

FIGS. 4A and 4B are schematic diagrams illustrating an assembled steerable laser probe;

FIGS. 6A, 6B, and 6C are schematic diagrams illustrating a gradual straightening of an optic fiber;

FIGS. 7A and 7B are schematic diagrams illustrating a handle;

FIGS. 9A and 9B are schematic diagrams illustrating an assembled steerable laser probe;

FIGS. 10A, 10B, and 10C are schematic diagrams illustrating a gradual curving of an optic fiber;

FIGS. 12A and 12B are schematic diagrams illustrating a handle;

FIGS. 15A and 15B are schematic diagrams illustrating an assembled steerable laser probe;

FIGS. 18A and 18B are schematic diagrams illustrating a handle;

FIGS. 20A and 20B are schematic diagrams illustrating an assembled steerable laser probe;

FIGS. 21A, 21B, and 21C are schematic diagrams illustrating a gradual curving of an optic fiber;

DETAILED DESCRIPTION OF AN ILLUSTRATIVE EMBODIMENT

Figure 2:
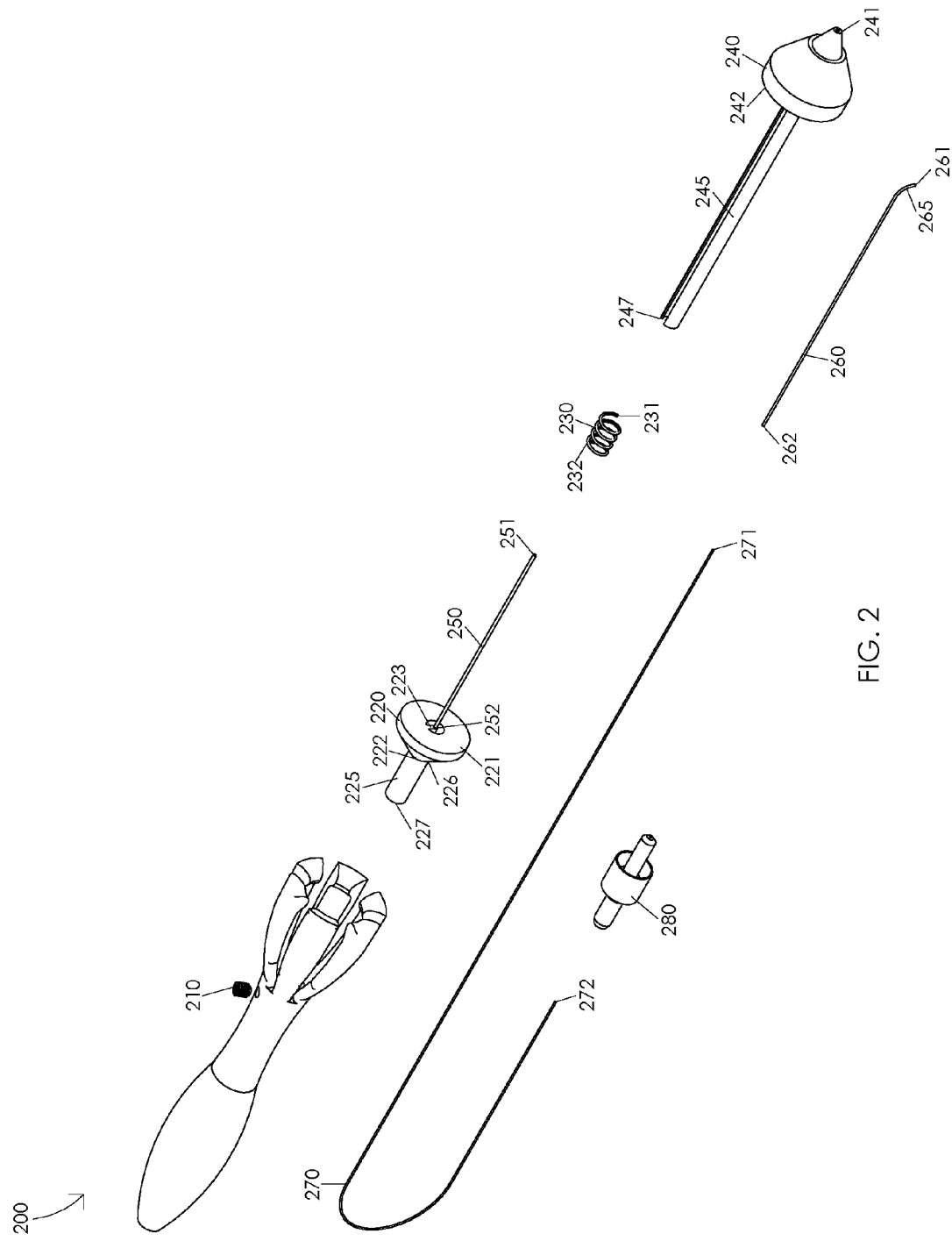
FIG. 2 illustrates an exploded view of a steerable laser probe assembly.

FIGS. 1A and 1B are schematic diagrams illustrating a handle 100. FIG. 1A illustrates a top view of handle 100. In one or more embodiments, handle 100 may comprise a handle distal end 101, a handle proximal end 102, a handle base 110, and an actuation structure 120. Illustratively, actuation structure 120 may comprise a plurality of actuation arms 125. In one or more embodiments, actuation structure 120 may comprise a shape memory material. Actuation structure 120 may be manufactured from any suitable material, e.g., polymers, metals, metal alloys, etc., or from any combination of suitable materials.

Illustratively, actuation structure 120 may be compressed by an application of a compressive force to actuation structure 120. In one or more embodiments, actuation structure 120 may be compressed by an application of one or more compressive forces located at one or more locations around an outer perimeter of actuation structure 120. Illustratively, the one or more locations may comprise any of a plurality of locations around the outer perimeter of actuation structure 120. For example, a surgeon may compress actuation structure 120 by squeezing actuation structure 120. Illustratively, the surgeon may compress actuation structure 120 by squeezing actuation structure 120 at any particular location of a plurality of locations around an outer perimeter of actuation structure 120. For example, a surgeon may rotate handle 100 and compress actuation structure 120 from any rotational position of a plurality of rotational positions of handle 100.

In one or more embodiments, actuation structure 120 may be compressed by an application of a compressive force to any one or more of the plurality of actuation arms 125. Illustratively, each actuation arm 125 may be configured to actuate independently. In one or more embodiments, each actuation arm 125 may be connected to one or more of the plurality of actuation arms 125 wherein an actuation of a particular actuation arm 125 may be configured to actuate every actuation arm 125 of the plurality of actuation arms 125. In one or more embodiments, a compression of actuation structure 120, e.g., due to an application of a compressive force to a particular actuation arm 125, may be configured to actuate the particular actuation arm 125. Illustratively, an actuation of the particular actuation arm 125 may be configured to actuate every actuation arm 125 of the plurality of actuation arms 125.

FIG. 1B illustrates a cross-sectional view of handle 100. In one or more embodiments, handle 100 may comprise an inner bore 140 and a fixation mechanism housing 150. Handle 100 may be manufactured from any suitable material, e.g., polymers, metals, metal alloys, etc., or from any combination of suitable materials.

FIG. 2 illustrates an exploded view of a steerable laser probe assembly 200. In one or more embodiments, steerable laser probe assembly 200 may comprise a handle 100, a fixation mechanism 210, an actuation mechanism 220 having an actuation mechanism distal end 221 and an actuation mechanism proximal end 222, a piston tube 225 having a piston tube distal end 226 and a piston tube proximal end 227, a pressure mechanism 230 having a pressure mechanism distal end 231 and a pressure mechanism proximal end 232, a nosecone 240 having a nosecone distal end 241 and a nosecone proximal end 242, an actuation guide 245 having an actuation guide proximal end 247, a housing sleeve 250 having a housing sleeve distal end 251 and a housing sleeve proximal end 252, a shape memory sleeve 260 having a shape memory sleeve distal end 261 and a shape memory sleeve proximal end 262, an optic fiber 270 having an optic fiber distal end 271 and an optic fiber proximal end 272, and a light source interface 280. Illustratively, light source interface 280 may be configured to interface with optic fiber proximal end 272. In one or more embodiments, light source interface 280 may comprise a standard light source connecter, e.g., an SMA connector.

Illustratively, actuation mechanism 220 may comprise an actuation guide interface 223 configured to interface with actuation guide 245. In one or more embodiments, piston tube 225 may be fixed to actuation mechanism proximal end 222. Illustratively, actuation mechanism distal end 221 may be fixed to housing sleeve proximal end 252. In one or more embodiments, actuation mechanism 220, piston tube 225, and housing sleeve 250 may be manufactured as a unit. Illustratively, actuation guide 245 may be fixed an inner portion of nosecone 240. In one or more embodiments, actuation guide 245 and nosecone 240 may be manufactured as a unit.

Figure 3A:
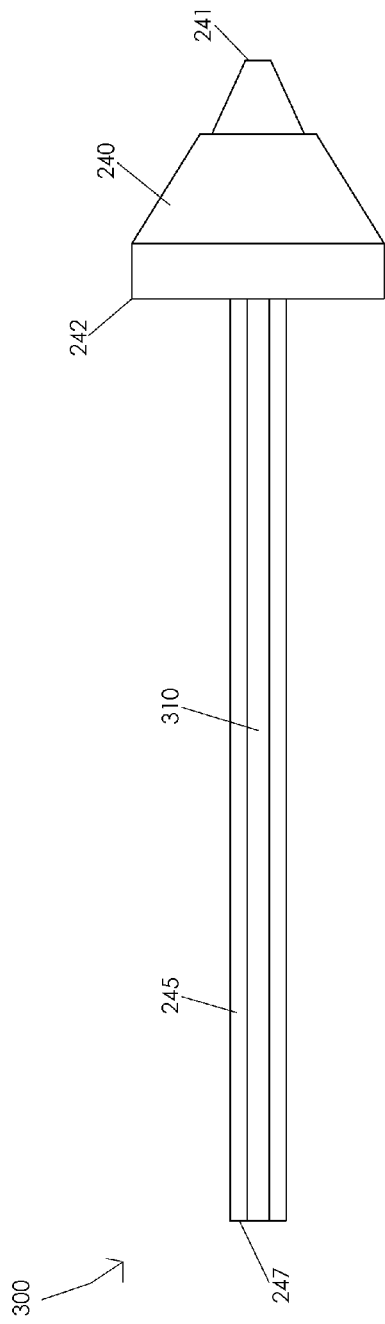
FIGS. 3A and 3B are schematic diagrams illustrating an assembled nosecone.
Figure 3B:
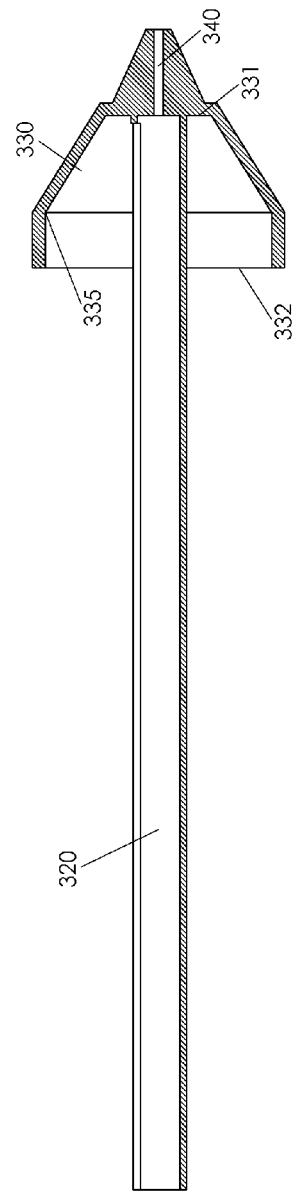

FIGS. 3A and 3B are schematic diagrams illustrating an assembled nosecone 300. FIG. 3A illustrates a top view of assembled nosecone 300. Illustratively, actuation guide 245 may comprise an actuation channel 310. FIG. 3B illustrates a cross-sectional view of assembled nosecone 300. Illustratively, actuation guide 245 may comprise an actuation guide inner bore 320. In one or more embodiments, nosecone 240 may comprise a nosecone inner chamber 330. Illustratively, nosecone inner chamber 330 may comprise a pressure mechanism distal interface 331 and a nosecone inner chamber proximal opening 332. In one or more embodiments, nosecone inner chamber 330 may comprise an actuation mechanism distal interface 335. Illustratively, nosecone 240 may comprise a housing sleeve guide 340 configured to guide an actuation of housing sleeve 250.

FIGS. 4A and 4B are schematic diagrams illustrating an assembled steerable laser probe 400. FIG. 4A illustrates a side view of an assembled steerable laser probe 400. Illustratively, optic fiber 270 may be disposed within shape memory sleeve 260, e.g., optic fiber distal end 271 may be adjacent to shape memory sleeve distal end 261. Optic fiber 270 may be fixed in a position within shape memory sleeve 260, e.g., by a biocompatible adhesive or any other suitable fixation means. In one or more embodiments, shape memory sleeve 260 may comprise a pre-bent angle 265 configured to curve optic fiber 270 towards pre-bent angle 265. Illustratively, shape memory sleeve 260 may comprise a shape memory material, e.g., nitinol, configured to steer optic fiber 270 towards one or more surgical targets within an eye. Shape memory sleeve 260 may be manufactured from any suitable material, e.g., polymers, metals, metal alloys, etc., or from any combination of suitable materials.

FIG. 4B illustrates a cross-sectional view of an assembled steerable laser probe 400. Illustratively, pressure mechanism 230 may be disposed over actuation guide 245, e.g., pressure mechanism distal end 231 may abut pressure mechanism distal interface 331. In one or more embodiments, pressure mechanism 230 may be configured to provide a force. Illustratively, pressure mechanism 230 may comprise a spring. Pressure mechanism 230 may be manufactured from any suitable material, e.g., polymers, metals, metal alloys, etc., or from any combination of suitable materials.

In one or more embodiments, housing sleeve 250 may be disposed within actuation guide 245, nosecone 240, and housing sleeve guide 340, e.g., housing sleeve distal end 251 may extend a distance from nosecone distal end 241. Illustratively, actuation guide 245 may be disposed within actuation mechanism 220 and piston tube 225, e.g., actuation mechanism proximal end 247 may extend a distance from piston tube proximal end 227. In one or more embodiments, actuation guide interface 223 may be configured to interface with actuation guide 245, e.g., when actuation guide 245 is disposed within actuation mechanism 220, actuation guide interface 223 may be contained within actuation channel 310. Illustratively, pressure mechanism 230 may be disposed between actuation mechanism 220 and pressure mechanism distal interface 331, e.g., pressure mechanism proximal end 232 may abut actuation mechanism distal end 221 and pressure mechanism distal end 231 may abut pressure mechanism distal interface 331.

In one or more embodiments, actuation guide 245 may be disposed within inner bore 140. Illustratively, piston tube 225 may be disposed within actuation structure 120. In one or more embodiments, a portion of actuation mechanism 220 may be disposed within actuation structure 120. Illustratively, optic fiber 270 and shape memory sleeve 260 may be disposed within inner bore 140, actuation guide inner bore 320, piston tube 225, actuation mechanism 220, housing sleeve guide 340, and housing sleeve 250. In one or more embodiments, fixation mechanism 210 may be configured to fix optic fiber 270, shape memory sleeve 260, and actuation guide 245 in a position relative to handle 100. For example, fixation mechanism 210 may comprise a set screw configured to fix optic fiber 270, shape memory sleeve 260, and actuation guide 245 in a position relative to handle 100, e.g., by an interference fit in actuation channel 310. In one or more embodiments, fixation mechanism 210 may comprise an adhesive material configured to fix optic fiber 270, shape memory sleeve 260, and actuation guide 245 in a position relative to handle 100, or fixation mechanism 210 may comprise one or more magnets configured to fix optic fiber 270, shape memory sleeve 260, and actuation guide 245 in a position relative to handle 100.

Illustratively, a compression of actuation structure 120 may be configured to extend a portion of actuation mechanism 220 out of actuation structure 120. For example, a compression of actuation structure 120 may be configured to extend actuation mechanism 220 relative to handle proximal end 102. In one or more embodiments, an application of a compressive force to one or more actuation arms 125 of actuation structure 120 may be configured to extend actuation mechanism 220 relative to handle proximal end 102, e.g., by advancing actuation mechanism 220 towards actuation mechanism distal interface 335. For example, a compression of actuation structure 120 may be configured to actuate actuation mechanism 220 along actuation mechanism guide 245. In one or more embodiments, a compression of actuation structure 120 may be configured to advance actuation guide interface 223 within actuation channel 310, e.g., away from actuation guide proximal end 247 and towards actuation mechanism distal interface 335. Illustratively, pressure mechanism 230 may be configured to provide a resistive force that resists an extension of actuation mechanism 220 relative to handle proximal end 102.

In one or more embodiments, an extension of actuation mechanism 220 away from handle proximal end 102 and towards actuation mechanism distal interface 335, e.g., due to a compression of actuation structure 120, may be configured to extend housing sleeve 250 relative to shape memory sleeve 260 and optic fiber 270. Illustratively, a compression of actuation structure 120 may be configured to actuate housing sleeve 250 relative to shape memory sleeve 260 and optic fiber 270 wherein housing sleeve 250 may be gradually extended over shape memory sleeve 260 and optic fiber 270. In one or more embodiments, shape memory sleeve 260 and optic fiber 270 may be gradually straightened as housing sleeve 250 is gradually extended over shape memory sleeve 260 and optic fiber 270.

Illustratively, a decompression of actuation structure 120 may be configured to retract a portion of actuation mechanism 220 into actuation structure 120. For example, a decompression of actuation structure 120 may be configured to retract actuation mechanism 220 relative to handle proximal end 102. In one or more embodiments, a reduction of a compressive force applied to one or more actuation arms 125 of actuation structure 120 may be configured to retract actuation mechanism 220 towards handle proximal end 102 and away from actuation mechanism distal interface 335. For example, a decompression of actuation structure 120 may be configured to actuate actuation mechanism 220 along actuation mechanism guide 245. In one or more embodiments, a decompression of actuation structure 120 may be configured to retract actuation guide interface 223 within actuation channel 310, e.g., towards actuation guide proximal end 247 and away from actuation mechanism distal interface 335. Illustratively, pressure mechanism 230 may be configured to provide a facilitating force that facilitates a retraction of actuation mechanism 220 relative to handle proximal end 102.

In one or more embodiments, a retraction of actuation mechanism 220 towards handle proximal end 102 and away from actuation mechanism distal interface 335, e.g., due to a decompression of actuation structure 120, may be configured to retract housing sleeve 250 relative to shape memory sleeve 260 and optic fiber 270. Illustratively, a decompression of actuation structure 120 may be configured to actuate housing sleeve 250 relative to shape memory sleeve 260 and optic fiber 270 wherein housing sleeve 250 may be gradually refracted and shape memory sleeve 260 and optic fiber 270 may be gradually exposed by housing sleeve 250. In one or more embodiments, shape memory sleeve 260 may be configured to gradually curve optic fiber 270, e.g., towards pre-bent angle 265, as shape memory sleeve 260 and optic fiber 270 are gradually exposed by housing sleeve 250.

Figure 5A:
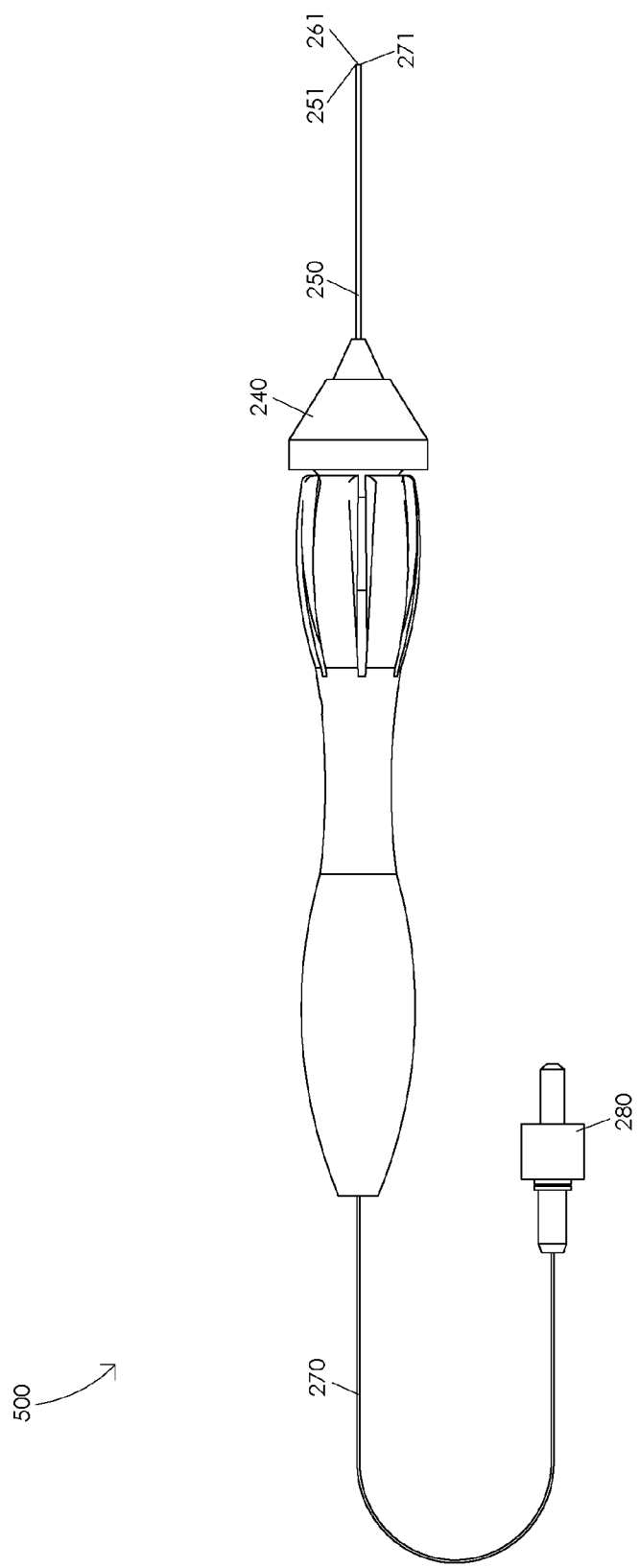
FIGS. 5A, 5B, and 5C are schematic diagrams illustrating a gradual curving of an optic fiber.
Figure 5B:
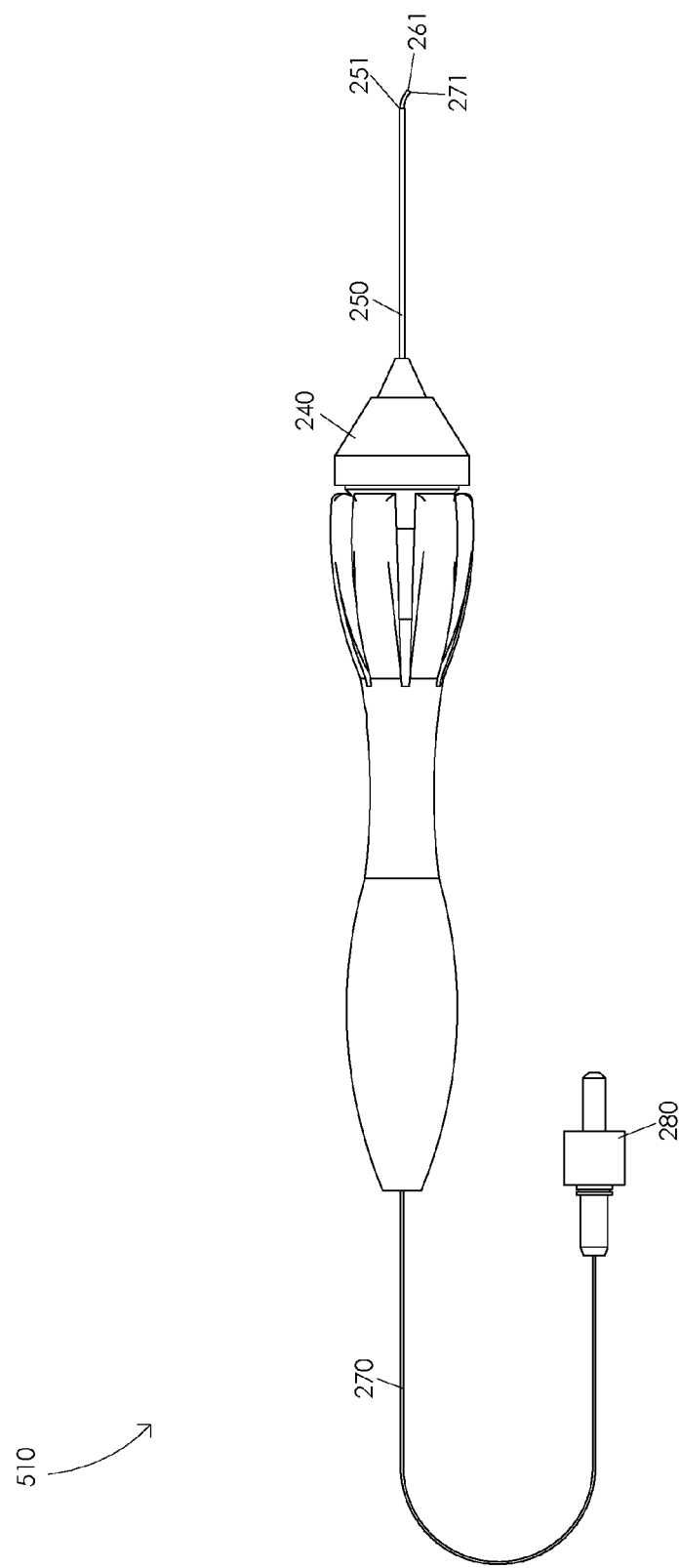
Figure 5C:
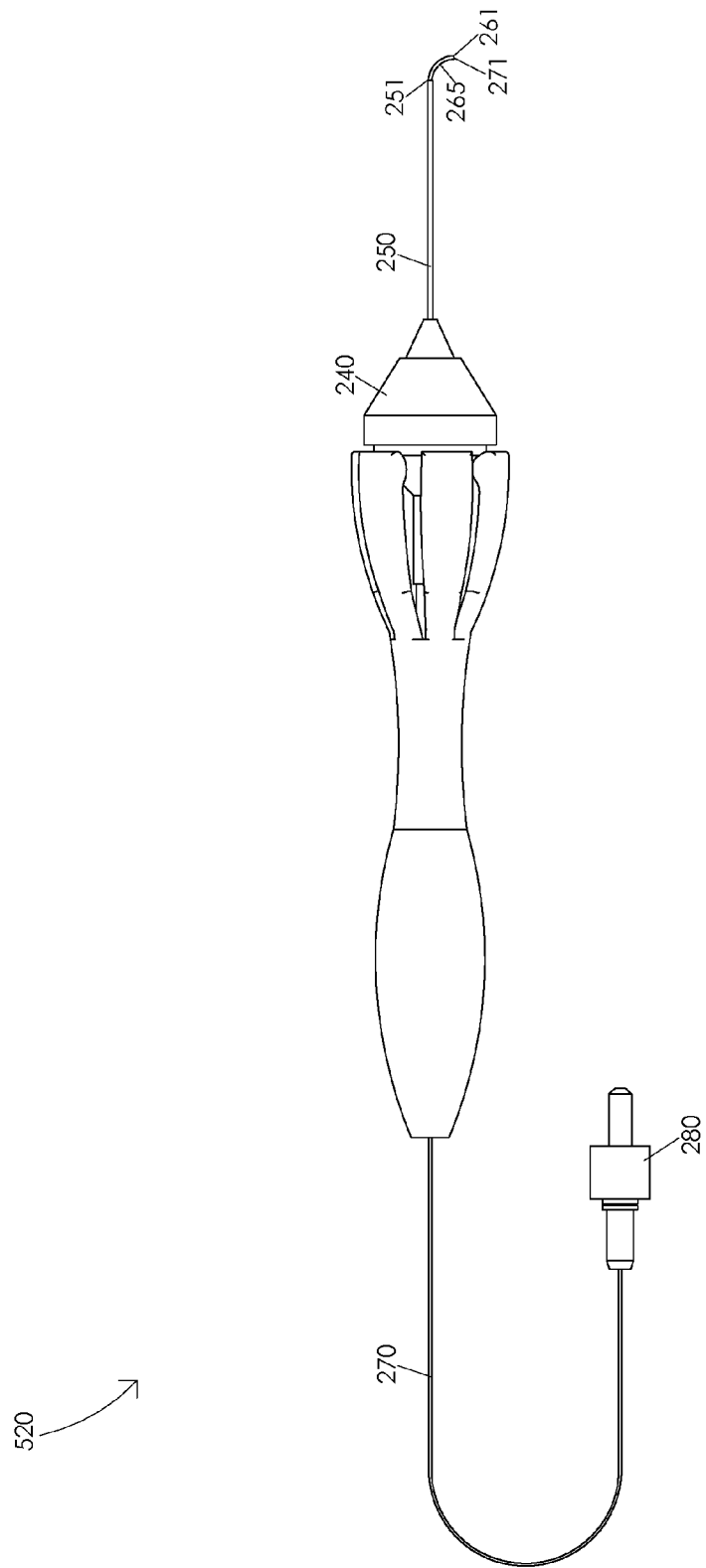

FIGS. 5A, 5B, and 5C are schematic diagrams illustrating a gradual curving of an optic fiber 270. FIG. 5A illustrates a straightened optic fiber 500. Illustratively, straightened optic fiber 500 may be fully contained within housing sleeve 250. In one or more embodiments, optic fiber 270 and shape memory sleeve 260 may be fully contained within housing sleeve 250, e.g., when actuation structure 120 is fully compressed. For example, actuation mechanism distal end 221 may abut actuation mechanism distal interface 335, e.g., when optic fiber 270 comprises a straightened optic fiber 500. Illustratively, when optic fiber 270 and shape memory sleeve 260 are fully contained within housing sleeve 250, pre-bent angle 265 of shape memory sleeve 260 may be straightened by housing sleeve 250. For example, an angle between housing sleeve 250 and a line tangent to optic fiber distal end 271 may be, e.g., 180 degrees, when housing sleeve 250 contains a straightened optic fiber 500.

FIG. 5B illustrates a partially curved optic fiber 510. In one or more embodiments, a decompression of a fully compressed actuation structure 120 may be configured to gradually retract housing sleeve 250, e.g., to expose optic fiber 270 and shape memory sleeve 260. Illustratively, as optic fiber 270 and shape memory sleeve 260 are gradually exposed by a retraction of housing sleeve 250, shape memory sleeve 260 may be configured to cause optic fiber 270 to gradually curve toward pre-bent angle 265. In one or more embodiments, a decompression of actuation structure 120 may be configured to cause a straightened optic fiber 500 to gradually curve to a partially curved optic fiber 510. Illustratively, a decompression of actuation structure 120 may be configured to gradually expose optic fiber 270 and shape memory sleeve 260 causing optic fiber 270 to gradually curve toward pre-bent angle 265. For example, as an exposed length of optic fiber 270 and shape memory sleeve 260 is increased, e.g., by a retraction of housing sleeve 250, an angle between housing sleeve 250 and a line tangent to optic fiber distal end 271 may be decreased.

Illustratively, optic fiber 270 and shape memory sleeve 260 may be exposed from housing sleeve distal end 251 at a first exposed length with a first angle between housing sleeve 250 and a line tangent to optic fiber distal end 271. A refraction of housing sleeve 250, e.g., due to a decompression of actuation structure 120, may be configured to expose optic fiber 270 and shape memory sleeve 260 from housing sleeve distal end 251 at a second exposed length with a second angle between housing sleeve 250 and a line tangent to optic fiber distal end 271. Illustratively, the second exposed length may be greater than the first exposed length and the second angle may be less than the first angle.

FIG. 5C illustrates a fully curved optic fiber 520. Illustratively, when housing sleeve 250 is fully retracted, e.g., by a full decompression of actuation structure 120, housing sleeve 250 may expose a fully curved optic fiber 520. In one or more embodiments, a decompression of actuation structure 120 may be configured to cause a partially curved optic fiber 510 to gradually curve to a fully curved optic fiber 520.

Illustratively, when housing sleeve 250 is retracted to expose a partially curved optic fiber 510, optic fiber 270 and shape memory sleeve 260 may be exposed from housing sleeve distal end 251 at a partially exposed length with a partially exposed angle between housing sleeve 250 and a line tangent to optic fiber distal end 271. A retraction of housing sleeve 250, e.g., due to a full decompression of actuation structure 120, may be configured to expose optic fiber 270 and shape memory sleeve 260 from housing sleeve distal end 251 at fully exposed length with a fully exposed angle between housing sleeve 250 and a line tangent to optic fiber distal end 271. For example, housing sleeve 250 may expose optic fiber 270 and shape memory sleeve 260 at a fully exposed length with a fully exposed angle between housing sleeve 250 and a line tangent to optic fiber distal end 271 when housing sleeve 250 is retracted to expose a fully curved optic fiber 520. Illustratively, the fully exposed length may be greater than the partially exposed length and the fully exposed angle may be less than the partially exposed angle.

In one or more embodiments, one or more properties of a steerable laser probe may be adjusted to attain one or more desired steerable laser probe features. Illustratively, a position of fixation mechanism housing 150 and fixation mechanism 210 or a length of optic fiber 270 and shape memory sleeve 260 extending distally from a position of fixation mechanism 210 may be adjusted to vary an amount of decompression of actuation structure 120 configured to expose a particular length of optic fiber 270 and shape memory sleeve 260 from housing sleeve distal end 251. In one or more embodiments, one or more properties of pressure mechanism 230 may be adjusted to attain one or more desired steerable laser probe features. Illustratively, a spring constant of pressure mechanism 230 may be adjusted to vary an amount of decompression of actuation structure 120 configured to expose a particular length of optic fiber 270 and shape memory sleeve 260 from housing sleeve distal end 251. In one or more embodiments, a geometry of actuation mechanism 220 may be adjusted to vary an amount of decompression of actuation structure 120 configured to expose a particular length of optic fiber 270 and shape memory sleeve 260 from housing sleeve distal end 251. Illustratively, a length of housing sleeve 250 may be adjusted to vary an amount of decompression of actuation structure 120 configured to expose a particular length of optic fiber 270 and shape memory sleeve 260 from housing sleeve distal end 251. In one or more embodiments, a geometry of actuation structure 120 may be adjusted to vary an amount of decompression of actuation structure 120 configured to expose a particular length of optic fiber 270 and shape memory sleeve 260 from housing sleeve distal end 251. Illustratively, a magnitude of pre-bent angle 265 may be adjusted to vary a magnitude of an angle between housing sleeve 250 and a line tangent to optic fiber distal end 271 when a particular length of optic fiber 270 and shape memory sleeve 260 is exposed from housing sleeve distal end 251.

In one or more embodiments, one or more properties of optic fiber 270 may be adjusted to attain one or more steerable laser probe features. For example, a portion of optic fiber 270 may be formed in a pre-bent angle. Illustratively, a portion of optic fiber 270 may be formed in a pre-bent angle by, e.g., heating the portion of optic fiber 270 to a temperature configured to weaken chemical bonds of the portion of optic fiber 270, molding the portion of optic fiber 270 in a pre-bent angle, and cooling the portion of optic fiber 270. In one or more embodiments, optic fiber 270 may be coated by a buffer material. Illustratively, the buffer material may comprise a fluoropolymer, e.g., Teflon, Tefzel, etc. In one or more embodiments, a portion of optic fiber 270 may be formed in a pre-bent angle by, e.g., heating the buffer material to a temperature configured to weaken chemical bonds of the buffer material, molding the portion of optic fiber 270 in a pre-bent angle, and cooling the buffer material. Illustratively, housing sleeve 250 may be configured to hold a pre-bent angle of optic fiber 270 in a straightened position, e.g., when optic fiber 270 is fully contained within housing sleeve 250. In one or more embodiments, a decompression of actuation structure 120 may be configured to retract housing sleeve 250 relative to optic fiber 270 causing optic fiber 270 to gradually curve towards the pre-bent angle as optic fiber 270 is gradually exposed by housing sleeve 250.

Figure 6A:
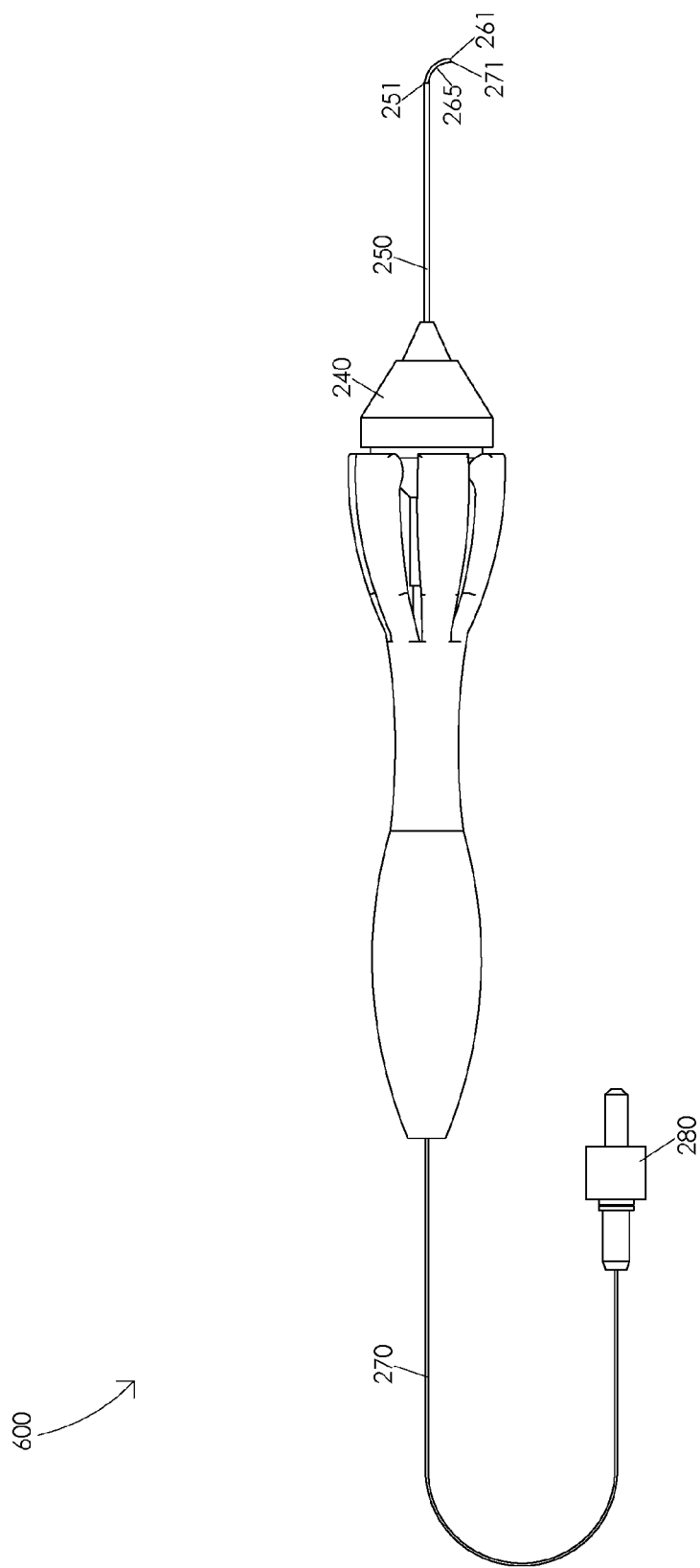
Figure 6B:
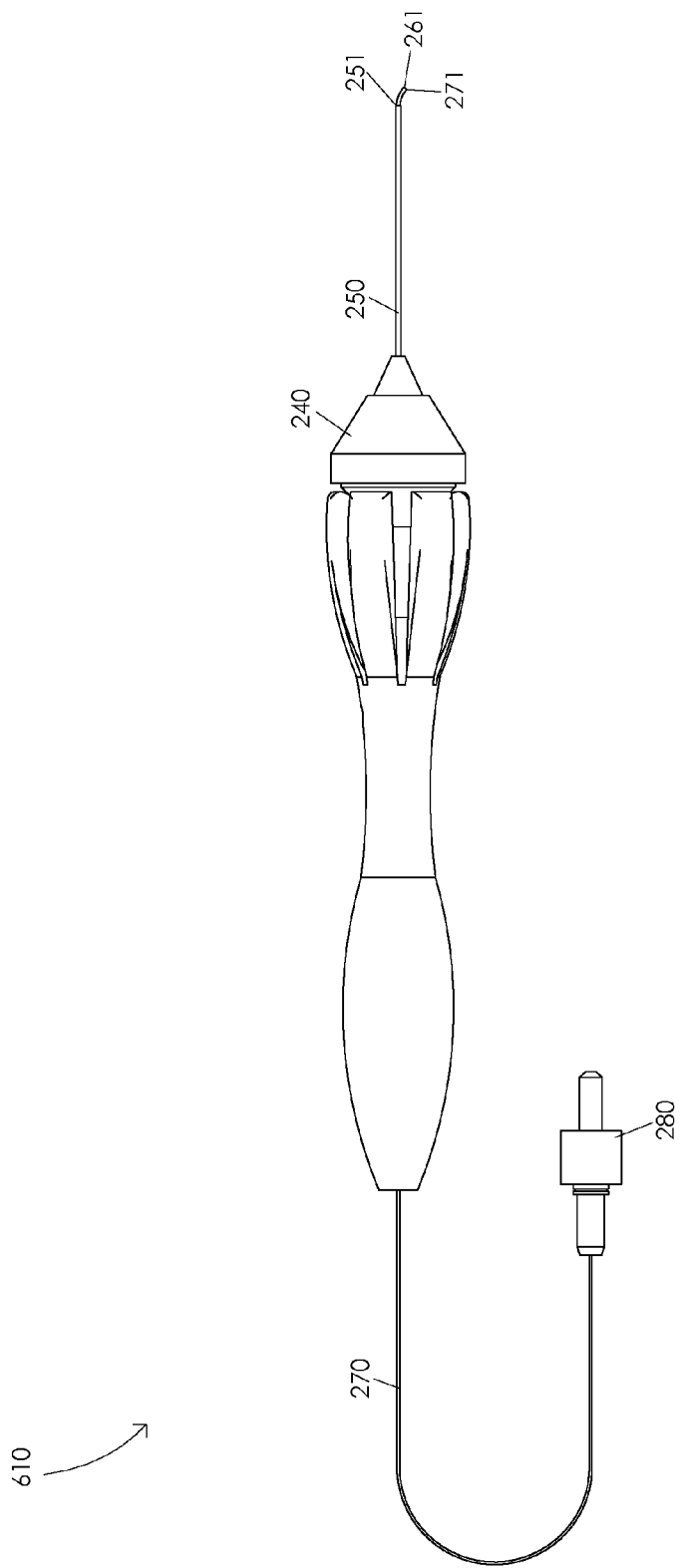

FIGS. 6A, 6B, and 6C are schematic diagrams illustrating a gradual straightening of an optic fiber 270. FIG. 6A illustrates a retracted housing sleeve 600. Illustratively, a refracted housing sleeve 600 may expose at least a portion of optic fiber 270 and shape memory sleeve 260 from housing sleeve distal end 251. In one or more embodiments, a full decompression of actuation structure 120 may be configured to cause housing sleeve 250 to be retracted relative to optic fiber 270 and shape memory sleeve 260 wherein a fully curved optic fiber 520 may be exposed from housing sleeve distal end 251. Illustratively, housing sleeve 250 may comprise a retracted housing sleeve 600, e.g., due to a full decompression of actuation structure 120.

FIG. 6B illustrates a partially extended housing sleeve 610. Illustratively, a partially extended housing sleeve 610 may hold a portion of pre-bent angle 265 in a straightened position within housing sleeve 250. In one or more embodiments, a compression of actuation structure 120 may be configured to extend housing sleeve 250 over optic fiber 270 and shape memory sleeve 260 causing shape memory sleeve 260 to gradually straighten optic fiber 270 from a fully curved optic fiber 520 to a partially curved optic fiber 510.

FIG. 6C illustrates a fully extended housing sleeve 620. Illustratively, a fully extended housing sleeve 620 may hold pre-bent angle 265 in a straightened position within housing sleeve 250. In one or more embodiments, a full compression of actuation structure 120 may be configured to extend housing sleeve 250 over optic fiber 270 and shape memory sleeve 260 causing shape memory sleeve 260 to gradually straighten optic fiber 270 from a partially curved optic fiber 510 to a straightened optic fiber 500.

Illustratively, a surgeon may aim optic fiber distal end 271 at any of a plurality of targets within an eye, e.g., to perform a photocoagulation procedure. In one or more embodiments, a surgeon may aim optic fiber distal end 271 at any target within a particular transverse plane of the inner eye by, e.g., rotating handle 100 to orient shape memory sleeve 260 in an orientation configured to cause a curvature of optic fiber 270 within the particular transverse plane of the inner eye and varying an amount of compression of actuation structure 120. Illustratively, a surgeon may aim optic fiber distal end 271 at any target within a particular sagittal plane of the inner eye by, e.g., rotating handle 100 to orient shape memory sleeve 260 in an orientation configured to cause a curvature of optic fiber 270 within the particular sagittal plane of the inner eye and varying an amount of compression of actuation structure 120. In one or more embodiments, a surgeon may aim optic fiber distal end 271 at any target within a particular frontal plane of the inner eye by, e.g., varying an amount of compression of actuation structure 120 to orient a line tangent to optic fiber distal end 271 wherein the line tangent to optic fiber distal end 271 is within the particular frontal plane of the inner eye and rotating handle 100. Illustratively, a surgeon may aim optic fiber distal end 271 at any target located outside of the particular transverse plane, the particular sagittal plane, and the particular frontal plane of the inner eye, e.g., by varying a rotational orientation of handle 100 and varying an amount of compression of actuation structure 120.

FIGS. 7A and 7B are schematic diagrams illustrating a handle 700. FIG. 7A illustrates a top view of handle 700. In one or more embodiments, handle 700 may comprise a handle distal end 701, a handle proximal end 702, a handle base 710, and an actuation structure 720. Illustratively, actuation structure 720 may comprise a plurality of actuation arms 725. In one or more embodiments, actuation structure 720 may comprise a shape memory material. Actuation structure 720 may be manufactured from any suitable material, e.g., polymers, metals, metal alloys, etc., or from any combination of suitable materials.

Illustratively, actuation structure 720 may be compressed by an application of a compressive force to actuation structure 720. In one or more embodiments, actuation structure 720 may be compressed by an application of one or more compressive forces located at one or more locations around an outer perimeter of actuation structure 720. Illustratively, the one or more locations may comprise any of a plurality of locations around the outer perimeter of actuation structure 720. For example, a surgeon may compress actuation structure 720 by squeezing actuation structure 720. Illustratively, the surgeon may compress actuation structure 720 by squeezing actuation structure 720 at any particular location of a plurality of locations around an outer perimeter of actuation structure 720. For example, a surgeon may rotate handle 700 and compress actuation structure 720 from any rotational position of a plurality of rotational positions of handle 700.

In one or more embodiments, actuation structure 720 may be compressed by an application of a compressive force to any one or more of the plurality of actuation arms 725. Illustratively, each actuation arm 725 may be configured to actuate independently. In one or more embodiments, each actuation arm 725 may be connected to one or more of the plurality of actuation arms 725 wherein an actuation of a particular actuation arm 725 may be configured to actuate every actuation arm 725 of the plurality of actuation arms 725. In one or more embodiments, a compression of actuation structure 720, e.g., due to an application of a compressive force to a particular actuation arm 725, may be configured to actuate the particular actuation arm 725. Illustratively, an actuation of the particular actuation arm 725 may be configured to actuate every actuation arm 725 of the plurality of actuation arms 725.

FIG. 7B illustrates a cross-sectional view of handle 700. In one or more embodiments, handle 700 may comprise an inner bore 740 and a fixation mechanism housing 750. Handle 700 may be manufactured from any suitable material, e.g., polymers, metals, metal alloys, etc., or from any combination of suitable materials.

Figure 8:
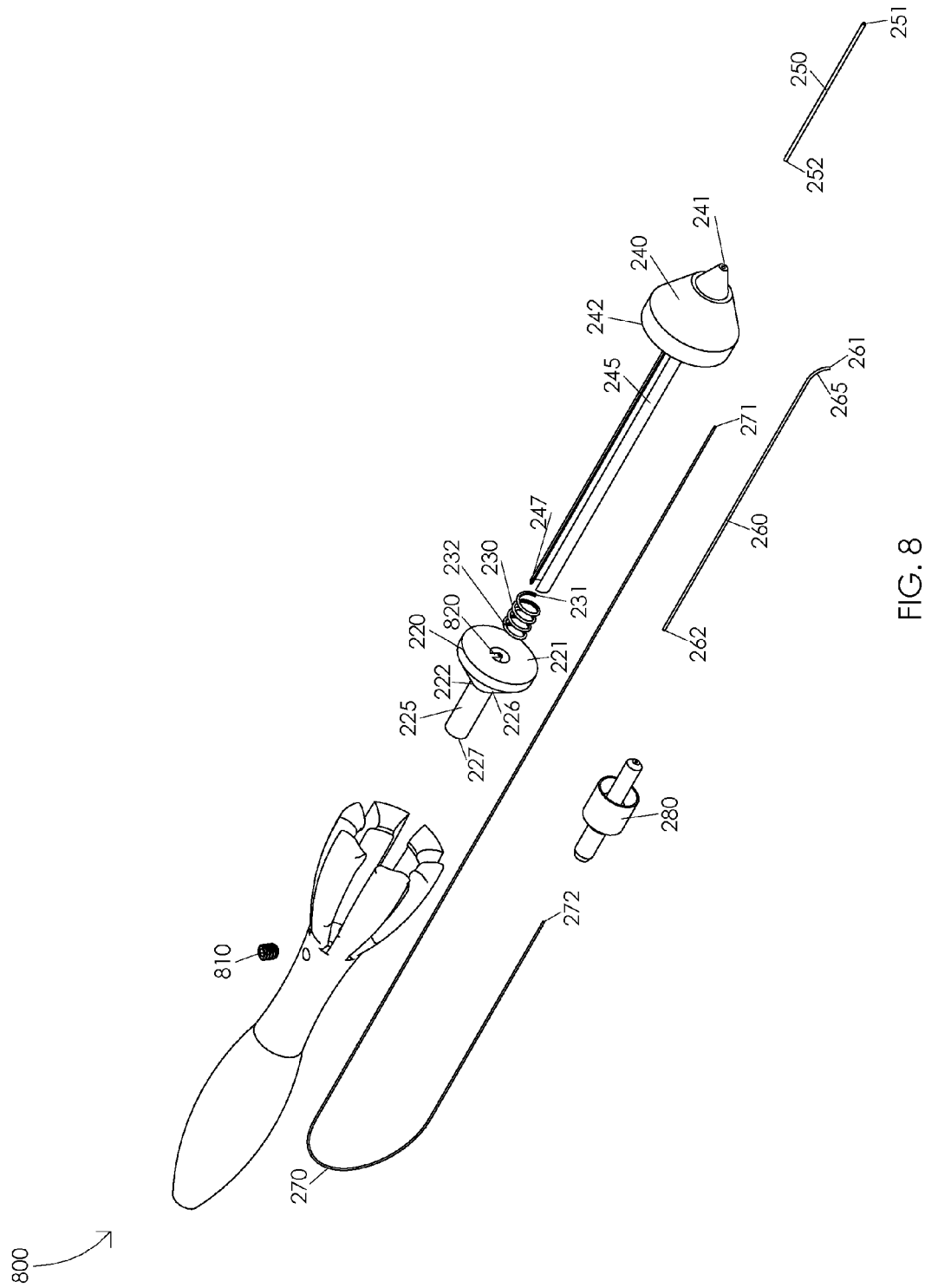
FIG. 8 illustrates an exploded view of a steerable laser probe assembly.

FIG. 8 illustrates an exploded view of a steerable laser probe assembly 800. In one or more embodiments, steerable laser probe assembly 800 may comprise a handle 700, a fixation mechanism 810, an actuation mechanism 220 having an actuation mechanism distal end 221 and an actuation mechanism proximal end 222, a piston tube 225 having a piston tube distal end 226 and a piston tube proximal end 227, a pressure mechanism 230 having a pressure mechanism distal end 231 and a pressure mechanism proximal end 232, a nosecone 240 having a nosecone distal end 241 and a nosecone proximal end 242, an actuation guide 245 having an actuation guide proximal end 247, a housing sleeve 250 having a housing sleeve distal end 251 and a housing sleeve proximal end 252, a shape memory sleeve 260 having a shape memory sleeve distal end 261 and a shape memory sleeve proximal end 262, an optic fiber 270 having an optic fiber distal end 271 and an optic fiber proximal end 272, and a light source interface 280. Illustratively, light source interface 280 may be configured to interface with optic fiber proximal end 272. In one or more embodiments, light source interface 280 may comprise a standard light source connecter, e.g., an SMA connector.

Illustratively, actuation mechanism 220 may comprise an actuation guide interface 820 configured to interface with actuation guide 245. In one or more embodiments, piston tube 225 may be fixed to actuation mechanism proximal end 222. Illustratively, actuation mechanism 220 and piston tube 225 may be manufactured as a unit. In one or more embodiments, housing tube proximal end 252 may be fixed to nosecone proximal end 241. Illustratively, actuation guide 245 may be fixed an inner portion of nosecone 240. In one or more embodiments, actuation guide 245, nosecone 240, and housing sleeve 250 may be manufactured as a unit.

FIGS. 9A and 9B are schematic diagrams illustrating an assembled steerable laser probe 900. FIG. 9A illustrates a side view of an assembled steerable laser probe 900. Illustratively, optic fiber 270 may be disposed within shape memory sleeve 260, e.g., optic fiber distal end 271 may be adjacent to shape memory sleeve distal end 261. Optic fiber 270 may be fixed in a position within shape memory sleeve 260, e.g., by a biocompatible adhesive or any other suitable fixation means. In one or more embodiments, shape memory sleeve 260 may comprise a pre-bent angle 265 configured to curve optic fiber 270 towards pre-bent angle 265. Illustratively, shape memory sleeve 260 may comprise a shape memory material, e.g., nitinol, configured to steer optic fiber 270 towards one or more surgical targets within an eye. Shape memory sleeve 260 may be manufactured from any suitable material, e.g., polymers, metals, metal alloys, etc., or from any combination of suitable materials.

FIG. 9B illustrates a cross-sectional view of an assembled steerable laser probe 900. Illustratively, pressure mechanism 230 may be disposed over actuation guide 245, e.g., pressure mechanism distal end 231 may abut pressure mechanism distal interface 331. In one or more embodiments, pressure mechanism 230 may be configured to provide a force. Illustratively, pressure mechanism 230 may comprise a spring. Pressure mechanism 230 may be manufactured from any suitable material, e.g., polymers, metals, metal alloys, etc., or from any combination of suitable materials.

Illustratively, actuation guide 245 may be disposed within actuation mechanism 220 and piston tube 225, e.g., actuation mechanism proximal end 247 may extend a distance from piston tube proximal end 227. In one or more embodiments, actuation guide interface 820 may be configured to interface with actuation guide 245, e.g., when actuation guide 245 is disposed within actuation mechanism 220, actuation guide interface 820 may be contained within actuation channel 310. Illustratively, pressure mechanism 230 may be disposed between actuation mechanism 220 and pressure mechanism distal interface 331, e.g., pressure mechanism proximal end 232 may abut actuation mechanism distal end 221 and pressure mechanism distal end 231 may abut pressure mechanism distal interface 331.

In one or more embodiments, actuation guide 245 may be disposed within inner bore 740. Illustratively, piston tube 225 may be disposed within actuation structure 720. In one or more embodiments, a portion of actuation mechanism 220 may be disposed within actuation structure 720. Illustratively, optic fiber 270 and shape memory sleeve 260 may be disposed within inner bore 740, actuation guide inner bore 320, piston tube 225, actuation mechanism 220, housing sleeve guide 340, and housing sleeve 250. In one or more embodiments, optic fiber 270 and shape memory sleeve 260 may be fixed to an inner portion of actuation mechanism 220. For example, shape memory sleeve 260 may be fixed within actuation mechanism 220 by an adhesive or by any suitable fixation means. Illustratively, an actuation of actuation mechanism 220 may be configured to actuate optic fiber 270 and shape memory sleeve 260.

In one or more embodiments, fixation mechanism 810 may be configured to fix actuation guide 245 in a position relative to handle 700. For example, fixation mechanism 810 may comprise a set screw configured to fix actuation guide 245 in a position relative to handle 700, e.g., by an interference fit in actuation channel 310. In one or more embodiments, fixation mechanism 810 may comprise an adhesive material configured to fix actuation guide 245 in a position relative to handle 700, or fixation mechanism 810 may comprise one or more magnets configured to fix actuation guide 245 in a position relative to handle 700.

Illustratively, a compression of actuation structure 720 may be configured to extend a portion of actuation mechanism 220 out of actuation structure 720. For example, a compression of actuation structure 720 may be configured to extend actuation mechanism 220 relative to handle proximal end 702. In one or more embodiments, an application of a compressive force to one or more actuation arms 725 of actuation structure 720 may be configured to extend actuation mechanism 220 relative to handle proximal end 702, e.g., by advancing actuation mechanism 220 towards actuation mechanism distal interface 335. For example, a compression of actuation structure 720 may be configured to actuate actuation mechanism 220 along actuation mechanism guide 245. In one or more embodiments, a compression of actuation structure 720 may be configured to advance actuation guide interface 820 within actuation channel 310, e.g., away from actuation guide proximal end 247 and towards actuation mechanism distal interface 335. Illustratively, pressure mechanism 230 may be configured to provide a resistive force that resists an extension of actuation mechanism 220 relative to handle proximal end 702.

In one or more embodiments, an extension of actuation mechanism 220 away from handle proximal end 702 and towards actuation mechanism distal interface 335, e.g., due to a compression of actuation structure 720, may be configured to extend shape memory sleeve 260 and optic fiber 270 relative to housing sleeve 250. Illustratively, a compression of actuation structure 720 may be configured to actuate shape memory sleeve 260 and optic fiber 270 relative to housing sleeve 250 wherein shape memory sleeve 260 and optic fiber 270 may be gradually extended from housing sleeve 250. For example, a compression of actuation structure 720 may be configured to gradually extend shape memory sleeve 260 and optic fiber 270 from housing sleeve distal end 251. In one or more embodiments, shape memory sleeve 260 may be configured to gradually curve optic fiber 270, e.g., towards pre-bent angle 265, as shape memory sleeve 260 and optic fiber 270 are gradually extended from housing sleeve distal end 251.

Illustratively, a decompression of actuation structure 720 may be configured to retract a portion of actuation mechanism 220 into actuation structure 720. For example, a decompression of actuation structure 720 may be configured to retract actuation mechanism 220 relative to handle proximal end 702. In one or more embodiments, a reduction of a compressive force applied to one or more actuation arms 725 of actuation structure 720 may be configured to retract actuation mechanism 220 towards handle proximal end 702 and away from actuation mechanism distal interface 335. For example, a decompression of actuation structure 720 may be configured to actuate actuation mechanism 220 along actuation mechanism guide 245. In one or more embodiments, a decompression of actuation structure 720 may be configured to retract actuation guide interface 820 within actuation channel 310, e.g., towards actuation guide proximal end 247 and away from actuation mechanism distal interface 335. Illustratively, pressure mechanism 230 may be configured to provide a facilitating force that facilitates a retraction of actuation mechanism 220 relative to handle proximal end 702.

In one or more embodiments, a retraction of actuation mechanism 220 towards handle proximal end 702 and away from actuation mechanism distal interface 335, e.g., due to a decompression of actuation structure 720, may be configured to retract shape memory sleeve 260 and optic fiber 270 relative to housing sleeve 250. Illustratively, a decompression of actuation structure 720 may be configured to actuate shape memory sleeve 260 and optic fiber 270 relative to housing sleeve 250 wherein shape memory sleeve 260 and optic fiber 270 may be gradually retracted into housing sleeve 250. For example, a decompression of actuation structure 720 may be configured to retract shape memory sleeve 260 and optic fiber 270 into housing sleeve distal end 251. In one or more embodiments, shape memory sleeve 260 and optic fiber 270 may be gradually straightened as shape memory sleeve 260 and optic fiber 270 are gradually retracted into housing sleeve 250.

Figure 10A:
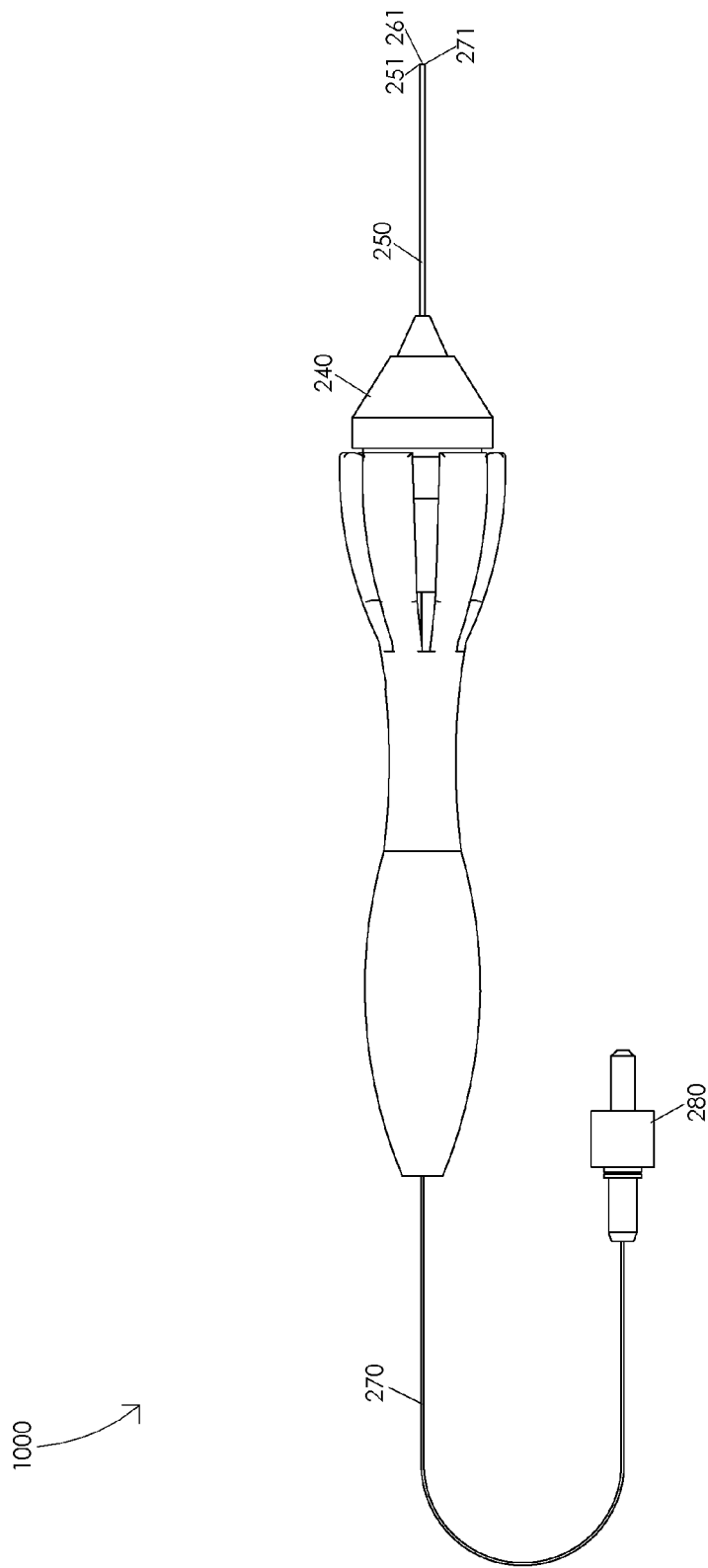
Figure 10B:
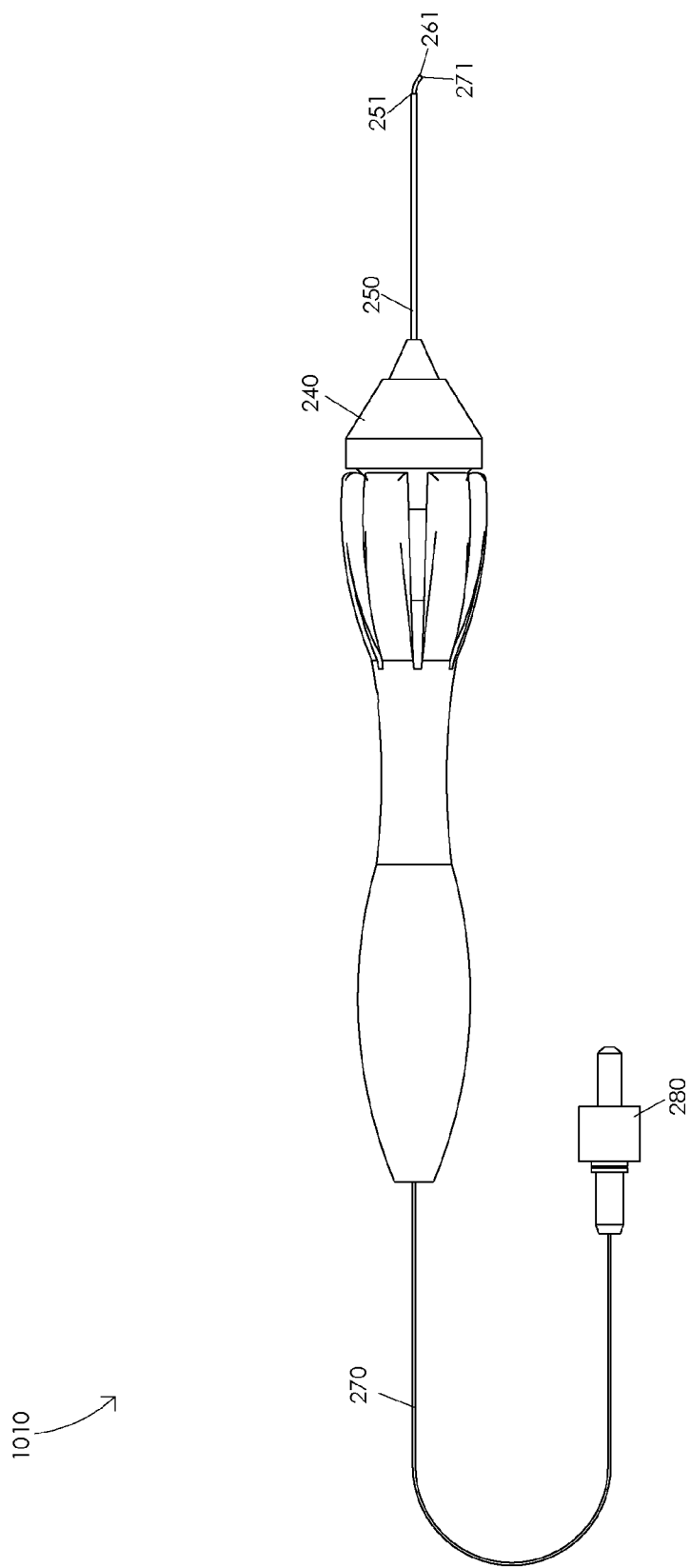

FIGS. 10A, 10B, and 10C are schematic diagrams illustrating a gradual curving of an optic fiber 270. FIG. 10A illustrates a straightened optic fiber 1000. Illustratively, straightened optic fiber 1000 may be fully contained within housing sleeve 250. In one or more embodiments, optic fiber 270 and shape memory sleeve 260 may be fully contained within housing sleeve 250, e.g., when actuation structure 720 is fully decompressed. For example, actuation mechanism 220 may be fully retracted, e.g., when optic fiber 270 comprises a straightened optic fiber 1000. Illustratively, when optic fiber 270 and shape memory sleeve 260 are fully contained within housing sleeve 250, pre-bent angle 265 of shape memory sleeve 260 may be straightened by housing sleeve 250. For example, an angle between housing sleeve 250 and a line tangent to optic fiber distal end 271 may be, e.g., 180 degrees, when housing sleeve 250 contains a straightened optic fiber 1000.

FIG. 10B illustrates a partially curved optic fiber 1010. In one or more embodiments, a compression of a fully decompressed actuation structure 720 may be configured to gradually extend optic fiber 270 and shape memory sleeve 260 from housing sleeve distal end 251. Illustratively, as optic fiber 270 and shape memory sleeve 260 are gradually extended from housing sleeve distal end 251, shape memory sleeve 260 may be configured to cause optic fiber 270 to gradually curve toward pre-bent angle 265. In one or more embodiments, a compression of actuation structure 720 may be configured to cause a straightened optic fiber 1000 to gradually curve to a partially curved optic fiber 1010. Illustratively, a compression of actuation structure 720 may be configured to gradually extend optic fiber 270 and shape memory sleeve 260 from housing sleeve 250 causing optic fiber 270 to gradually curve toward pre-bent angle 265. For example, as an extended length of optic fiber 270 and shape memory sleeve 260 is increased, e.g., by an extension of optic fiber 270 and shape memory sleeve 260 from housing sleeve distal end 251, an angle between housing sleeve 250 and a line tangent to optic fiber distal end 271 may be decreased.

Illustratively, optic fiber 270 and shape memory sleeve 260 may be extended from housing sleeve distal end 251 at a first extended length with a first angle between housing sleeve 250 and a line tangent to optic fiber distal end 271. An extension of optic fiber 270 and shape memory sleeve 260 from housing sleeve 250, e.g., due to a compression of actuation structure 720, may be configured to extend optic fiber 270 and shape memory sleeve 260 from housing sleeve distal end 251 at a second extended length with a second angle between housing sleeve 250 and a line tangent to optic fiber distal end 271. Illustratively, the second extended length may be greater than the first extended length and the second angle may be less than the first angle.

FIG. 10C illustrates a fully curved optic fiber 1020. Illustratively, when optic fiber 270 and shape memory sleeve 260 are fully extended from housing sleeve 250, e.g., by a full compression of actuation structure 720, optic fiber 270 may comprise a fully curved optic fiber 1020. In one or more embodiments, a compression of actuation structure 720 may be configured to cause a partially curved optic fiber 1010 to gradually curve to a fully curved optic fiber 1020.

Illustratively, when optic fiber 270 and shape memory sleeve 260 are extended from housing sleeve 250 wherein optic fiber may comprise a partially curved optic fiber 1010, optic fiber 270 and shape memory sleeve 260 may be extended from housing sleeve distal end 251 at a partially extended length with a partially extended angle between housing sleeve 250 and a line tangent to optic fiber distal end 271. An extension of optic fiber 270 and shape memory sleeve 260 from housing sleeve 250, e.g., due to a full compression of actuation structure 720, may be configured to extend optic fiber 270 and shape memory sleeve 260 from housing sleeve distal end 251 at fully extended length with a fully extended angle between housing sleeve 250 and a line tangent to optic fiber distal end 271. For example, optic fiber 270 and shape memory sleeve 260 may be extended from housing sleeve distal end 251 at a fully extended length with a fully extended angle between housing sleeve 250 and a line tangent to optic fiber distal end 271 when optic fiber 270 comprises a fully curved optic fiber 1020. Illustratively, the fully extended length may be greater than the partially extended length and the fully extended angle may be less than the partially extended angle.

In one or more embodiments, one or more properties of a steerable laser probe may be adjusted to attain one or more desired steerable laser probe features. Illustratively, a position of fixation mechanism housing 750 and fixation mechanism 810 or a length of optic fiber 270 and shape memory sleeve 260 extending distally from a position of fixation mechanism 810 may be adjusted to vary an amount of compression of actuation structure 720 configured to extend a particular length of optic fiber 270 and shape memory sleeve 260 from housing sleeve distal end 251. In one or more embodiments, one or more properties of pressure mechanism 230 may be adjusted to attain one or more desired steerable laser probe features. Illustratively, a spring constant of pressure mechanism 230 may be adjusted to vary an amount of compression of actuation structure 720 configured to extend a particular length of optic fiber 270 and shape memory sleeve 260 from housing sleeve distal end 251. In one or more embodiments, a geometry of actuation mechanism 220 may be adjusted to vary an amount of compression of actuation structure 720 configured to extend a particular length of optic fiber 270 and shape memory sleeve 260 from housing sleeve distal end 251. Illustratively, a length of housing sleeve 250 may be adjusted to vary an amount of compression of actuation structure 720 configured to extend a particular length of optic fiber 270 and shape memory sleeve 260 from housing sleeve distal end 251. In one or more embodiments, a geometry of actuation structure 720 may be adjusted to vary an amount of compression of actuation structure 720 configured to extend a particular length of optic fiber 270 and shape memory sleeve 260 from housing sleeve distal end 251. Illustratively, a magnitude of pre-bent angle 265 may be adjusted to vary a magnitude of an angle between housing sleeve 250 and a line tangent to optic fiber distal end 271 when a particular length of optic fiber 270 and shape memory sleeve 260 is extended from housing sleeve distal end 251.

In one or more embodiments, one or more properties of optic fiber 270 may be adjusted to attain one or more steerable laser probe features. For example, a portion of optic fiber 270 may be formed in a pre-bent angle. Illustratively, a portion of optic fiber 270 may be formed in a pre-bent angle by, e.g., heating the portion of optic fiber 270 to a temperature configured to weaken chemical bonds of the portion of optic fiber 270, molding the portion of optic fiber 270 in a pre-bent angle, and cooling the portion of optic fiber 270. In one or more embodiments, optic fiber 270 may be coated by a buffer material. Illustratively, the buffer material may comprise a fluoropolymer, e.g., Teflon, Tefzel, etc. In one or more embodiments, a portion of optic fiber 270 may be formed in a pre-bent angle by, e.g., heating the buffer material to a temperature configured to weaken chemical bonds of the buffer material, molding the portion of optic fiber 270 in a pre-bent angle, and cooling the buffer material. Illustratively, housing sleeve 250 may be configured to hold a pre-bent angle of optic fiber 270 in a straightened position, e.g., when optic fiber 270 is fully contained within housing sleeve 250. In one or more embodiments, a compression of actuation structure 720 may be configured to extend optic fiber 270 relative to housing sleeve 250 causing optic fiber 270 to gradually curve towards the pre-bent angle as optic fiber 270 is gradually extended from housing sleeve distal end 251.

Figure 11A:
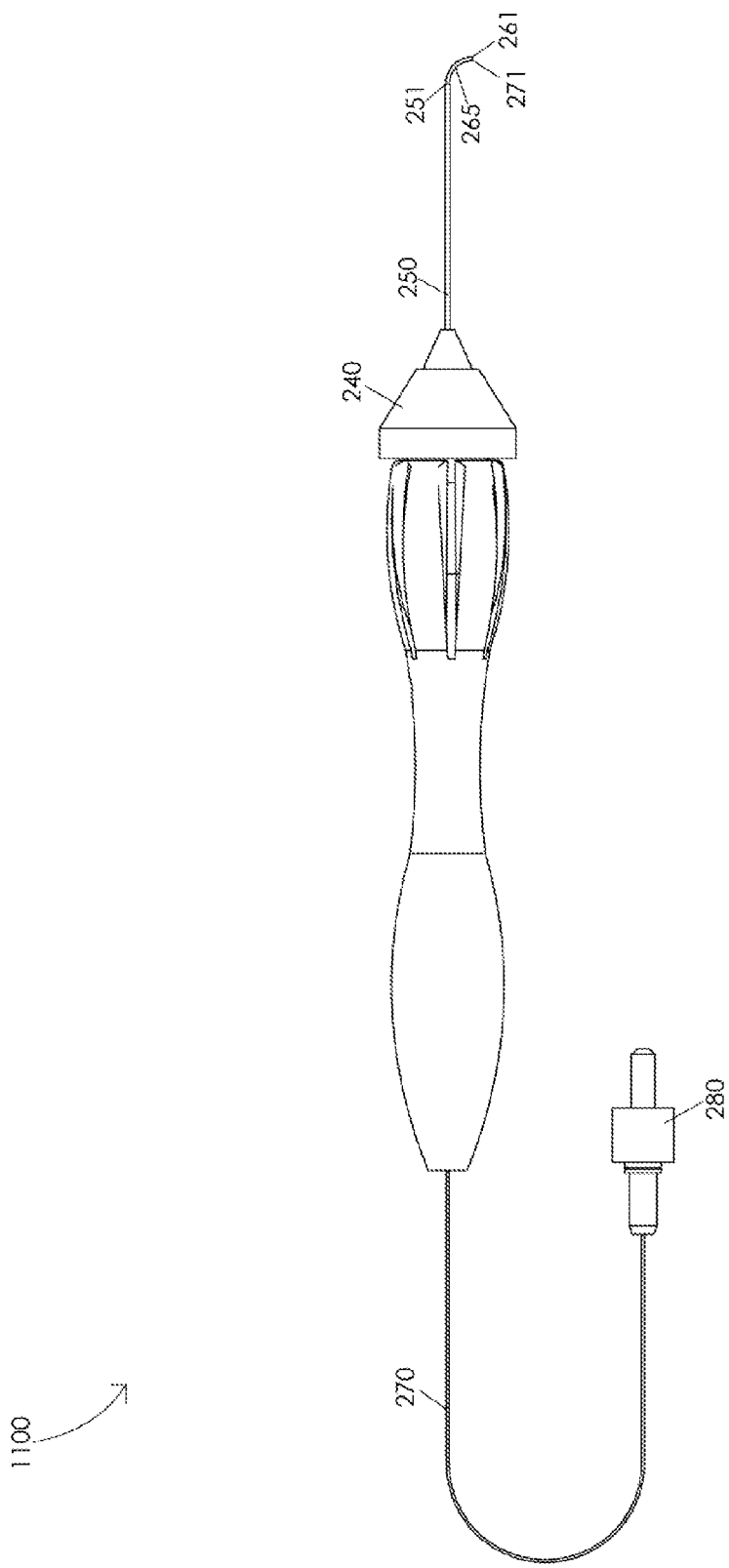
FIGS. 11A, 11B, and 11C are schematic diagrams illustrating a gradual straightening of an optic fiber.
Figure 11B:
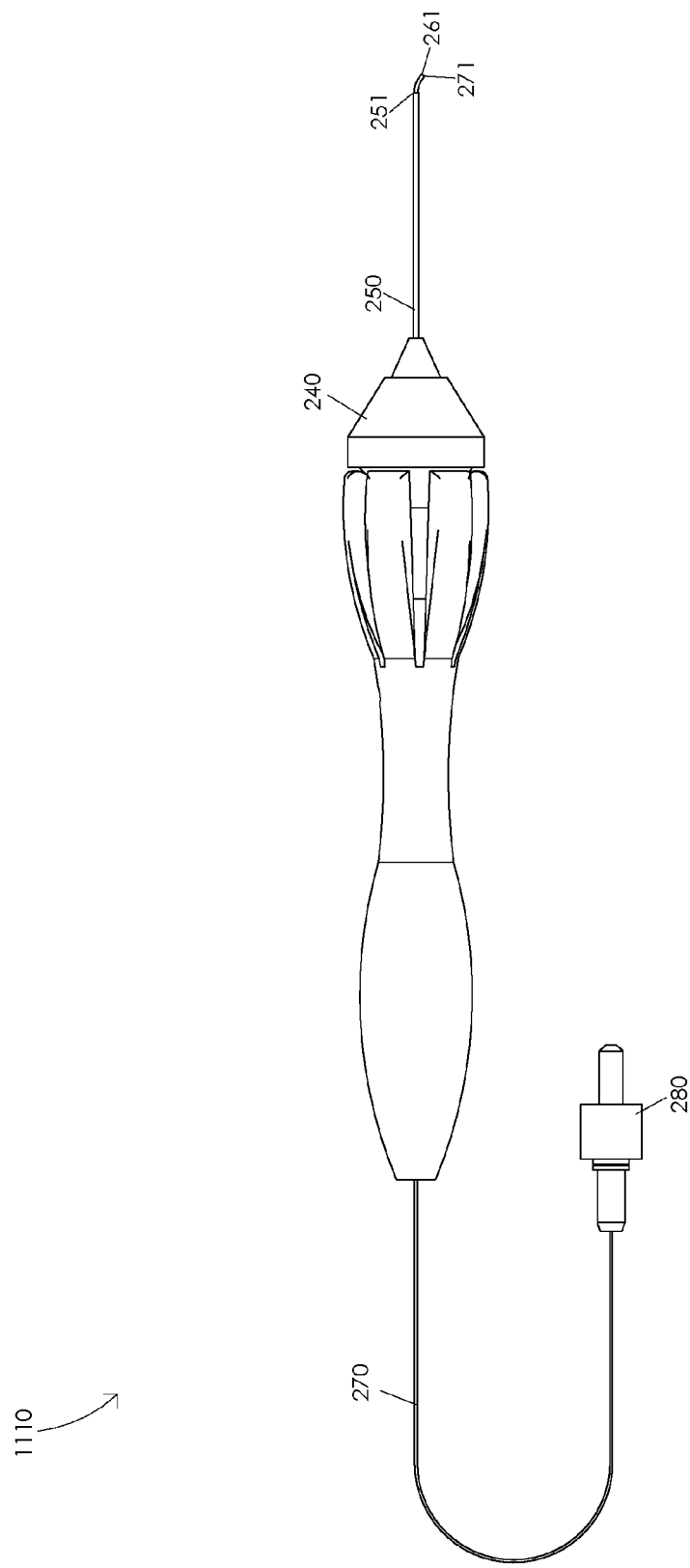
Figure 11C:
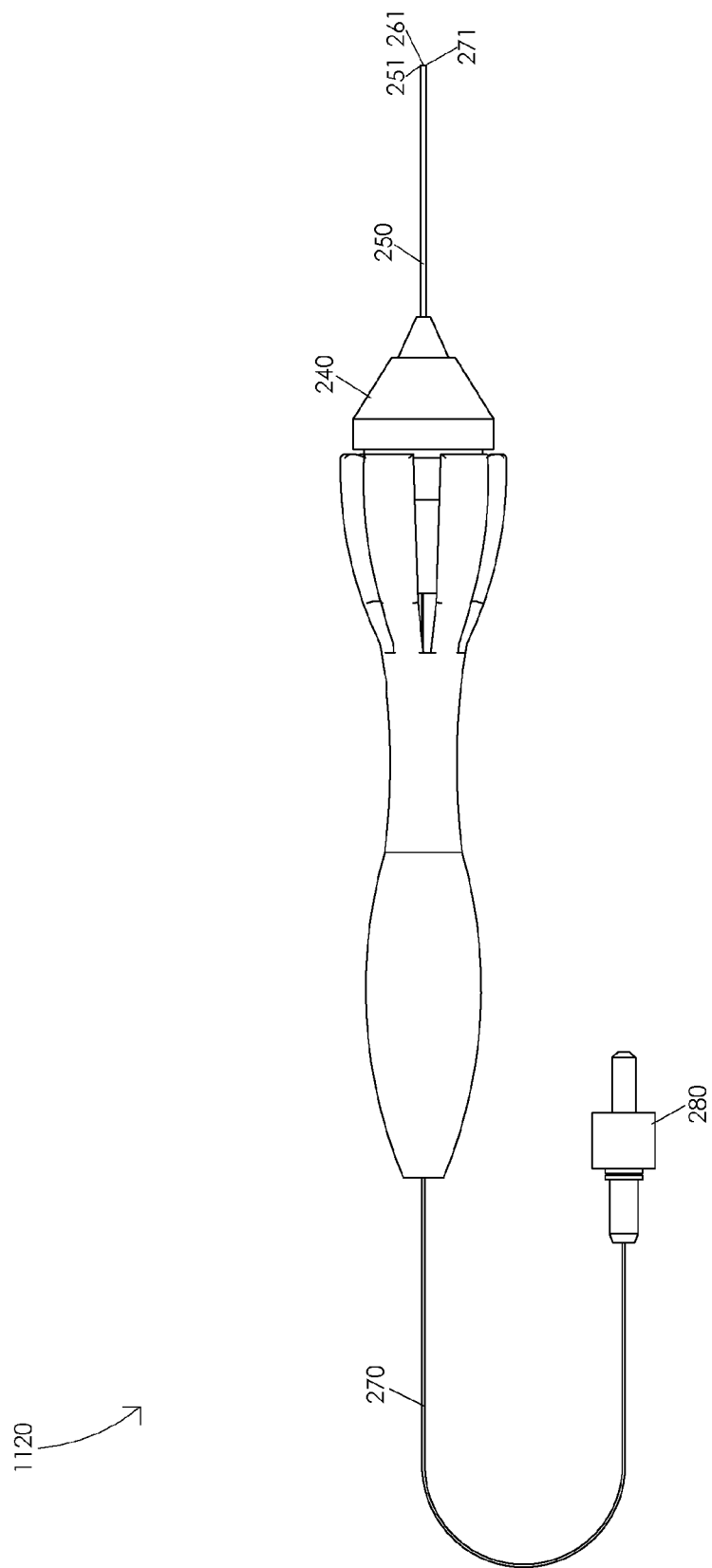

FIGS. 11A, 11B, and 11C are schematic diagrams illustrating a gradual straightening of an optic fiber 270. FIG. 11A illustrates an extended optic fiber 1100. Illustratively, optic fiber 270 may comprise an extended optic fiber 1100 when at least a portion of optic fiber 270 and shape memory sleeve 260 are extended from housing sleeve distal end 251. In one or more embodiments, a full compression of actuation structure 720 may be configured to extend optic fiber 270 and shape memory sleeve 260 from housing sleeve distal end 250 wherein optic fiber 270 may comprise a fully curved optic fiber 1020. Illustratively, optic fiber 270 may comprise an extended optic fiber 1100, e.g., due to a full compression of actuation structure 720.

FIG. 11B illustrates a partially retracted optic fiber 1110. Illustratively, housing sleeve 250 may be configured to hold a portion of pre-bent angle 265 in a straightened position within housing sleeve 250, e.g., when optic fiber 270 comprises a partially retracted optic fiber 1110. In one or more embodiments, a decompression of actuation structure 720 may be configured to retract optic fiber 270 and shape memory sleeve 260 into housing sleeve 250 wherein shape memory sleeve 260 may be configured to gradually straighten optic fiber 270 from a fully curved optic fiber 1020 to a partially curved optic fiber 1010.

FIG. 11C illustrates a fully retracted optic fiber 1120. Illustratively, housing sleeve 250 may be configured to hold pre-bent angle 265 in a straightened position within housing sleeve 250, e.g., when optic fiber 270 comprises a fully retracted optic fiber 1120. In one or more embodiments, a full decompression of actuation structure 720 may be configured to retract optic fiber 270 and shape memory sleeve 260 into housing sleeve 250 wherein shape memory sleeve 260 may be configured to gradually straighten optic fiber 270 from a partially curved optic fiber 1010 to a straightened optic fiber 1000.

Illustratively, a surgeon may aim optic fiber distal end 271 at any of a plurality of targets within an eye, e.g., to perform a photocoagulation procedure. In one or more embodiments, a surgeon may aim optic fiber distal end 271 at any target within a particular transverse plane of the inner eye by, e.g., rotating handle 700 to orient shape memory sleeve 260 in an orientation configured to cause a curvature of optic fiber 270 within the particular transverse plane of the inner eye and varying an amount of compression of actuation structure 720. Illustratively, a surgeon may aim optic fiber distal end 271 at any target within a particular sagittal plane of the inner eye by, e.g., rotating handle 700 to orient shape memory sleeve 260 in an orientation configured to cause a curvature of optic fiber 270 within the particular sagittal plane of the inner eye and varying an amount of compression of actuation structure 720. In one or more embodiments, a surgeon may aim optic fiber distal end 271 at any target within a particular frontal plane of the inner eye by, e.g., varying an amount of compression of actuation structure 720 to orient a line tangent to optic fiber distal end 271 wherein the line tangent to optic fiber distal end 271 is within the particular frontal plane of the inner eye and rotating handle 700. Illustratively, a surgeon may aim optic fiber distal end 271 at any target located outside of the particular transverse plane, the particular sagittal plane, and the particular frontal plane of the inner eye, e.g., by varying a rotational orientation of handle 700 and varying an amount of compression of actuation structure 720.

FIGS. 12A and 12B are schematic diagrams illustrating a handle 1200. FIG. 12A illustrates a top view of handle 1200. In one or more embodiments, handle 1200 may comprise a handle distal end 1201, a handle proximal end 1202, a handle base 1210, and an actuation structure 1220. Illustratively, actuation structure 1220 may comprise a plurality of actuation arms 1225. In one or more embodiments, actuation structure 1220 may comprise a shape memory material. Actuation structure 1220 may be manufactured from any suitable material, e.g., polymers, metals, metal alloys, etc., or from any combination of suitable materials.

Illustratively, actuation structure 1220 may be compressed by an application of a compressive force to actuation structure 1220. In one or more embodiments, actuation structure 1220 may be compressed by an application of one or more compressive forces located at one or more locations around an outer perimeter of actuation structure 1220. Illustratively, the one or more locations may comprise any of a plurality of locations around the outer perimeter of actuation structure 1220. For example, a surgeon may compress actuation structure 1220 by squeezing actuation structure 1220. Illustratively, the surgeon may compress actuation structure 1220 by squeezing actuation structure 1220 at any particular location of a plurality of locations around an outer perimeter of actuation structure 1220. For example, a surgeon may rotate handle 1200 and compress actuation structure 1220 from any rotational position of a plurality of rotational positions of handle 1200.

In one or more embodiments, actuation structure 1220 may be compressed by an application of a compressive force to any one or more of the plurality of actuation arms 1225. Illustratively, each actuation arm 1225 may be configured to actuate independently. In one or more embodiments, each actuation arm 1225 may be connected to one or more of the plurality of actuation arms 1225 wherein an actuation of a particular actuation arm 1225 may be configured to actuate every actuation arm 1225 of the plurality of actuation arms 1225. In one or more embodiments, a compression of actuation structure 1220, e.g., due to an application of a compressive force to a particular actuation arm 1225, may be configured to actuate the particular actuation arm 1225. Illustratively, an actuation of the particular actuation arm 1225 may be configured to actuate every actuation arm 1225 of the plurality of actuation arms 1225.

FIG. 12B illustrates a cross-sectional view of handle 1200. In one or more embodiments, handle 1200 may comprise an inner bore 1240, a fixation mechanism housing 1250, and a pressure mechanism proximal interface 1260. Handle 1200 may be manufactured from any suitable material, e.g., polymers, metals, metal alloys, etc., or from any combination of suitable materials.

Figure 13:
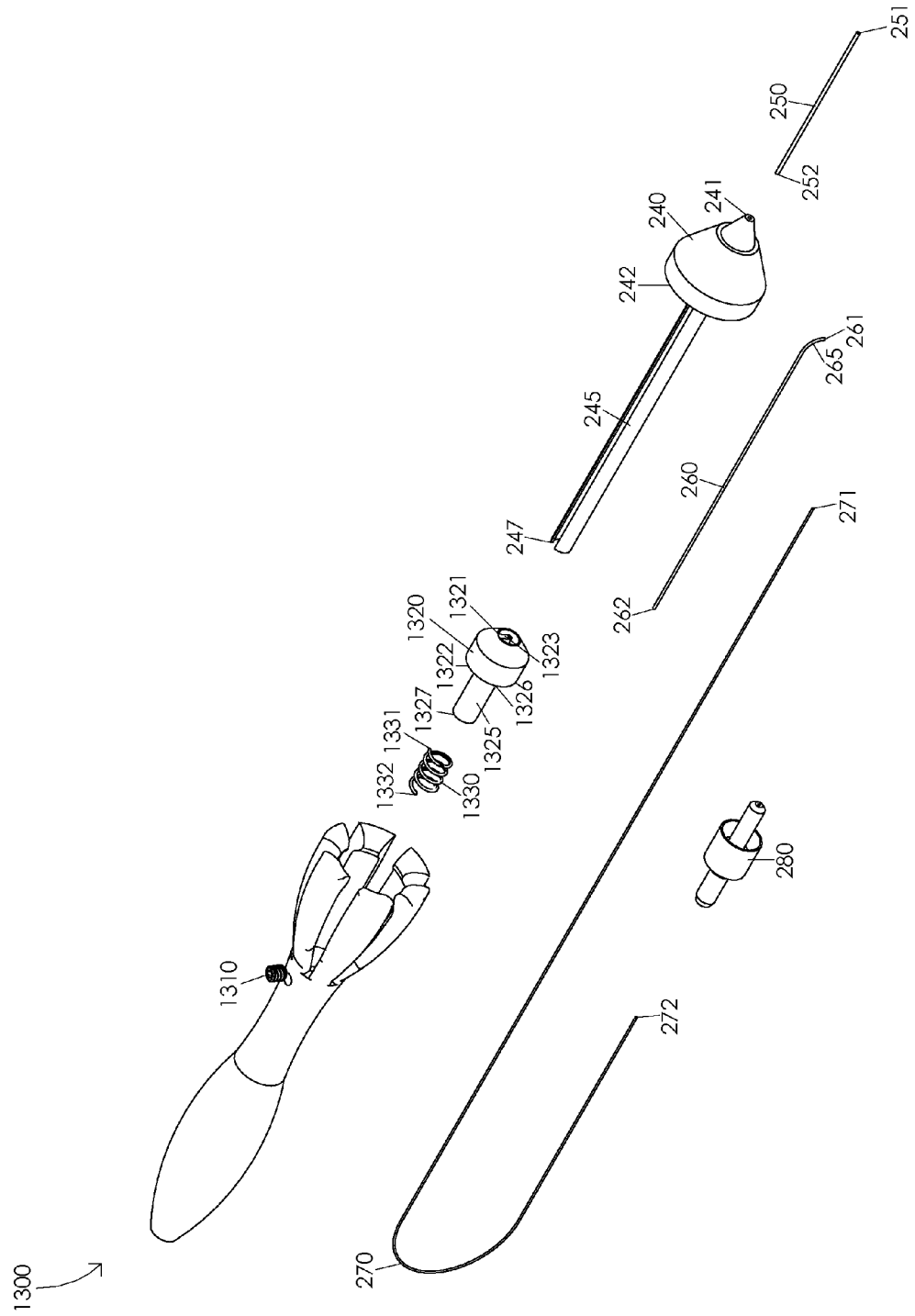
FIG. 13 illustrates an exploded view of a steerable laser probe assembly.

FIG. 13 illustrates an exploded view of a steerable laser probe assembly 1300. In one or more embodiments, steerable laser probe assembly 1300 may comprise a handle 1200, a fixation mechanism 1310, an actuation mechanism 1320 having an actuation mechanism distal end 1321 and an actuation mechanism proximal end 1322, a piston tube 1325 having a piston tube distal end 1326 and a piston tube proximal end 1327, a pressure mechanism 1330 having a pressure mechanism distal end 1331 and a pressure mechanism proximal end 1332, a nosecone 240 having a nosecone distal end 241 and a nosecone proximal end 242, an actuation guide 245 having an actuation guide proximal end 247, a housing sleeve 250 having a housing sleeve distal end 251 and a housing sleeve proximal end 252, a shape memory sleeve 260 having a shape memory sleeve distal end 261 and a shape memory sleeve proximal end 262, an optic fiber 270 having an optic fiber distal end 271 and an optic fiber proximal end 272, and a light source interface 280. Illustratively, light source interface 280 may be configured to interface with optic fiber proximal end 272. In one or more embodiments, light source interface 280 may comprise a standard light source connecter, e.g., an SMA connector.

Illustratively, actuation mechanism 1320 may comprise an actuation guide interface 1323 configured to interface with actuation guide 245. In one or more embodiments, piston tube 1325 may be fixed to actuation mechanism proximal end 1322. Illustratively, actuation mechanism 1320 and piston tube 1325 may be manufactured as a unit. In one or more embodiments, housing sleeve proximal end 252 may be fixed to nosecone distal end 241. Illustratively, actuation guide 245 may be fixed an inner portion of nosecone 240. In one or more embodiments, actuation guide 245, nosecone 240, and housing sleeve 250 may be manufactured as a unit.

Figure 14A:
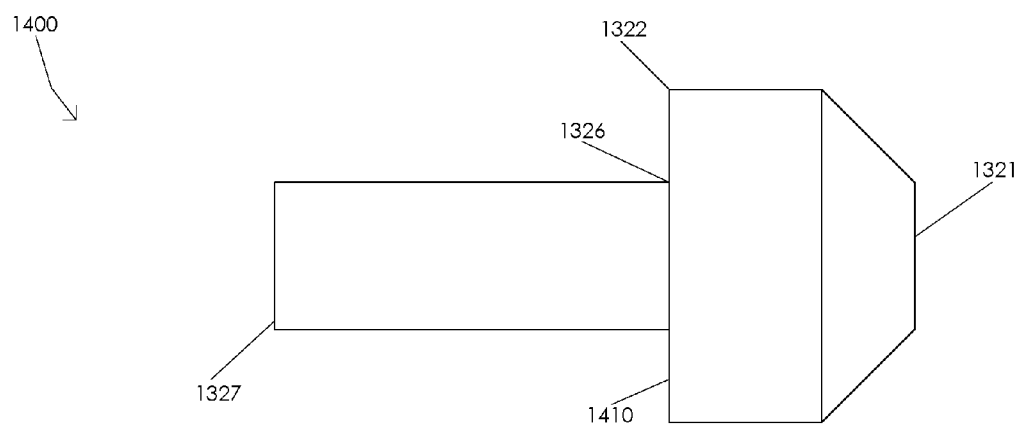
FIGS. 14A and 14B are schematic diagrams illustrating an assembled actuation mechanism.
Figure 14B:
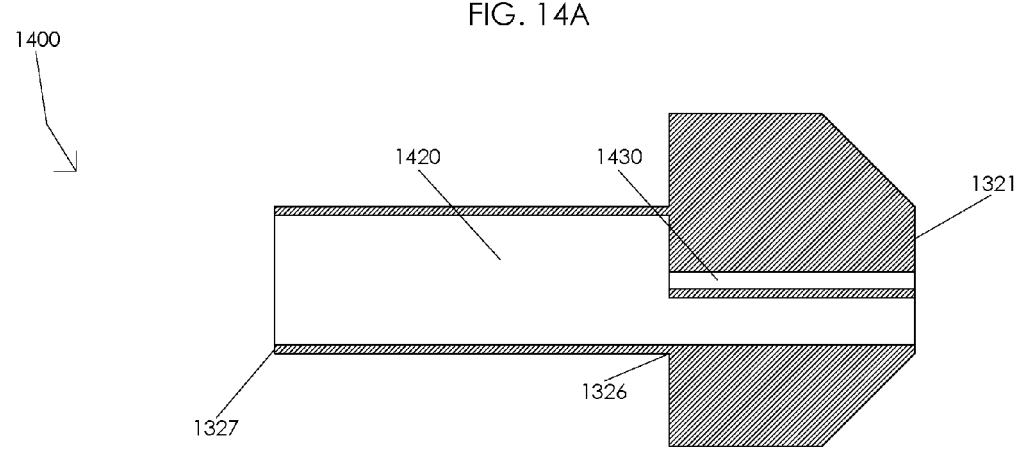

FIGS. 14A and 14B are schematic diagrams illustrating an assembled actuation mechanism 1400. FIG. 14A illustrates a top view of an assembled actuation mechanism 1400. Illustratively, assembled actuation mechanism 1400 may comprise a pressure mechanism distal interface 1410. FIG. 14B illustrates a cross-sectional view of an assembled actuation mechanism 1400. In one or more embodiments, assembled actuation mechanism 1400 may comprise an actuation mechanism inner chamber 1420 and a shape memory sleeve housing 1430.

FIGS. 15A and 15B are schematic diagrams illustrating an assembled steerable laser probe 1500. FIG. 15A illustrates a side view of an assembled steerable laser probe 1500. Illustratively, optic fiber 270 may be disposed within shape memory sleeve 260, e.g., optic fiber distal end 271 may be adjacent to shape memory sleeve distal end 261. Optic fiber 270 may be fixed in a position within shape memory sleeve 260, e.g., by a biocompatible adhesive or any other suitable fixation means. In one or more embodiments, shape memory sleeve 260 may comprise a pre-bent angle 265 configured to curve optic fiber 270 towards pre-bent angle 265. Illustratively, shape memory sleeve 260 may comprise a shape memory material, e.g., nitinol, configured to steer optic fiber 270 towards one or more surgical targets within an eye. Shape memory sleeve 260 may be manufactured from any suitable material, e.g., polymers, metals, metal alloys, etc., or from any combination of suitable materials.

FIG. 15B illustrates a cross-sectional view of an assembled steerable laser probe 1500. Illustratively, pressure mechanism 1330 may be disposed over piston tube 1325, e.g., pressure mechanism distal end 1331 may abut pressure mechanism distal interface 1410. In one or more embodiments, pressure mechanism 1330 may be configured to provide a force. Illustratively, pressure mechanism 1330 may comprise a spring. Pressure mechanism 1330 may be manufactured from any suitable material, e.g., polymers, metals, metal alloys, etc., or from any combination of suitable materials.

Illustratively, actuation guide 245 may be disposed within actuation mechanism 1320 and piston tube 1325, e.g., actuation mechanism proximal end 247 may extend a distance from piston tube proximal end 1327. In one or more embodiments, actuation guide interface 1323 may be configured to interface with actuation guide 245, e.g., when actuation guide 245 is disposed within actuation mechanism 1320, actuation guide interface 1323 may be contained within actuation channel 310. Illustratively, pressure mechanism 1330 may be disposed between actuation mechanism 1320 and pressure mechanism proximal interface 1260, e.g., pressure mechanism proximal end 1332 may abut pressure mechanism proximal interface 1260 and pressure mechanism distal end 1331 may abut pressure mechanism distal interface 1410.

In one or more embodiments, actuation guide 245 may be disposed within inner bore 1240. Illustratively, piston tube 1325 and pressure mechanism 1330 may be disposed within actuation structure 1220. In one or more embodiments, a portion of actuation mechanism 1320 may be disposed within actuation structure 1220. Illustratively, optic fiber 270 and shape memory sleeve 260 may be disposed within inner bore 1240, actuation guide inner bore 320, piston tube 1325, actuation mechanism 1320, shape memory sleeve housing 1430, housing sleeve guide 340, and housing sleeve 250. In one or more embodiments, optic fiber 270 and shape memory sleeve 260 may be fixed to an inner portion of actuation mechanism 1320, e.g., optic fiber 270 and shape memory sleeve 260 may be fixed within shape memory sleeve housing 1430. For example, shape memory sleeve 260 may be fixed within shape memory sleeve housing 1430 by an adhesive or by any suitable fixation means. Illustratively, an actuation of actuation mechanism 1320 may be configured to actuate optic fiber 270 and shape memory sleeve 260.

In one or more embodiments, fixation mechanism 1310 may be configured to fix actuation guide 245 in a position relative to handle 1200. For example, fixation mechanism 1310 may comprise a set screw configured to fix actuation guide 245 in a position relative to handle 1200, e.g., by an interference fit in actuation channel 310. In one or more embodiments, fixation mechanism 1310 may comprise an adhesive material configured to fix actuation guide 245 in a position relative to handle 1200, or fixation mechanism 1310 may comprise one or more magnets configured to fix actuation guide 245 in a position relative to handle 1200.

Illustratively, a compression of actuation structure 1220 may be configured to retract a portion of actuation mechanism 1320 into actuation structure 1220. For example, a compression of actuation structure 1220 may be configured to retract actuation mechanism 1320 relative to handle proximal end 1202. In one or more embodiments, an application of a compressive force to one or more actuation arms 1225 of actuation structure 1220 may be configured to retract actuation mechanism 1320 relative to handle proximal end 1202. For example, a compression of actuation structure 1220 may be configured to actuate actuation mechanism 1320 along actuation mechanism guide 245. In one or more embodiments, a compression of actuation structure 1220 may be configured to retract actuation guide interface 1323 within actuation channel 310, e.g., away from nosecone distal end 241 and towards handle proximal end 1202. Illustratively, pressure mechanism 1330 may be configured to provide a resistive force that resists a retraction of actuation mechanism 1320 relative to handle proximal end 1202.

In one or more embodiments, a retraction of actuation mechanism 1320 away from nosecone distal end 241 and towards handle proximal end 1202, e.g., due to a compression of actuation structure 1220, may be configured to retract optic fiber 270 and shape memory sleeve 260 relative to housing sleeve 250. Illustratively, a compression of actuation structure 1220 may be configured to actuate optic fiber 270 and shape memory sleeve 260 relative to housing sleeve 250 wherein optic fiber 270 and shape memory sleeve 260 may be gradually retracted into housing sleeve 250. In one or more embodiments, shape memory sleeve 260 and optic fiber 270 may be gradually straightened as shape memory sleeve 260 and optic fiber 270 are gradually retracted into housing sleeve 250.

Illustratively, a decompression of actuation structure 1220 may be configured to extend a portion of actuation mechanism 1320 from actuation structure 1220. For example, a decompression of actuation structure 1220 may be configured to extend actuation mechanism 1320 relative to handle proximal end 1202. In one or more embodiments, a reduction of a compressive force applied to one or more actuation arms 1225 of actuation structure 1220 may be configured to extend actuation mechanism 1320 towards nosecone distal end 241 and away from handle proximal end 1202. For example, a decompression of actuation structure 1220 may be configured to actuate actuation mechanism 1320 along actuation mechanism guide 245. In one or more embodiments, a decompression of actuation structure 1220 may be configured to advance actuation guide interface 1323 within actuation channel 310, e.g., away from actuation guide proximal end 247 and towards nosecone distal end 241. Illustratively, pressure mechanism 1330 may be configured to provide a facilitating force that facilitates an extension of actuation mechanism 1320 relative to handle proximal end 1202.

In one or more embodiments, an extension of actuation mechanism 1320 towards nosecone distal end 241 and away from handle proximal end 1202, e.g., due to a decompression of actuation structure 1220, may be configured to extend shape memory sleeve 260 and optic fiber 270 relative to housing sleeve 250. Illustratively, a decompression of actuation structure 1220 may be configured to actuate shape memory sleeve 260 and optic fiber 270 relative to housing sleeve 250 wherein shape memory sleeve 260 and optic fiber 270 may be gradually extended from housing sleeve distal end 251. In one or more embodiments, shape memory sleeve 260 may be configured to gradually curve optic fiber 270, e.g., towards pre-bent angle 265, as shape memory sleeve 260 and optic fiber 270 are gradually extended from housing sleeve distal end 251.

Figure 16A:
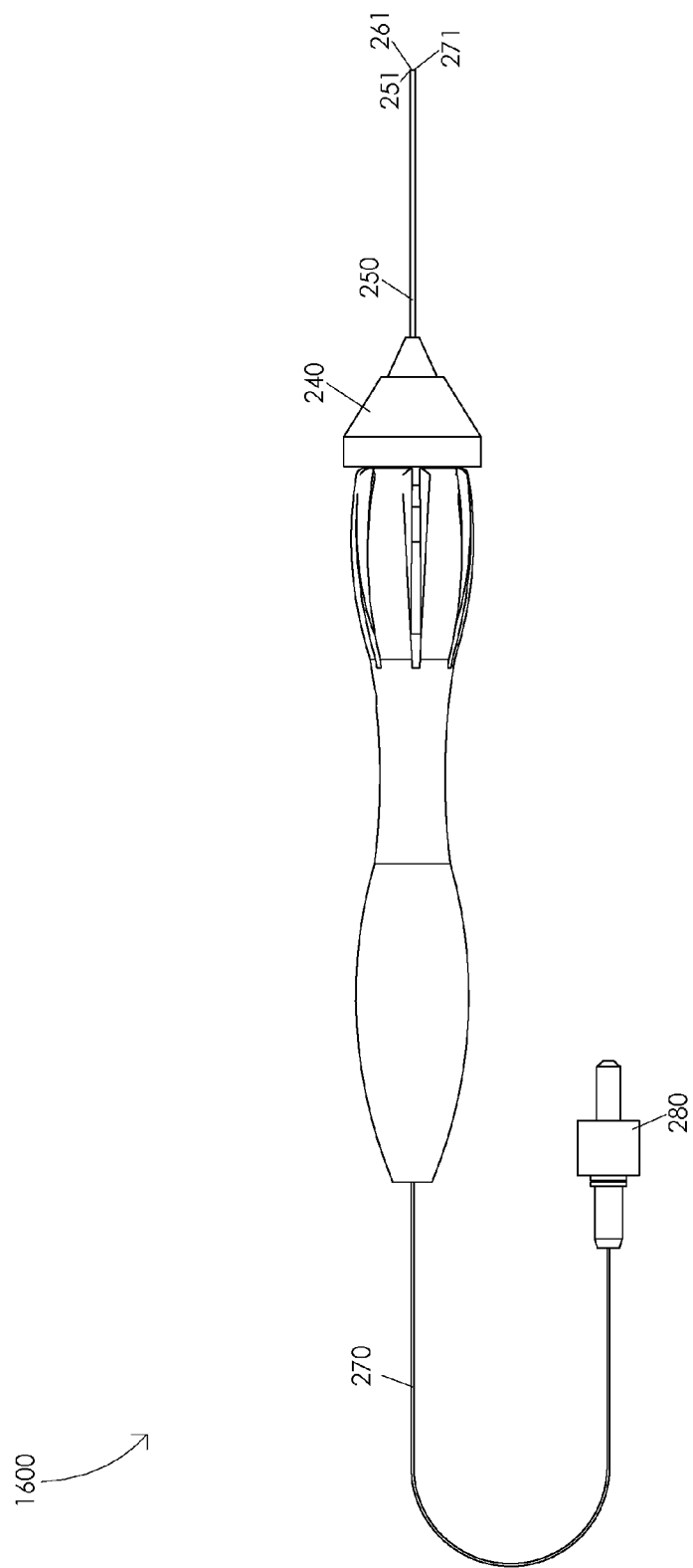
FIGS. 16A, 16B, and 16C are schematic diagrams illustrating a gradual curving of an optic fiber.
Figure 16B:
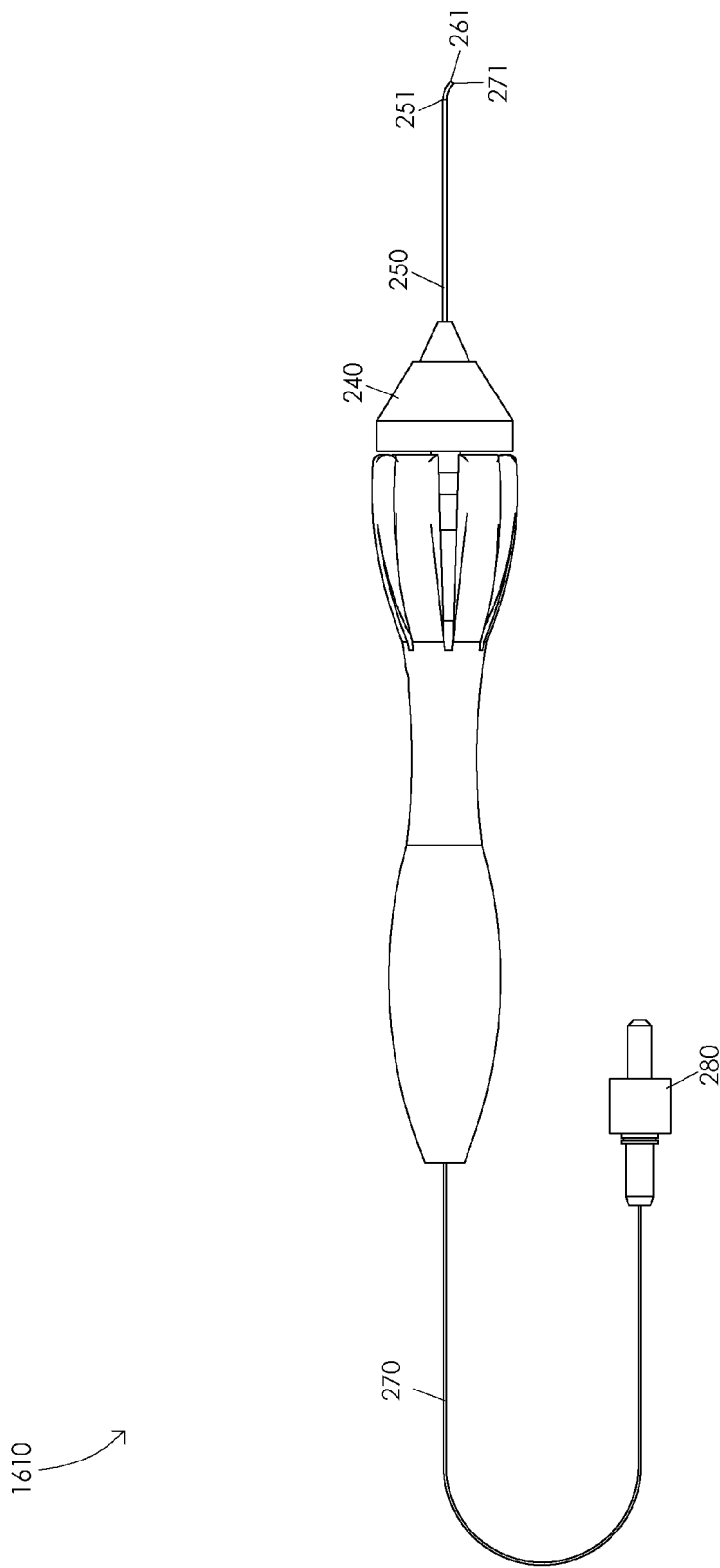
Figure 16C:
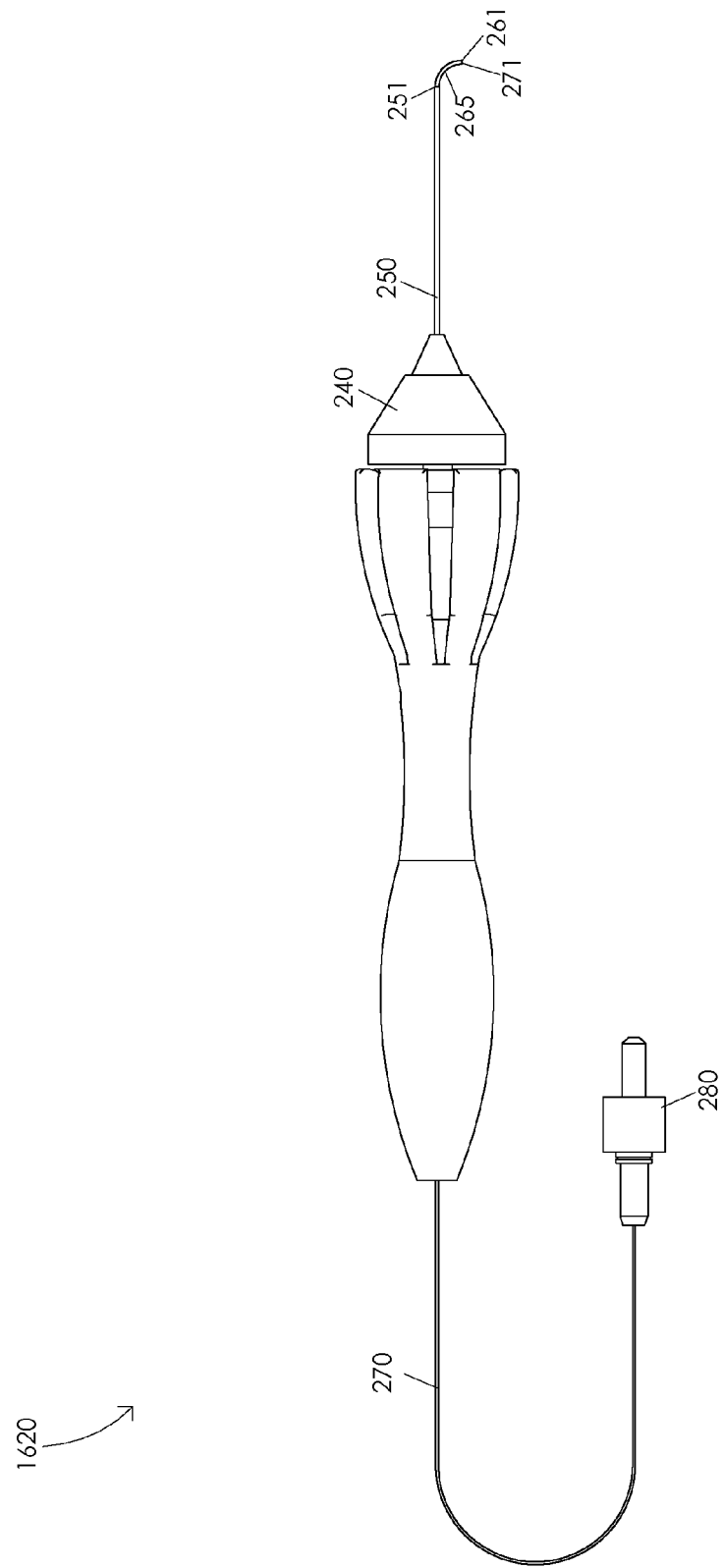

FIGS. 16A, 16B, and 16C are schematic diagrams illustrating a gradual curving of an optic fiber 270. FIG. 16A illustrates a straightened optic fiber 1600. Illustratively, straightened optic fiber 1600 may be fully contained within housing sleeve 250. In one or more embodiments, optic fiber 270 and shape memory sleeve 260 may be fully contained within housing sleeve 250, e.g., when actuation structure 1220 is fully compressed. For example, actuation mechanism 1320 may be fully retracted relative to handle proximal end 1202, e.g., when optic fiber 270 comprises a straightened optic fiber 1600. Illustratively, when optic fiber 270 and shape memory sleeve 260 are fully contained within housing sleeve 250, pre-bent angle 265 of shape memory sleeve 260 may be straightened by housing sleeve 250. For example, an angle between housing sleeve 250 and a line tangent to optic fiber distal end 271 may be, e.g., 180 degrees, when housing sleeve 250 contains a straightened optic fiber 1600.

FIG. 16B illustrates a partially curved optic fiber 1610. In one or more embodiments, a decompression of a fully compressed actuation structure 1220 may be configured to gradually extend optic fiber 270 and shape memory sleeve 260 from housing sleeve distal end 251. Illustratively, as optic fiber 270 and shape memory sleeve 260 are gradually extended from housing sleeve distal end 251, shape memory sleeve 260 may be configured to cause optic fiber 270 to gradually curve toward pre-bent angle 265. In one or more embodiments, a decompression of actuation structure 1220 may be configured to cause a straightened optic fiber 1600 to gradually curve to a partially curved optic fiber 1610. Illustratively, a decompression of actuation structure 1220 may be configured to gradually extend optic fiber 270 and shape memory sleeve 260 out of housing sleeve 250 causing optic fiber 270 to gradually curve toward pre-bent angle 265. For example, as an extended length of optic fiber 270 and shape memory sleeve 260 is increased, e.g., by a decompression of actuation structure 1220, an angle between housing sleeve 250 and a line tangent to optic fiber distal end 271 may be decreased.

Illustratively, optic fiber 270 and shape memory sleeve 260 may be extended from housing sleeve distal end 251 at a first extended length with a first angle between housing sleeve 250 and a line tangent to optic fiber distal end 271. An extension of optic fiber 270 and shape memory sleeve 260 from housing sleeve distal end 251, e.g., due to a decompression of actuation structure 1220, may be configured to extend optic fiber 270 and shape memory sleeve 260 from housing sleeve distal end 251 at a second extended length with a second angle between housing sleeve 250 and a line tangent to optic fiber distal end 271. Illustratively, the second extended length may be greater than the first extended length and the second angle may be less than the first angle.

FIG. 16C illustrates a fully curved optic fiber 1620. Illustratively, when actuation mechanism 1320 is fully extended relative to handle proximal end 1202, e.g., due to a full decompression of actuation structure 1220, a fully curved optic fiber 1620 may be extended from housing sleeve distal end 251. In one or more embodiments, a decompression of actuation structure 1220 may be configured to cause a partially curved optic fiber 1610 to gradually curve to a fully curved optic fiber 1620.

Illustratively, when actuation mechanism 1320 is extended relative to handle proximal end 1202 to extend a partially curved optic fiber 1610 from housing sleeve distal end 251, optic fiber 270 and shape memory sleeve 260 may be extended from housing sleeve distal end 251 at a partially extended length with a partially extended angle between housing sleeve 250 and a line tangent to optic fiber distal end 271. An extension of optic fiber 270 and shape memory sleeve 260 from housing sleeve distal end 251, e.g., due to a full decompression of actuation structure 1220, may be configured to extend optic fiber 270 and shape memory sleeve 260 from housing sleeve distal end 251 at fully extended length with a fully extended angle between housing sleeve 250 and a line tangent to optic fiber distal end 271. For example, optic fiber 270 and shape memory sleeve 260 may extend from housing sleeve distal end 251 at a fully extended length with a fully extended angle between housing sleeve 250 and a line tangent to optic fiber distal end 271, e.g., when optic fiber 270 comprises a fully curved optic fiber 1620. Illustratively, the fully extended length may be greater than the partially extended length and the fully extended angle may be less than the partially extended angle.

In one or more embodiments, one or more properties of a steerable laser probe may be adjusted to attain one or more desired steerable laser probe features. Illustratively, a position of fixation mechanism housing 1250 and fixation mechanism 1310 or a length of optic fiber 270 and shape memory sleeve 260 extending distally from a position of fixation mechanism 1310 may be adjusted to vary an amount of decompression of actuation structure 1220 configured to extend a particular length of optic fiber 270 and shape memory sleeve 260 from housing sleeve distal end 251. In one or more embodiments, one or more properties of pressure mechanism 1330 may be adjusted to attain one or more desired steerable laser probe features. Illustratively, a spring constant of pressure mechanism 1330 may be adjusted to vary an amount of decompression of actuation structure 1220 configured to extend a particular length of optic fiber 270 and shape memory sleeve 260 from housing sleeve distal end 251. In one or more embodiments, a geometry of actuation mechanism 1320 may be adjusted to vary an amount of decompression of actuation structure 1220 configured to extend a particular length of optic fiber 270 and shape memory sleeve 260 from housing sleeve distal end 251. Illustratively, a length of housing sleeve 250 may be adjusted to vary an amount of decompression of actuation structure 1220 configured to extend a particular length of optic fiber 270 and shape memory sleeve 260 from housing sleeve distal end 251. In one or more embodiments, a geometry of actuation structure 1220 may be adjusted to vary an amount of decompression of actuation structure 1220 configured to extend a particular length of optic fiber 270 and shape memory sleeve 260 from housing sleeve distal end 251. Illustratively, a magnitude of pre-bent angle 265 may be adjusted to vary a magnitude of an angle between housing sleeve 250 and a line tangent to optic fiber distal end 271 when a particular length of optic fiber 270 and shape memory sleeve 260 is extended from housing sleeve distal end 251.

In one or more embodiments, one or more properties of optic fiber 270 may be adjusted to attain one or more steerable laser probe features. For example, a portion of optic fiber 270 may be formed in a pre-bent angle. Illustratively, a portion of optic fiber 270 may be formed in a pre-bent angle by, e.g., heating the portion of optic fiber 270 to a temperature configured to weaken chemical bonds of the portion of optic fiber 270, molding the portion of optic fiber 270 in a pre-bent angle, and cooling the portion of optic fiber 270. In one or more embodiments, optic fiber 270 may be coated by a buffer material. Illustratively, the buffer material may comprise a fluoropolymer, e.g., Teflon, Tefzel, etc. In one or more embodiments, a portion of optic fiber 270 may be formed in a pre-bent angle by, e.g., heating the buffer material to a temperature configured to weaken chemical bonds of the buffer material, molding the portion of optic fiber 270 in a pre-bent angle, and cooling the buffer material. Illustratively, housing sleeve 250 may be configured to hold a pre-bent angle of optic fiber 270 in a straightened position, e.g., when optic fiber 270 is fully contained within housing sleeve 250. In one or more embodiments, a decompression of actuation structure 1220 may be configured to extend optic fiber 270 relative to housing sleeve 250 causing optic fiber 270 to gradually curve towards the pre-bent angle as optic fiber 270 is gradually extended from housing sleeve distal end 251.

Figure 17A:
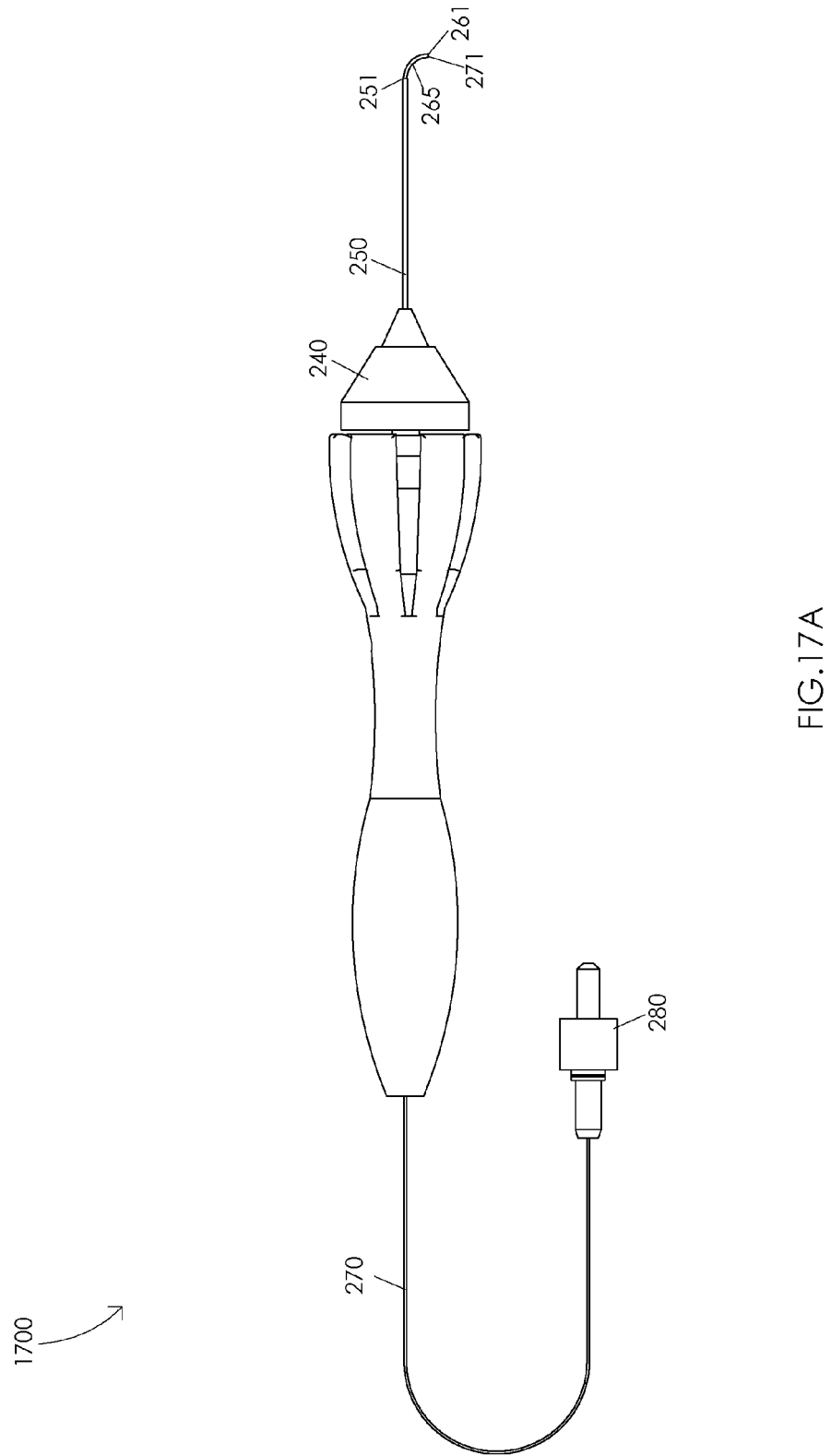
FIGS. 17A, 17B, and 17C are schematic diagrams illustrating a gradual straightening of an optic fiber.
Figure 17B:
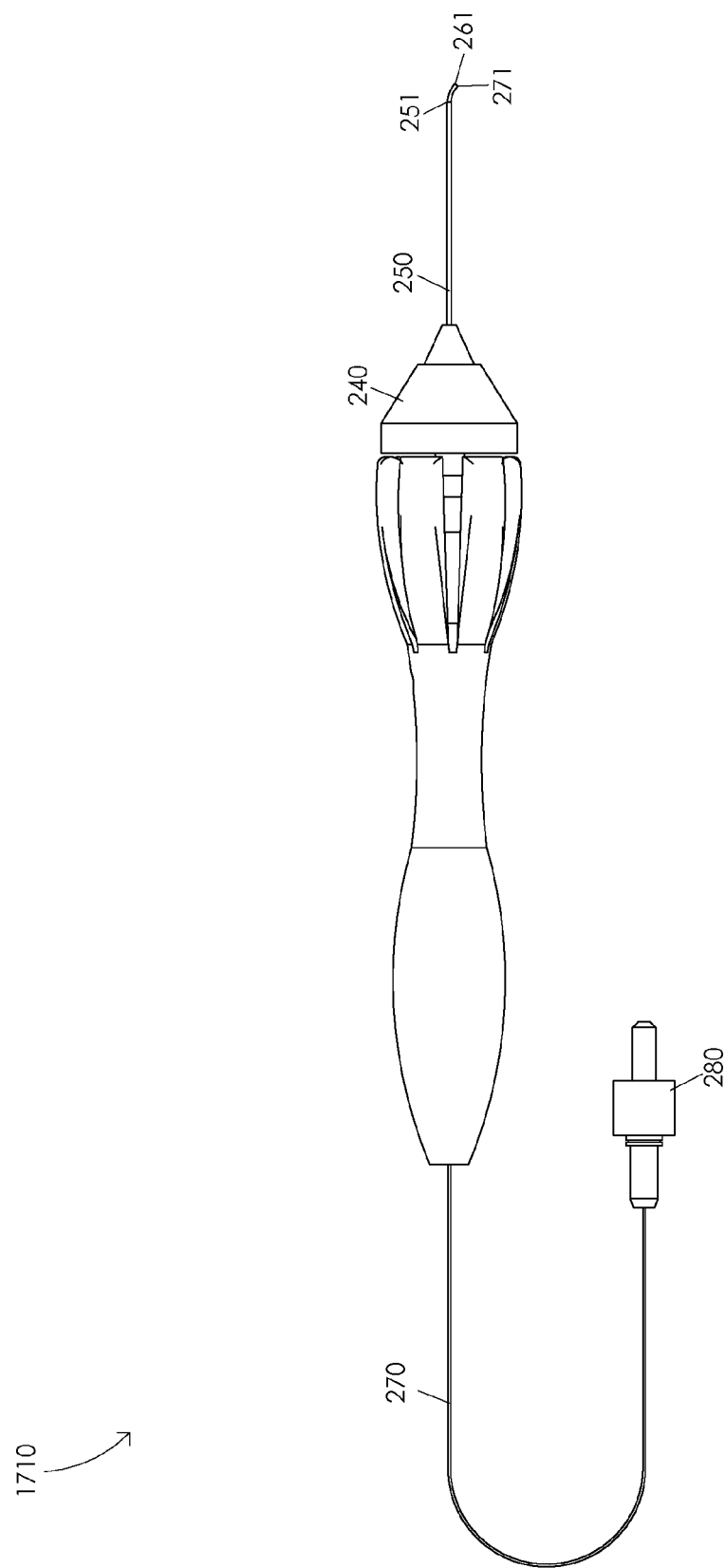
Figure 17C:
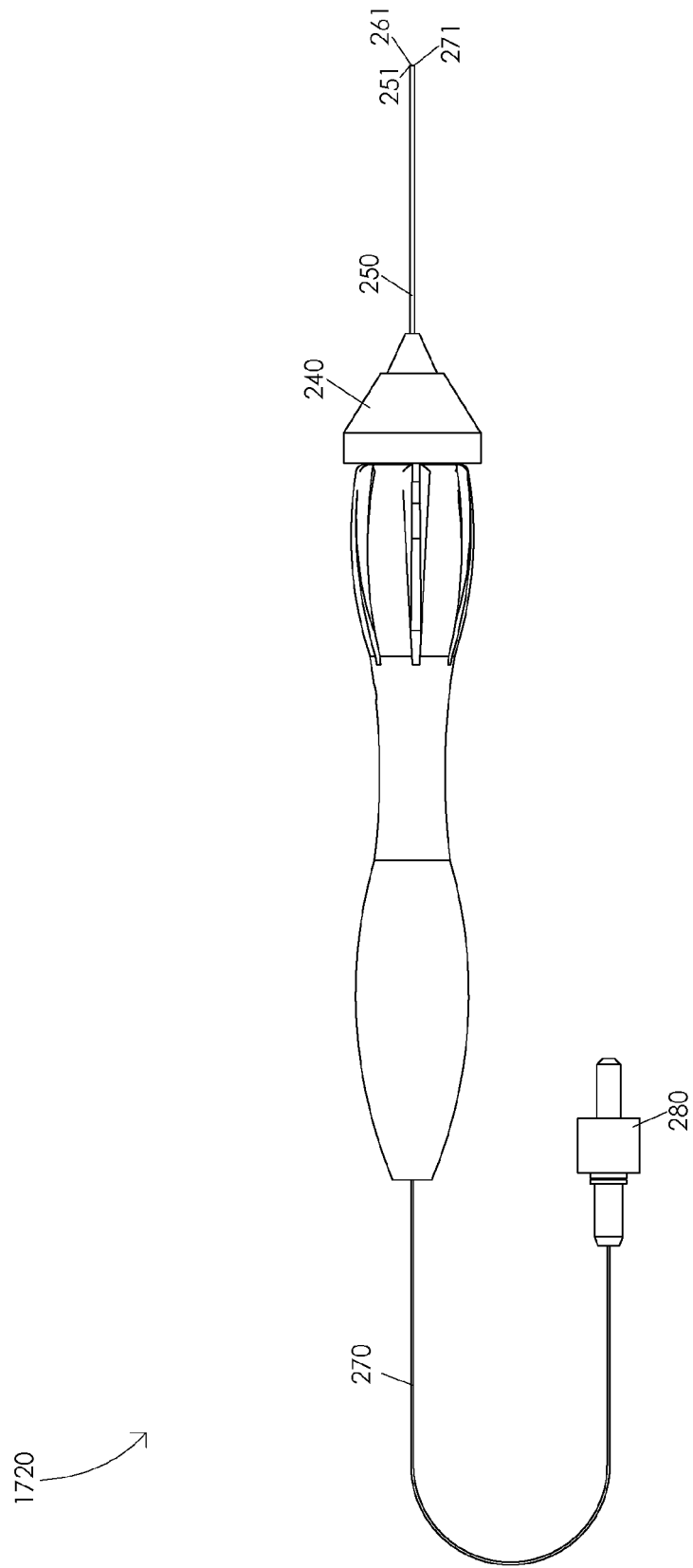

FIGS. 17A, 17B, and 17C are schematic diagrams illustrating a gradual straightening of an optic fiber 270. FIG. 17A illustrates an extended optic fiber 1700. Illustratively, actuation mechanism 1320 may be extended relative to handle proximal end 1202 to extend at least a portion of optic fiber 270 and shape memory sleeve 260, e.g., when optic fiber 270 comprises an extended optic fiber 1700. In one or more embodiments, a full decompression of actuation structure 1220 may be configured to extend optic fiber 270 and shape memory sleeve 260 relative to housing sleeve 250 wherein a fully curved optic fiber 1620 may be extended from housing sleeve distal end 251. Illustratively, optic fiber 270 may comprise an extended optic fiber 1700, e.g., due to a full decompression of actuation structure 1220.

FIG. 17B illustrates a partially retracted optic fiber 1710. Illustratively, housing sleeve 250 may be configured to hold a portion of pre-bent angle 265 in a straightened position within housing sleeve 250, e.g., when optic fiber 270 comprises a partially retracted optic fiber 1710. In one or more embodiments, a compression of actuation structure 1220 may be configured to retract optic fiber 270 and shape memory sleeve 260 into housing sleeve 250 causing shape memory sleeve 260 to gradually straighten optic fiber 270 from a fully curved optic fiber 1620 to a partially curved optic fiber 1610.

FIG. 17C illustrates a fully retracted optic fiber 1720. Illustratively, housing sleeve 250 may be configured to hold pre-bent angle 265 in a straightened position within housing sleeve 250, e.g., when optic fiber 270 comprises a fully retracted optic fiber 1720. In one or more embodiments, a full compression of actuation structure 1220 may be configured to retract optic fiber 270 and shape memory sleeve 260 into housing sleeve 250 causing shape memory sleeve 260 to gradually straighten optic fiber 270 from a partially curved optic fiber 1610 to a straightened optic fiber 1600.

Illustratively, a surgeon may aim optic fiber distal end 271 at any of a plurality of targets within an eye, e.g., to perform a photocoagulation procedure. In one or more embodiments, a surgeon may aim optic fiber distal end 271 at any target within a particular transverse plane of the inner eye by, e.g., rotating handle 1200 to orient shape memory sleeve 260 in an orientation configured to cause a curvature of optic fiber 270 within the particular transverse plane of the inner eye and varying an amount of compression of actuation structure 1220. Illustratively, a surgeon may aim optic fiber distal end 271 at any target within a particular sagittal plane of the inner eye by, e.g., rotating handle 1200 to orient shape memory sleeve 260 in an orientation configured to cause a curvature of optic fiber 270 within the particular sagittal plane of the inner eye and varying an amount of compression of actuation structure 1220. In one or more embodiments, a surgeon may aim optic fiber distal end 271 at any target within a particular frontal plane of the inner eye by, e.g., varying an amount of compression of actuation structure 1220 to orient a line tangent to optic fiber distal end 271 wherein the line tangent to optic fiber distal end 271 is within the particular frontal plane of the inner eye and rotating handle 1200. Illustratively, a surgeon may aim optic fiber distal end 271 at any target located outside of the particular transverse plane, the particular sagittal plane, and the particular frontal plane of the inner eye, e.g., by varying a rotational orientation of handle 1200 and varying an amount of compression of actuation structure 1220.

FIGS. 18A and 18B are schematic diagrams illustrating a handle 1800. FIG. 18A illustrates a top view of handle 1800. In one or more embodiments, handle 1800 may comprise a handle distal end 1801, a handle proximal end 1802, a handle base 1810, and an actuation structure 1820. Illustratively, actuation structure 1820 may comprise a plurality of actuation arms 1825. In one or more embodiments, actuation structure 1820 may comprise a shape memory material. Actuation structure 1820 may be manufactured from any suitable material, e.g., polymers, metals, metal alloys, etc., or from any combination of suitable materials.

Illustratively, actuation structure 1820 may be compressed by an application of a compressive force to actuation structure 1820. In one or more embodiments, actuation structure 1820 may be compressed by an application of one or more compressive forces located at one or more locations around an outer perimeter of actuation structure 1820. Illustratively, the one or more locations may comprise any of a plurality of locations around the outer perimeter of actuation structure 1820. For example, a surgeon may compress actuation structure 1820 by squeezing actuation structure 1820. Illustratively, the surgeon may compress actuation structure 1820 by squeezing actuation structure 1820 at any particular location of a plurality of locations around an outer perimeter of actuation structure 1820. For example, a surgeon may rotate handle 100 and compress actuation structure 1820 from any rotational position of a plurality of rotational positions of handle 1800.

In one or more embodiments, actuation structure 1820 may be compressed by an application of a compressive force to any one or more of the plurality of actuation arms 1825. Illustratively, each actuation arm 1825 may be configured to actuate independently. In one or more embodiments, each actuation arm 1825 may be connected to one or more of the plurality of actuation arms 1825 wherein an actuation of a particular actuation arm 1825 may be configured to actuate every actuation arm 1825 of the plurality of actuation arms 1825. In one or more embodiments, a compression of actuation structure 1820, e.g., due to an application of a compressive force to a particular actuation arm 1825, may be configured to actuate the particular actuation arm 1825. Illustratively, an actuation of the particular actuation arm 1825 may be configured to actuate every actuation arm 1825 of the plurality of actuation arms 1825.

FIG. 18B illustrates a cross-sectional view of handle 1800. In one or more embodiments, handle 1800 may comprise an inner bore 1840, a fixation mechanism housing 1850, and a pressure mechanism proximal interface 1860. Handle 1800 may be manufactured from any suitable material, e.g., polymers, metals, metal alloys, etc., or from any combination of suitable materials.

Figure 19:
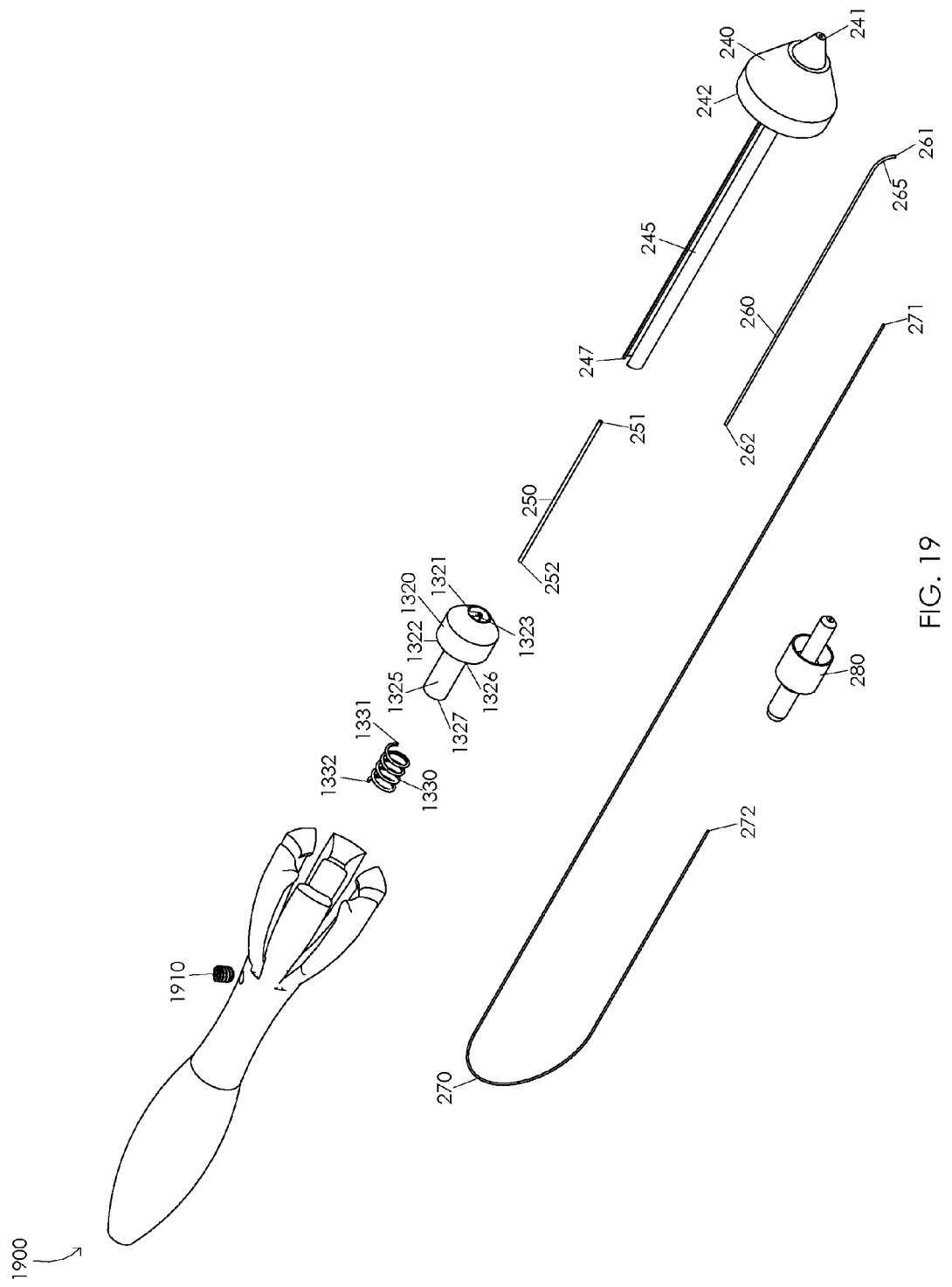
FIG. 19 illustrates an exploded view of a steerable laser probe assembly.

FIG. 19 illustrates an exploded view of a steerable laser probe assembly 1900. In one or more embodiments, steerable laser probe assembly 1900 may comprise a handle 1800, a fixation mechanism 1910, an actuation mechanism 1320 having an actuation mechanism distal end 1321 and an actuation mechanism proximal end 1322, a piston tube 1325 having a piston tube distal end 1326 and a piston tube proximal end 1327, a pressure mechanism 1330 having a pressure mechanism distal end 1331 and a pressure mechanism proximal end 1332, a nosecone 240 having a nosecone distal end 241 and a nosecone proximal end 242, an actuation guide 245 having an actuation guide proximal end 247, a housing sleeve 250 having a housing sleeve distal end 251 and a housing sleeve proximal end 252, a shape memory sleeve 260 having a shape memory sleeve distal end 261 and a shape memory sleeve proximal end 262, an optic fiber 270 having an optic fiber distal end 271 and an optic fiber proximal end 272, and a light source interface 280. Illustratively, light source interface 280 may be configured to interface with optic fiber proximal end 272. In one or more embodiments, light source interface 280 may comprise a standard light source connecter, e.g., an SMA connector.

Illustratively, actuation mechanism 1320 may comprise an actuation guide interface 1323 configured to interface with actuation guide 245. In one or more embodiments, piston tube 1325 may be fixed to actuation mechanism proximal end 1322. Illustratively, housing sleeve 250 may be fixed to actuation mechanism 1320, e.g., housing sleeve proximal end 252 may be fixed to actuation mechanism distal end 1321. In one or more embodiments, actuation mechanism 1320, piston tube 1325, and housing sleeve 250 may be manufactured as a unit. Illustratively, actuation guide 245 may be fixed an inner portion of nosecone 240. In one or more embodiments, actuation guide 245, nosecone 240, and housing sleeve 250 may be manufactured as a unit.

FIGS. 20A and 20B are schematic diagrams illustrating an assembled steerable laser probe 2000. FIG. 20A illustrates a side view of an assembled steerable laser probe 2000. Illustratively, optic fiber 270 may be disposed within shape memory sleeve 260, e.g., optic fiber distal end 271 may be adjacent to shape memory sleeve distal end 261. Optic fiber 270 may be fixed in a position within shape memory sleeve 260, e.g., by a biocompatible adhesive or any other suitable fixation means. In one or more embodiments, shape memory sleeve 260 may comprise a pre-bent angle 265 configured to curve optic fiber 270 towards pre-bent angle 265. Illustratively, shape memory sleeve 260 may comprise a shape memory material, e.g., nitinol, configured to steer optic fiber 270 towards one or more surgical targets within an eye. Shape memory sleeve 260 may be manufactured from any suitable material, e.g., polymers, metals, metal alloys, etc., or from any combination of suitable materials.

FIG. 20B illustrates a cross-sectional view of an assembled steerable laser probe 2000. Illustratively, pressure mechanism 1330 may be disposed over piston tube 1325, e.g., pressure mechanism distal end 1331 may abut pressure mechanism distal interface 1410. In one or more embodiments, pressure mechanism 1330 may be configured to provide a force. Illustratively, pressure mechanism 1330 may comprise a spring. Pressure mechanism 1330 may be manufactured from any suitable material, e.g., polymers, metals, metal alloys, etc., or from any combination of suitable materials.

In one or more embodiments, housing sleeve 250 may be disposed within actuation guide 245, nosecone 240, and housing sleeve guide 340, e.g., housing sleeve distal end 251 may extend a distance from nosecone distal end 241. Illustratively, actuation guide 245 may be disposed within actuation mechanism 1320 and piston tube 1325, e.g., actuation mechanism proximal end 247 may extend a distance from piston tube proximal end 1327. In one or more embodiments, actuation guide interface 1323 may be configured to interface with actuation guide 245, e.g., when actuation guide 245 is disposed within actuation mechanism 1320, actuation guide interface 1323 may be contained within actuation channel 310. Illustratively, pressure mechanism 1330 may be disposed between actuation mechanism 1320 and pressure mechanism proximal interface 1860, e.g., pressure mechanism proximal end 1332 may abut pressure mechanism proximal interface 1860 and pressure mechanism distal end 1331 may abut pressure mechanism distal interface 1410.

In one or more embodiments, actuation guide 245 may be disposed within inner bore 1840. Illustratively, piston tube 1325 and pressure mechanism 1330 may be disposed within actuation structure 1820. In one or more embodiments, a portion of actuation mechanism 1320 may be disposed within actuation structure 1820. Illustratively, optic fiber 270 and shape memory sleeve 260 may be disposed within inner bore 1840, actuation guide inner bore 320, piston tube 1325, actuation mechanism 1320, housing sleeve guide 340, and housing sleeve 250.

In one or more embodiments, fixation mechanism 1910 may be configured to fix optic fiber 270, shape memory sleeve 260, and actuation guide 245 in a position relative to handle 1800. For example, fixation mechanism 1910 may comprise a set screw configured to fix optic fiber 270, shape memory sleeve 260, and actuation guide 245 in a position relative to handle 1800, e.g., by an interference fit in actuation channel 310. In one or more embodiments, fixation mechanism 1910 may comprise an adhesive material configured to fix optic fiber 270, shape memory sleeve 260, and actuation guide 245 in a position relative to handle 1800, or fixation mechanism 1910 may comprise one or more magnets configured to fix optic fiber 270, shape memory sleeve 260, and actuation guide 245 in a position relative to handle 1800.

Illustratively, a compression of actuation structure 1820 may be configured to retract a portion of actuation mechanism 1320 into actuation structure 1820. For example, a compression of actuation structure 1820 may be configured to retract actuation mechanism 1320 relative to handle proximal end 1802. In one or more embodiments, an application of a compressive force to one or more actuation arms 1825 of actuation structure 1820 may be configured to retract actuation mechanism 1320 relative to handle proximal end 1802. For example, a compression of actuation structure 1820 may be configured to actuate actuation mechanism 1320 along actuation mechanism guide 245. In one or more embodiments, a compression of actuation structure 1820 may be configured to retract actuation guide interface 1323 within actuation channel 310, e.g., away from nosecone distal end 241 and towards handle proximal end 1802. Illustratively, pressure mechanism 1330 may be configured to provide a resistive force that resists a retraction of actuation mechanism 1320 relative to handle proximal end 1802.

In one or more embodiments, a retraction of actuation mechanism 1320 away from nosecone distal end 241 and towards handle proximal end 1802, e.g., due to a compression of actuation structure 1820, may be configured to retract housing sleeve 250 relative to optic fiber 270 and shape memory sleeve 260. Illustratively, a compression of actuation structure 1820 may be configured to actuate housing sleeve 250 relative to optic fiber 270 and shape memory sleeve 260 wherein optic fiber 270 and shape memory sleeve 260 may be gradually exposed by housing sleeve 250. In one or more embodiments, shape memory sleeve 260 may be configured to gradually curve optic fiber 270, e.g., towards pre-bent angle 265, as shape memory sleeve 260 and optic fiber 270 are gradually exposed by housing sleeve 250.

Illustratively, a decompression of actuation structure 1820 may be configured to extend a portion of actuation mechanism 1320 from actuation structure 1820. For example, a decompression of actuation structure 1820 may be configured to extend actuation mechanism 1320 relative to handle proximal end 1802. In one or more embodiments, a reduction of a compressive force applied to one or more actuation arms 1825 of actuation structure 1820 may be configured to extend actuation mechanism 1320 towards nosecone distal end 241 and away from handle proximal end 1802. For example, a decompression of actuation structure 1820 may be configured to actuate actuation mechanism 1320 along actuation mechanism guide 245. In one or more embodiments, a decompression of actuation structure 1820 may be configured to advance actuation guide interface 1323 within actuation channel 310, e.g., away from actuation guide proximal end 247 and towards nosecone distal end 241. Illustratively, pressure mechanism 1330 may be configured to provide a facilitating force that facilitates an extension of actuation mechanism 1320 relative to handle proximal end 1802.

In one or more embodiments, an extension of actuation mechanism 1320 towards nosecone distal end 241 and away from handle proximal end 1802, e.g., due to a decompression of actuation structure 1220, may be configured to extend housing sleeve 250 relative to shape memory sleeve 260 and optic fiber 270. Illustratively, a decompression of actuation structure 1820 may be configured to actuate housing sleeve 250 relative to shape memory sleeve 260 and optic fiber 270 wherein housing sleeve 250 may be gradually extended over shape memory sleeve 260 and optic fiber 270. In one or more embodiments, shape memory sleeve 260 and optic fiber 270 may be gradually straightened as housing sleeve 250 is gradually extended over shape memory sleeve 260 and optic fiber 270.

Figure 21A:
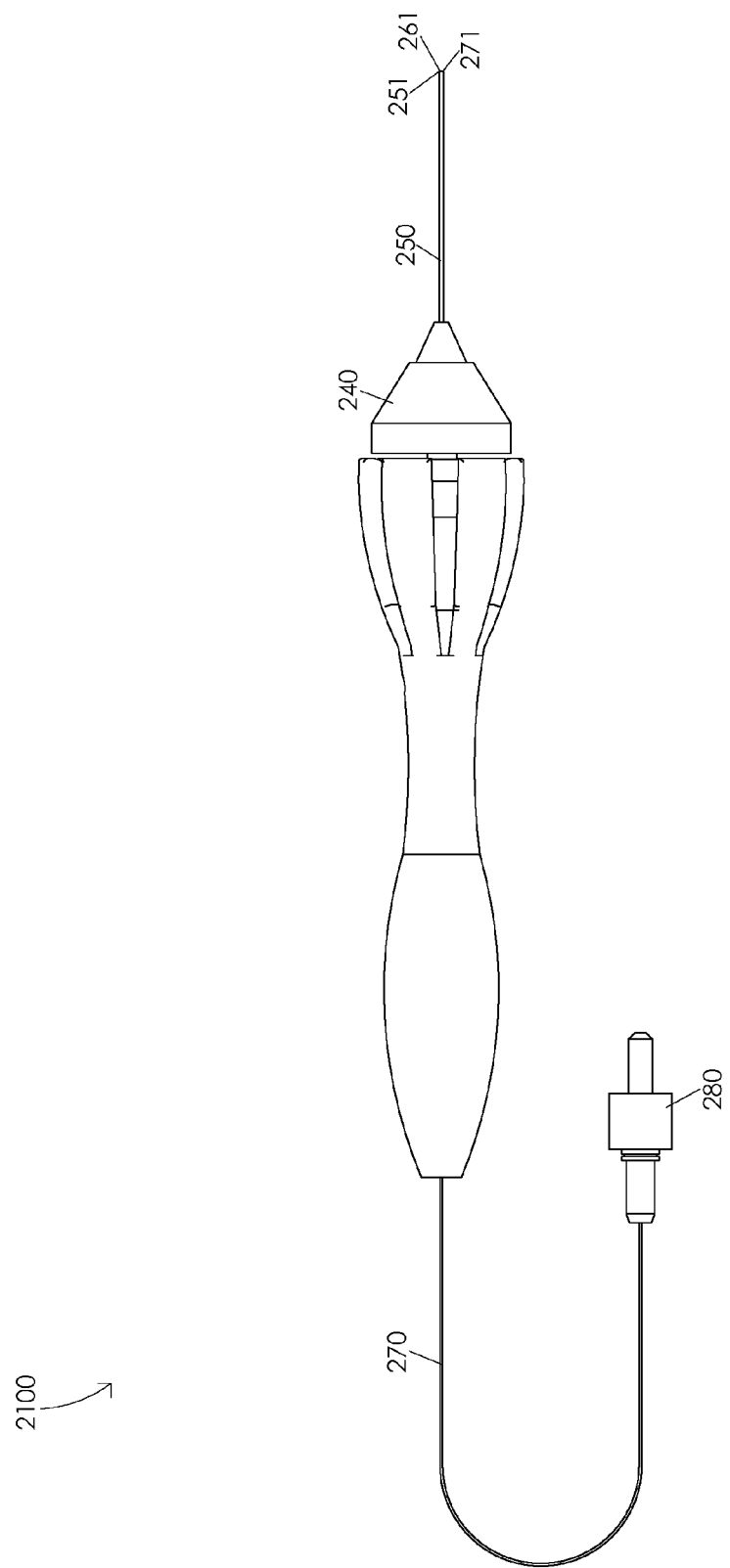
Figure 21C:
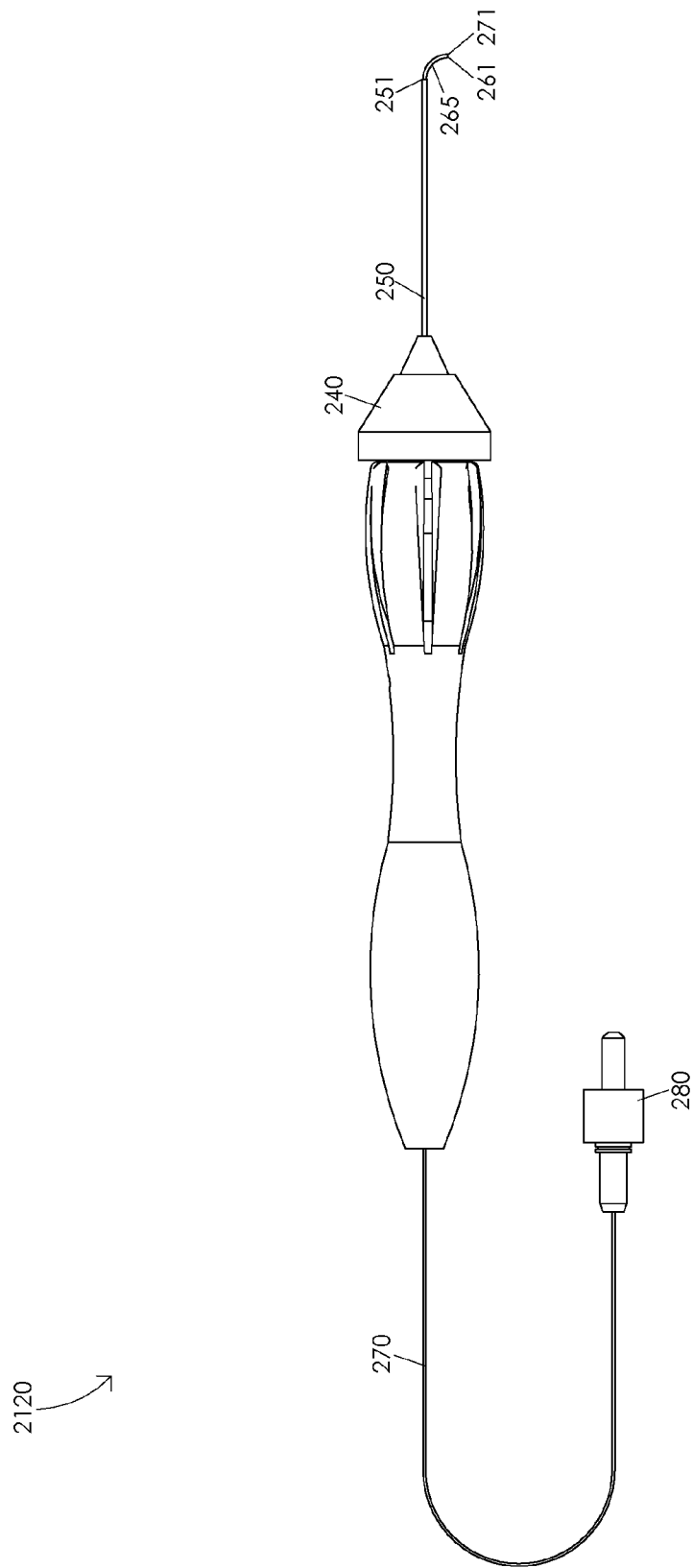

FIGS. 21A, 21B, and 21C are schematic diagrams illustrating a gradual curving of an optic fiber 270. FIG. 21A illustrates a straightened optic fiber 2100. Illustratively, straightened optic fiber 2100 may be fully contained within housing sleeve 250. In one or more embodiments, optic fiber 270 and shape memory sleeve 260 may be fully contained within housing sleeve 250, e.g., when actuation structure 1820 is fully decompressed. For example, actuation mechanism 1320 may be fully extended relative to handle proximal end 1802, e.g., when optic fiber 270 comprises a straightened optic fiber 2100. Illustratively, when optic fiber 270 and shape memory sleeve 260 are fully contained within housing sleeve 250, pre-bent angle 265 of shape memory sleeve 260 may be straightened by housing sleeve 250. For example, an angle between housing sleeve 250 and a line tangent to optic fiber distal end 271 may be, e.g., 180 degrees, when housing sleeve 250 contains a straightened optic fiber 2100.

FIG. 21B illustrates a partially curved optic fiber 2110. In one or more embodiments, a compression of a fully decompressed actuation structure 1820 may be configured to gradually retract housing sleeve 250, e.g., to expose optic fiber 270 and shape memory sleeve 260. Illustratively, as optic fiber 270 and shape memory sleeve 260 are gradually exposed by a retraction of housing sleeve 250, shape memory sleeve 260 may be configured to cause optic fiber 270 to gradually curve toward pre-bent angle 265. In one or more embodiments, a compression of actuation structure 1820 may be configured to cause a straightened optic fiber 2100 to gradually curve to a partially curved optic fiber 2110. Illustratively, a compression of actuation structure 1820 may be configured to gradually expose optic fiber 270 and shape memory sleeve 260 causing optic fiber 270 to gradually curve toward pre-bent angle 265. For example, as an exposed length of optic fiber 270 and shape memory sleeve 260 is increased, e.g., by a retraction of housing sleeve 250, an angle between housing sleeve 250 and a line tangent to optic fiber distal end 271 may be decreased.

Illustratively, optic fiber 270 and shape memory sleeve 260 may be exposed from housing sleeve distal end 251 at a first exposed length with a first angle between housing sleeve 250 and a line tangent to optic fiber distal end 271. A retraction of housing sleeve 250, e.g., due to a compression of actuation structure 1820, may be configured to expose optic fiber 270 and shape memory sleeve 260 from housing sleeve distal end 251 at a second exposed length with a second angle between housing sleeve 250 and a line tangent to optic fiber distal end 271. Illustratively, the second exposed length may be greater than the first exposed length and the second angle may be less than the first angle.

FIG. 21C illustrates a fully curved optic fiber 2120. Illustratively, when housing sleeve 250 is fully retracted, e.g., by a full compression of actuation structure 1820, housing sleeve 250 may expose a fully curved optic fiber 2120. In one or more embodiments, a compression of actuation structure

1820 may be configured to cause a partially curved optic fiber 2110 to gradually curve to a fully curved optic fiber 2120.

Illustratively, when housing sleeve 250 is retracted to expose a partially curved optic fiber 2110, optic fiber 270 and shape memory sleeve 260 may be exposed from housing sleeve distal end 251 at a partially exposed length with a partially exposed angle between housing sleeve 250 and a line tangent to optic fiber distal end 271. A retraction of housing sleeve 250, e.g., due to a full compression of actuation structure 1820, may be configured to expose optic fiber 270 and shape memory sleeve 260 from housing sleeve distal end 251 at fully exposed length with a fully exposed angle between housing sleeve 250 and a line tangent to optic fiber distal end 271. For example, housing sleeve 250 may expose optic fiber 270 and shape memory sleeve 260 at a fully exposed length with a fully exposed angle between housing sleeve 250 and a line tangent to optic fiber distal end 271 when housing sleeve 250 is retracted to expose a fully curved optic fiber 2120. Illustratively, the fully exposed length may be greater than the partially exposed length and the fully exposed angle may be less than the partially exposed angle.

In one or more embodiments, one or more properties of a steerable laser probe may be adjusted to attain one or more desired steerable laser probe features. Illustratively, a position of fixation mechanism housing 1850 and fixation mechanism 1910 or a length of optic fiber 270 and shape memory sleeve 260 extending distally from a position of fixation mechanism 1910 may be adjusted to vary an amount of compression of actuation structure 1820 configured to expose a particular length of optic fiber 270 and shape memory sleeve 260 from housing sleeve distal end 251. In one or more embodiments, one or more properties of pressure mechanism 1330 may be adjusted to attain one or more desired steerable laser probe features. Illustratively, a spring constant of pressure mechanism 1330 may be adjusted to vary an amount of compression of actuation structure 1820 configured to expose a particular length of optic fiber 270 and shape memory sleeve 260 from housing sleeve distal end 251. In one or more embodiments, a geometry of actuation mechanism 1320 may be adjusted to vary an amount of compression of actuation structure 1820 configured to expose a particular length of optic fiber 270 and shape memory sleeve 260 from housing sleeve distal end 251. Illustratively, a length of housing sleeve 250 may be adjusted to vary an amount of compression of actuation structure 1820 configured to expose a particular length of optic fiber 270 and shape memory sleeve 260 from housing sleeve distal end 251. In one or more embodiments, a geometry of actuation structure 1820 may be adjusted to vary an amount of compression of actuation structure 1820 configured to expose a particular length of optic fiber 270 and shape memory sleeve 260 from housing sleeve distal end 251. Illustratively, a magnitude of pre-bent angle 265 may be adjusted to vary a magnitude of an angle between housing sleeve 250 and a line tangent to optic fiber distal end 271 when a particular length of optic fiber 270 and shape memory sleeve 260 is exposed from housing sleeve distal end 251.

In one or more embodiments, one or more properties of optic fiber 270 may be adjusted to attain one or more steerable laser probe features. For example, a portion of optic fiber 270 may be formed in a pre-bent angle. Illustratively, a portion of optic fiber 270 may be formed in a pre-bent angle by, e.g., heating the portion of optic fiber 270 to a temperature configured to weaken chemical bonds of the portion of optic fiber 270, molding the portion of optic fiber 270 in a pre-bent angle, and cooling the portion of optic fiber 270. In one or more embodiments, optic fiber 270 may be coated by a buffer material. Illustratively, the buffer material may comprise a fluoropolymer, e.g., Teflon, Tefzel, etc. In one or more embodiments, a portion of optic fiber 270 may be formed in a pre-bent angle by, e.g., heating the buffer material to a temperature configured to weaken chemical bonds of the buffer material, molding the portion of optic fiber 270 in a pre-bent angle, and cooling the buffer material. Illustratively, housing sleeve 250 may be configured to hold a pre-bent angle of optic fiber 270 in a straightened position, e.g., when optic fiber 270 is fully contained within housing sleeve 250. In one or more embodiments, a compression of actuation structure 1820 may be configured to retract housing sleeve 250 relative to optic fiber 270 causing optic fiber 270 to gradually curve towards the pre-bent angle as optic fiber 270 is gradually exposed by housing sleeve 250.

Figure 22A:
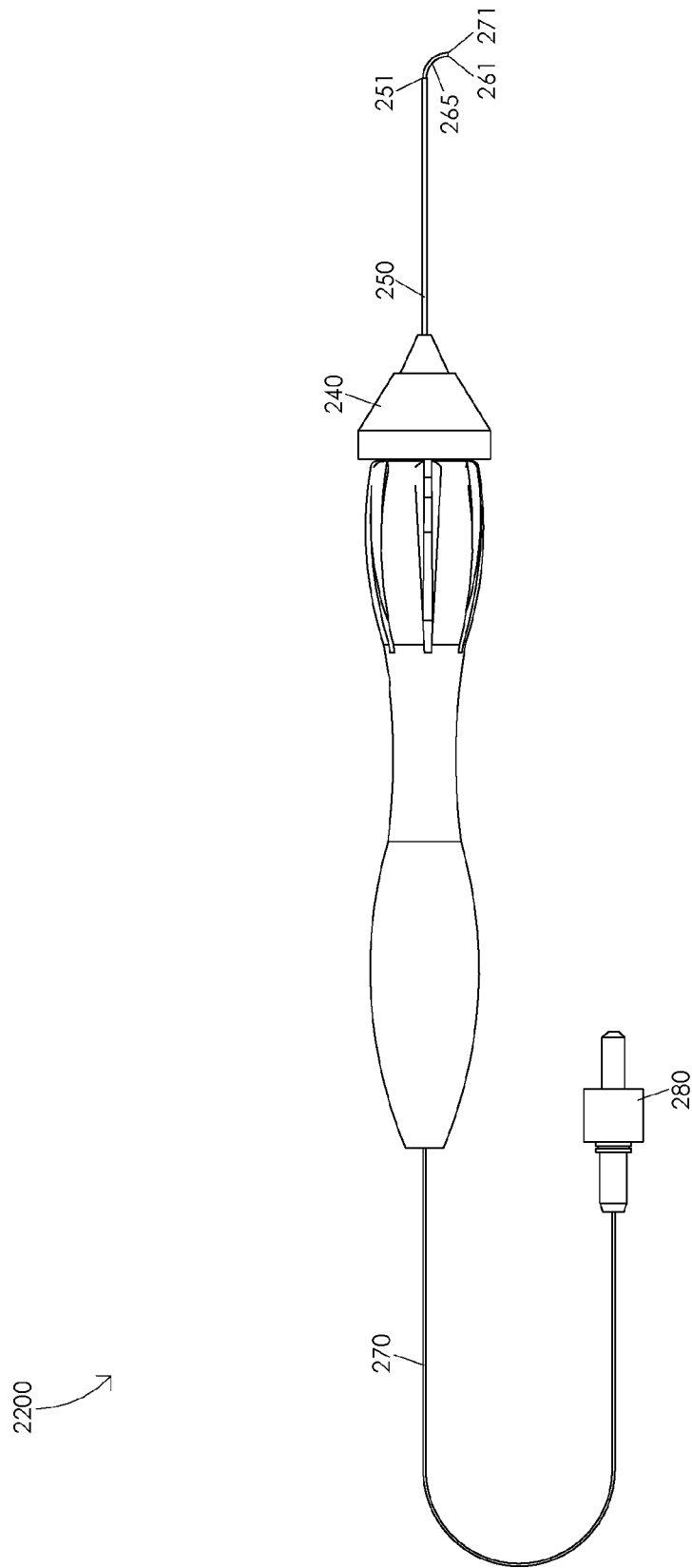
FIGS. 22A, 22B, and 22C are schematic diagrams illustrating a gradual straightening of an optic fiber.
Figure 22B:
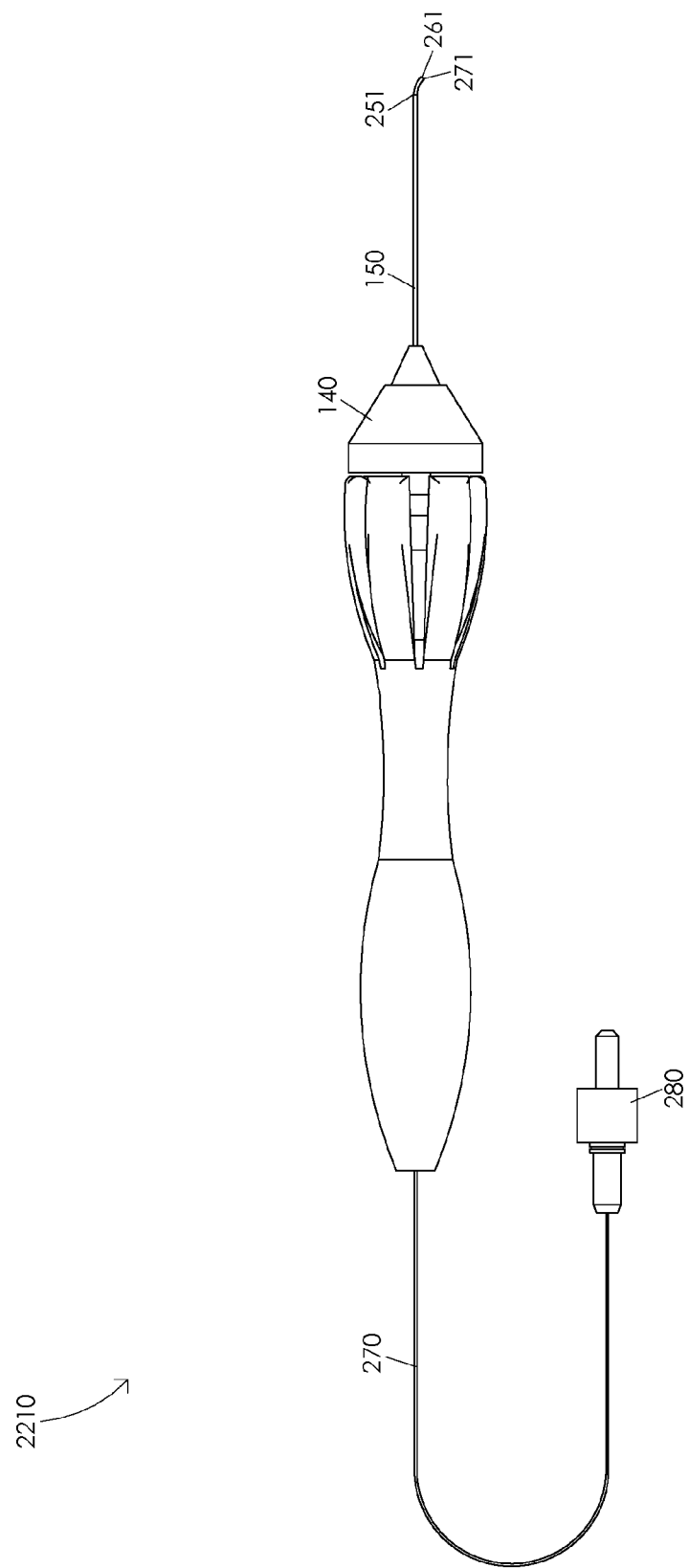
Figure 22C:
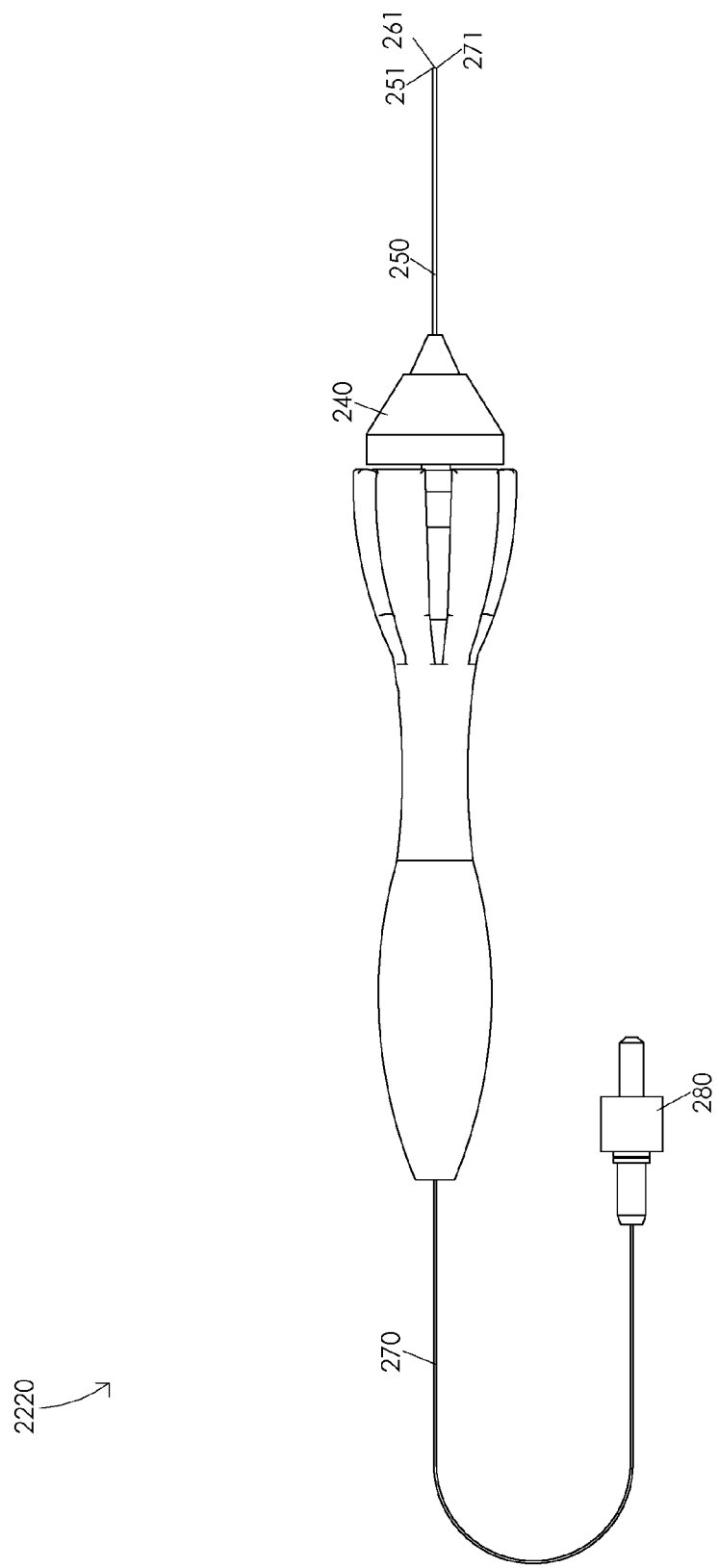

FIGS. 22A, 22B, and 22C are schematic diagrams illustrating a gradual straightening of an optic fiber 270. FIG. 22A illustrates a retracted housing sleeve 2200. Illustratively, a retracted housing sleeve 2200 may expose at least a portion of optic fiber 270 and shape memory sleeve 260 from housing sleeve distal end 251. In one or more embodiments, a full compression of actuation structure 1820 may be configured to cause housing sleeve 250 to be retracted relative to optic fiber 270 and shape memory sleeve 260 wherein a fully curved optic fiber 2120 may be exposed from housing sleeve distal end 251. Illustratively, housing sleeve 250 may comprise a retracted housing sleeve 2200, e.g., due to a full compression of actuation structure 1820.

FIG. 22B illustrates a partially extended housing sleeve 2210. Illustratively, a partially extended housing sleeve 2210 may hold a portion of pre-bent angle 265 in a straightened position within housing sleeve 250. In one or more embodiments, a decompression of actuation structure 1820 may be configured to extend housing sleeve 250 over optic fiber 270 and shape memory sleeve 260 causing shape memory sleeve 260 to gradually straighten optic fiber 270 from a fully curved optic fiber 2120 to a partially curved optic fiber 2110.

FIG. 22C illustrates a fully extended housing sleeve 2220. Illustratively, a fully extended housing sleeve 2220 may hold pre-bent angle 265 in a straightened position within housing sleeve 250. In one or more embodiments, a full decompression of actuation structure 1820 may be configured to extend housing sleeve 250 over optic fiber 270 and shape memory sleeve 260 causing shape memory sleeve 260 to gradually straighten optic fiber 270 from a partially curved optic fiber 2110 to a straightened optic fiber 2100.

Illustratively, a surgeon may aim optic fiber distal end 271 at any of a plurality of targets within an eye, e.g., to perform a photocoagulation procedure. In one or more embodiments, a surgeon may aim optic fiber distal end 271 at any target within a particular transverse plane of the inner eye by, e.g., rotating handle 1800 to orient shape memory sleeve 260 in an orientation configured to cause a curvature of optic fiber 270 within the particular transverse plane of the inner eye and varying an amount of compression of actuation structure 1820. Illustratively, a surgeon may aim optic fiber distal end 271 at any target within a particular sagittal plane of the inner eye by, e.g., rotating handle 1800 to orient shape memory sleeve 260 in an orientation configured to cause a curvature of optic fiber 270 within the particular sagittal plane of the inner eye and varying an amount of compression of actuation structure 1820. In one or more embodiments, a surgeon may aim optic fiber distal end 271 at any target within a particular frontal plane of the inner eye by, e.g., varying an amount of compression of actuation structure 1820 to orient a line tangent to optic fiber distal end 271 wherein the line tangent to optic fiber distal end 271 is within the particular frontal plane of the inner eye and rotating handle 1800. Illustratively, a surgeon may aim optic fiber distal end 271 at any target located outside of the particular transverse plane, the particular sagittal plane, and the particular frontal plane of the inner eye, e.g., by varying a rotational orientation of handle 1800 and varying an amount of compression of actuation structure 1820.

The foregoing description has been directed to particular embodiments of this invention. It will be apparent; however, that other variations and modifications may be made to the described embodiments, with the attainment of some or all of their advantages. Specifically, it should be noted that the principles of the present invention may be implemented in any probe system. Furthermore, while this description has been written in terms of a surgical instrument handle for selectively actuating a shape memory sleeve and an optic fiber relative to a housing sleeve and for selectively actuating a housing sleeve relative to a shape memory sleeve and an optic fiber, the teachings of the present invention are equally suitable to systems where the functionality of actuation may be employed. Therefore, it is the object of the appended claims to cover all such variations and modifications as come within the true spirit and scope of the invention.

What is claimed is:

1. An instrument comprising:
   a handle having a handle distal end and a handle proximal end;
   an actuation structure of the handle;
   a plurality of actuation arms of the actuation structure;
   a nosecone having a nosecone distal end and a nosecone proximal end;
   an actuation guide of the nosecone, the actuation guide disposed within an inner bore of the handle;
   an actuation mechanism having an actuation mechanism distal end and an actuation mechanism proximal end;
   a housing sleeve having a housing sleeve distal end and a housing sleeve proximal end, the housing sleeve fixed to a portion of the nosecone;
   a shape memory sleeve having a shape memory sleeve distal end and a shape memory sleeve proximal end, the shape memory sleeve at least partially disposed in the housing sleeve;
   a pre-bent angle of the shape memory sleeve; and
   an optic fiber having an optic fiber distal end and an optic fiber proximal end, the optic fiber disposed in the shape memory sleeve and in the inner bore of the handle wherein a compression of the actuation structure is configured to gradually curve the optic fiber.

2. The instrument of claim 1 further comprising:
   a fixation mechanism configured to fix the actuation guide in a position relative to the handle.

3. The instrument of claim 1 further comprising:
   a pressure mechanism having a pressure mechanism distal end and a pressure mechanism proximal end, the pressure mechanism configured to provide a force.

4. The instrument of claim 3 wherein the pressure mechanism is disposed within a nosecone inner chamber of the nosecone.

5. The instrument of claim 3 wherein the pressure mechanism is disposed over the actuation guide.

6. The instrument of claim 1 wherein the shape memory sleeve is manufactured from nitinol.

7. The instrument of claim 1 wherein the compression of the actuation structure is configured to extend the shape memory sleeve and the optic fiber relative to the housing sleeve.

8. The instrument of claim 1 wherein a decompression of the actuation structure is configured to gradually straighten the optic fiber.

9. An instrument comprising:
   a handle having a handle distal end and a handle proximal end;
   an actuation structure of the handle;
   a plurality of actuation arms of the actuation structure;
   a nosecone having a nosecone distal end and a nosecone proximal end;
   an actuation guide of the nosecone, the actuation guide disposed within an inner bore of the handle;
   an actuation mechanism having an actuation mechanism distal end and an actuation mechanism proximal end;
   a housing sleeve having a housing sleeve distal end and a housing sleeve proximal end, the housing sleeve fixed to a portion of the nosecone;
   a shape memory sleeve having a shape memory sleeve distal end and a shape memory sleeve proximal end, the shape memory sleeve at least partially disposed in the housing sleeve;
   a pressure mechanism having a pressure mechanism distal end and a pressure mechanism proximal end, the pressure mechanism configured to provide a force; and
   an optic fiber having an optic fiber distal end and an optic fiber proximal end, the optic fiber disposed in the shape memory sleeve and in the inner bore of the handle wherein a compression of the actuation structure is configured to gradually curve the optic fiber.

10. The instrument of claim 9 wherein the compression of the actuation structure is configured to extend the actuation mechanism relative to the handle proximal end.

11. The instrument of claim 10 wherein the force is a resistive force that resists an extension of the actuation mechanism relative to the handle proximal end.

12. The instrument of claim 9 wherein the compression of the actuation structure is configured to extend the optic fiber from the housing sleeve distal end.

13. The instrument of claim 9 wherein the pressure mechanism is disposed within a nosecone inner chamber of the nosecone.

14. The instrument of claim 9 wherein a decompression of the actuation structure is configured to gradually straighten the optic fiber.

15. An instrument comprising:
    a handle having a handle distal end and a handle proximal end;
    an actuation structure of the handle;
    a plurality of actuation arms of the actuation structure;
    a nosecone having a nosecone distal end and a nosecone proximal end;
    an actuation guide of the nosecone, the actuation guide disposed within an inner bore of the handle;
    an actuation mechanism having an actuation mechanism distal end and an actuation mechanism proximal end;
    a housing sleeve having a housing sleeve distal end and a housing sleeve proximal end, the housing sleeve fixed to a portion of the nosecone;
    a shape memory sleeve having a shape memory sleeve distal end and a shape memory sleeve proximal end, the shape memory sleeve at least partially disposed in the housing sleeve;
    a pre-bent angle of the shape memory sleeve; and
    an optic fiber having an optic fiber distal end and an optic fiber proximal end, the optic fiber disposed in the shape memory sleeve and in the inner bore of the handle wherein a compression of the actuation structure is configured to extend the shape memory sleeve relative to the housing sleeve.

16. The instrument of claim 15 wherein the compression of the actuation structure is configured to gradually curve the optic fiber.

17. The instrument of claim 16 wherein a decompression of the actuation structure is configured to gradually straighten the optic fiber.

18. The instrument of claim 15 further comprising:
a fixation mechanism configured to fix the actuation guide in a position relative to the handle.

19. The instrument of claim 15 further comprising:
a pressure mechanism having a pressure mechanism distal end and a pressure mechanism proximal end, the pressure mechanism configured to provide a force.

20. The instrument of claim 19 wherein the pressure mechanism is disposed within a nosecone inner chamber of the nosecone.

\* \* \* \* \*